United States Patent
Shaikh et al.

(10) Patent No.: US 11,572,516 B2
(45) Date of Patent: Feb. 7, 2023

(54) SYSTEMS AND PROCESSES INTEGRATING STEAM CRACKING WITH DUAL CATALYST METATHESIS FOR PRODUCING OLEFINS

(71) Applicant: Saudi Arabian Oil Company, Dhahran (SA)

(72) Inventors: Sohel K Shaikh, Dhahran (SA); Raed H Abudawoud, Khobar (SA); Zhonglin Zhang, Dhahran (SA); Munir D Khokhar, Dhahran (SA); Furqan Aljumah, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/830,759

(22) Filed: Mar. 26, 2020

(65) Prior Publication Data
US 2021/0301213 A1 Sep. 30, 2021

(51) Int. Cl.
*C10G 69/06* (2006.01)
*C07C 6/04* (2006.01)
(Continued)

(52) U.S. Cl.
CPC .......... *C10G 69/06* (2013.01); *B01J 19/1862* (2013.01); *C07C 1/22* (2013.01); *C07C 4/04* (2013.01);
(Continued)

(58) Field of Classification Search
CPC .... C10G 69/06; C10G 51/023; C10G 51/026; C10G 51/06; C10G 65/10; C10G 65/12;
(Continued)

(56) References Cited

U.S. PATENT DOCUMENTS

| 3,442,821 A | 5/1969 | Hilfman |
| 3,546,313 A | 12/1970 | Banks |

(Continued)

FOREIGN PATENT DOCUMENTS

| CN | 101514135 A | 8/2009 |
| CN | 101531558 A | 9/2009 |

(Continued)

OTHER PUBLICATIONS

Office Action dated Jul. 2, 2021 pertaining to Chinese Patent Application No. 201880010205.4.
(Continued)

*Primary Examiner* — In Suk C Bullock
*Assistant Examiner* — Jason Y Chong
(74) *Attorney, Agent, or Firm* — Dinsmore & Shohl LLP

(57) ABSTRACT

Processes for producing olefins include integration of steam cracking with a dual catalyst metathesis process. The processes include steam cracking a hydrocarbon feed to form a cracking reaction effluent containing butenes, separating the cracking reaction effluent to produce a cracking C4 effluent including normal butenes, isobutene, and 1,3-butadiene, subjecting the cracking C4 effluent to selective hydrogenation to convert 1,3-butadiene in the cracking C4 effluent to normal butenes, removing isobutene from a hydrogenation effluent to produce a metathesis feed containing normal butenes, and contacting the metathesis feed with a metathesis catalyst and a cracking catalyst directly downstream of the metathesis catalyst to produce a metathesis reaction effluent. Contacting with the metathesis catalyst causes metathesis of normal butenes to produce ethylene, propene, and C5+ olefins, and contacting with the cracking catalyst causes C5+ olefins produced through metathesis to undergo cracking reactions to produce additional propene, ethylene, or both.

12 Claims, 5 Drawing Sheets

(51) Int. Cl.
*C07C 11/06* (2006.01)
*B01J 19/18* (2006.01)
*C07C 1/22* (2006.01)
*C07C 4/04* (2006.01)
*C07C 4/06* (2006.01)
*C07C 5/05* (2006.01)
*C07C 41/06* (2006.01)
*C10G 51/02* (2006.01)
*C10G 51/06* (2006.01)
*C10G 65/10* (2006.01)
*C10G 65/12* (2006.01)

(52) U.S. Cl.
CPC ............... *C07C 4/06* (2013.01); *C07C 5/05* (2013.01); *C07C 6/04* (2013.01); *C07C 41/06* (2013.01); *C10G 51/023* (2013.01); *C10G 51/026* (2013.01); *C10G 51/06* (2013.01); *C10G 65/10* (2013.01); *C10G 65/12* (2013.01); *B01J 2219/0004* (2013.01); *C10G 2300/1044* (2013.01); *C10G 2400/20* (2013.01)

(58) Field of Classification Search
CPC ........ C10G 2300/1044; C10G 2400/20; C07C 6/04; C07C 1/22; C07C 5/05; C07C 4/04; C07C 4/06; C07C 41/06; B01J 2219/0004; B01J 19/1862
See application file for complete search history.

(56) References Cited

U.S. PATENT DOCUMENTS

| | | |
|---|---|---|
| 3,586,731 A | 6/1971 | Heckelsberg |
| 3,702,886 A | 11/1972 | Argauer et al. |
| 3,728,415 A | 4/1973 | Arganbright |
| 4,024,201 A | 5/1977 | Takahashi |
| 4,071,471 A | 1/1978 | Banks et al. |
| 4,575,575 A | 3/1986 | Drake et al. |
| 4,609,769 A | 9/1986 | Kukes et al. |
| 5,026,935 A | 6/1991 | Leyshon et al. |
| 5,026,936 A | 6/1991 | Leyshon et al. |
| 5,191,131 A | 3/1993 | Takahata et al. |
| 5,439,859 A | 8/1995 | Durante et al. |
| 5,523,502 A | 6/1996 | Rubin |
| 5,877,365 A | 3/1999 | Chodorge et al. |
| 6,159,433 A | 12/2000 | Chodorge et al. |
| 6,207,115 B1 | 3/2001 | Chodorge et al. |
| 6,215,062 B1 | 4/2001 | Kimber |
| 6,538,168 B1 | 3/2003 | Schwab et al. |
| 6,580,009 B2 * | 6/2003 | Schwab ................ C10G 70/00 585/324 |
| 6,586,649 B1 | 7/2003 | Botha et al. |
| 6,646,172 B1 | 11/2003 | Schwab et al. |
| 6,777,582 B2 | 8/2004 | Gartside et al. |
| 6,977,321 B1 | 12/2005 | Dath et al. |
| 7,214,841 B2 | 5/2007 | Gartside et al. |
| 7,754,647 B2 | 7/2010 | Schubert et al. |
| 7,754,934 B2 | 7/2010 | Tsunoda et al. |
| 7,977,522 B2 | 7/2011 | Takai et al. |
| 8,299,313 B2 | 10/2012 | Takai et al. |
| 8,324,440 B2 | 12/2012 | Popp et al. |
| 8,362,308 B2 | 1/2013 | Stephan et al. |
| 8,440,874 B2 | 5/2013 | Ramachandran et al. |
| 8,586,813 B2 | 11/2013 | Ramachandran et al. |
| 8,722,568 B2 | 5/2014 | Popp et al. |
| 9,834,497 B2 | 12/2017 | Shaikh et al. |
| 9,884,794 B2 | 2/2018 | Al-Khattaf et al. |
| 2003/0176754 A1 | 9/2003 | Gartside et al. |
| 2004/0254411 A1 | 12/2004 | Steinbrenner et al. |
| 2005/0014981 A1 | 1/2005 | Gartside et al. |
| 2005/0124839 A1 | 6/2005 | Gartside et al. |
| 2006/0047176 A1 | 3/2006 | Gartside et al. |
| 2006/0293548 A1 | 12/2006 | Spamer et al. |
| 2007/0038010 A1 | 2/2007 | Xie et al. |
| 2007/0225478 A1 | 9/2007 | Querci et al. |
| 2008/0033223 A1 | 2/2008 | Sigi et al. |
| 2008/0171655 A1 | 7/2008 | Creyghton et al. |
| 2010/0041930 A1 | 2/2010 | Gartside et al. |
| 2010/0168487 A1 | 7/2010 | Sawyer et al. |
| 2010/0234542 A1 | 9/2010 | Blackborow et al. |
| 2011/0021858 A1 | 1/2011 | Ramachandran et al. |
| 2011/0152595 A1 | 6/2011 | Takai et al. |
| 2011/0196185 A1 | 8/2011 | Krawczyk et al. |
| 2012/0108864 A1 | 5/2012 | Gartside et al. |
| 2012/0264990 A1 | 10/2012 | Nicholas et al. |
| 2012/0283090 A1 | 11/2012 | Popp et al. |
| 2012/0289617 A1 | 11/2012 | Wang et al. |
| 2013/0085311 A1 | 4/2013 | Youn et al. |
| 2013/0165701 A1 | 6/2013 | Zhou et al. |
| 2013/0245348 A1 | 9/2013 | Vermeiren et al. |
| 2013/0303806 A1 | 11/2013 | Winterberg et al. |
| 2014/0148629 A1 | 5/2014 | van Hal et al. |
| 2015/0141720 A1 | 5/2015 | Ramachandran et al. |
| 2015/0141721 A1 | 5/2015 | Choi et al. |
| 2015/0251968 A1 | 9/2015 | Brianti et al. |
| 2016/0130197 A1 | 5/2016 | Al-Khattaf et al. |
| 2016/0237006 A1 | 8/2016 | Stoyanova et al. |
| 2017/0001925 A1 | 1/2017 | Abudawoud et al. |
| 2017/0001926 A1 | 1/2017 | Shaikh et al. |
| 2017/0001927 A1 | 1/2017 | Al-Khattaf et al. |
| 2017/0001928 A1 | 1/2017 | Shaikh et al. |
| 2017/0253540 A1 * | 9/2017 | Hofei ................ C07C 41/06 |
| 2018/0057425 A1 | 3/2018 | Shaikh et al. |
| 2018/0142167 A1 | 5/2018 | Al-Ghamdi et al. |
| 2018/0208524 A1 | 7/2018 | Alshafei et al. |
| 2018/0208526 A1 * | 7/2018 | Alshafei ................ B01J 35/002 |
| 2018/0208527 A1 | 7/2018 | Khokhar et al. |
| 2018/0230071 A1 | 8/2018 | Bonduelle et al. |
| 2019/0367432 A1 | 12/2019 | Al-Majnouni et al. |

FOREIGN PATENT DOCUMENTS

| | | |
|---|---|---|
| CN | 102177223 A | 9/2011 |
| CN | 102325742 A | 1/2012 |
| CN | 104370676 A | 2/2015 |
| CN | 100448820 C | 1/2019 |
| DE | 10013253 A1 | 9/2001 |
| EP | 304515 B1 | 12/1991 |
| EP | 838449 A1 | 4/1998 |
| EP | 920911 A1 | 6/1999 |
| EP | 2151424 A1 | 2/2010 |
| GB | 1205677 A | 9/1970 |
| JP | 2003500190 A | 1/2003 |
| JP | 2012500304 A | 1/2012 |
| KR | 1020210027788 A | 3/2021 |
| NL | 8403050 A | 5/1986 |
| RU | 2370314 C1 | 10/2009 |
| WO | 9929805 A1 | 6/1999 |
| WO | 0071255 A1 | 11/2000 |
| WO | 2006089957 A1 | 8/2006 |
| WO | 2008136280 A1 | 11/2008 |
| WO | 2009015118 A2 | 1/2009 |
| WO | 2009117128 A1 | 9/2009 |
| WO | 2010019595 A2 | 2/2010 |
| WO | 2011136983 A1 | 11/2011 |
| WO | 2015055594 A1 | 4/2015 |
| WO | 2017003812 A1 | 1/2017 |
| WO | 2017003817 A1 | 1/2017 |
| WO | 2017003821 A1 | 1/2017 |
| WO | 2018088815 A1 | 5/2018 |

OTHER PUBLICATIONS

Notice of Allowance and Fee(s) Due dated Dec. 10, 2020 pertaining to U.S. Appl. No. 16/390,523, filed Apr. 22, 2019, 22 pgs.
U.S. Office Action dated Mar. 2, 2021 pertaining to U.S. Appl. No. 16/712,280, filed Dec. 12, 2019, 34 pgs.
Notice of Allowance and Fee(s) Due dated Nov. 23, 2020 pertaining to U.S. Appl. No. 16/156,616, filed Oct. 10, 2018, 29 pgs.
Examination Report pertaining to GCC Application No. 2016/31673 dated Apr. 7, 2020.

(56) References Cited

OTHER PUBLICATIONS

Office Action dated May 27, 2020 pertaining to U.S. Appl. No. 16/156,616, filed Oct. 10, 2018, 31 pgs.
Office Action dated Jul. 24, 2020 pertaining to U.S. Appl. No. 15/866,800, filed Jan. 10, 2018, 51 pgs.
Office Action dated Jul. 14, 2020 pertaining to U.S. Appl. No. 16/390,523, filed Apr. 22, 2019, 42 pgs.
Notice of Allowance and Fee(s) Due dated Oct. 19, 2020 pertaining to U.S. Appl. No. 15/866,800, filed Jan. 10, 2018, 27 pgs.
Search Report and Written Opinion pertaining to Singapore Application No. 10201913486W dated Jul. 21, 2020.
Notice of Allowance and Fee(s) Due dated Jul. 23, 2021 pertaining to U.S. Appl. No. 16/712,280, filed Dec. 12, 2019, 24 pages.
Office Action dated May 21, 2021 pertaining to U.S. Appl. No. 16/775,677, filed Jan. 29, 2020, 85 pgs.
International Search Report and Written Opinion dated May 31, 2021 pertaining to International application No. PCT/US2020/060438 filed Nov. 13, 2020, 12 pages.
Arudra et al., "Silicalite-1 as Efficient Catalyst for Production of Propene from 1-Butene", ACS Catalysis, 2014, 1205-4212, 4, American Chemical Society.
Awayssa et al., "Modified HZSM-5 as FCC Additive for Enhancing Light Olefins Yield from Catalytic Cracking of VGO", Applied Catalysis A: General, 2014, 172-183, 477.
Balcar, et al., "Mesoporous molecular sieves as advanced supports for olefin metathesis catalysts". Coordination Chemistry Reviews 257, 2013, pp. 3107-3124, Czech Republic.
Barrett et al., "The Determination of Pore Volume and Area Distributions in Porous Substances. I. Computations from Nitrogen Isotherms", J. Am. Chem. Soc., 1951, 373-380, 73(1).
Beck et al., "A New Family of Mesoporous Molecular Sieves Prepared with Liquid Crystal Templates", J. Am. Chem. Soc., 1992, 10834-10843, 114, American Chemical Society.
Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.
Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.
Bin Hu, et al., "Highly Active Doped Mesoporous KIT-6 Catalysts for Metathesis of 1-Butene and Ethene to Propene: The Influence of Neighboring Environment of W Species", The Journal of Physical Chemistry, ACS Publication, 2013 American Chemical Society, pp. 26385-26395, USA.
Daniell et al., "Enhanced Surface Acidity in Mixed Alumina-Silicas: A Low-Temperature" FTIR Study:, 2000, 196, 247-260, Elsevier.
Do et al., "Zeolite Nanoclusters Coated onto the Mesopore Walls of SBA-15", J. Am. Chem. Soc., 2004, 14324-14325, 126, American Chemical Society.
International Search Report and Written Opinion dated Nov. 11, 2016 pertaining to International Application No. PCT/US2016/039025.
International Search Report and Written Opinion dated Sep. 14, 2016 pertaining to International Application No. PCT/US2016/039012.
International Search Report and Written Opinion dated Sep. 27, 2016 pertaining to International Application No. PCT/US2016/0038967.
International Search Report and Written Opinion dated Sep. 14, 2016 pertaining to International Application No. PCT/US2016/039013.
Jermy et al., "Utilization of ZSM-5/MCM-41 Composite as FCC Catalyst Additive for Enhancing Propylene Yield from VGO Cracking", J Porous Mater, 2012, 499-509, 19, Springer.
Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.

Kumar et al., "Performance of Nano Crystalline H-ZSM-5 As Additive in FCC Catalyst: A Review", International Journal of Research in Engineering and Tehnology, May 2014, vol. 3, pp. 481-485.
Lwin et al., "Olefin Metathesis by Supported Metal Oxide Catalysts", ACS Catalysis, 2014, 2505-2520, 4, American Chemical Society.
Office Action pertaining to U.S. Appl. No. 15/190,950 dated Sep. 27, 2017.
Office Action pertaining to U.S. Appl. No. 15/190,964 dated Nov. 2, 2017.
Quignard et al., "Aryloxide Ligands in Metathesis of Olefins and Olefinic Esters: Catalytic Behaviour ofW(OAr)2Cl4 by SnMe4, Sn(n-Bu)4, Pb(n-Bu)4, MgNp2: synthesis of W(OAr)2Cl2(CHCMe3)(OR2) and W(OAr)2Cl(CHCMe3)(CH2CMe3)(OR2)", Journal of Molecular Catalysis, 1986, 36, 13-29.
Ruihua Gao, et al., "High-activity, single-site mesoporous WO3-MCF materials for the catalytic epoxidation of cycloocta-1,5-diene with aqueous hydrogen peroxide", Journal of Catalysis, 256, 2008, pp. 259-267, China.
Wang et al., "Synthesis and Structure of Silicalite-1/SBA-15 Composites Prepared by Carbon Templating and Crystallization", Journal of Materials Chemistry, 2007,4265-4273,17, The Royal Society of Chemistry 2007.
Wang et al., "Effect of Support Nature on WO3/SiO2 Structure and Butene-1 Metathesis", Applied Catalysis A General, 2003, 25-37, 250, Elsevier B.V.
Zhao et al., "Effect of Tungsten Oxide Loading on Metathesis Activity of Ethene and 2-Butene Over WO3/SiO2 Catalysts" Transition Met Chem, 2009, 621-27, 34, Springer.
International Preliminary Report on Patentability dated Jan. 11, 2018—PCT/US2016/039012.
International Preliminary Report on Patentability dated Jan. 2, 2018—PCT/US2016/039012.
Non-Final Office Action pertaing to U.S. Appl. No. 15/398,196 dated Jan. 9, 2018.
Puriwat, et al., "Elucidation of the basicity dependence of 1-butene isomerization on MgO/Mg(OH)s catalysts", Catalysis Communications, 2010, pp. 80-85.
International Search Report and Written opinion dated Mar. 28, 2018, pertaining to International Application No. PCT/US2018/013945, filed Jan. 17, 2018, 9 pages.
U.S. Office Action dated Apr. 20, 2018 pertaining to U.S. Continuation U.S. Appl. No. 15/859,794, filed Jan. 2, 2018.
International Search Report and Written Opinion dated Apr. 24, 2018 pertaining to International Application No. PCT/US2018/014131, filed Jan. 18, 2018.
Notice of Allowance dated Apr. 24, 2018 pertaining to U.S. Appl. No. 15/190,964, filed Jun. 23, 2016.
Election/Restriction Requirement dated May 21, 2018, pertaining to U.S. Appl. No. 15/866,772, filed Jan. 10, 2018.
Korean Office Action pertaining to Korea Application No. 10-2018-7003238 dated May 14, 2018 (English Translation).
Office Action pertaining to U.S. Appl. No. 15/866,800 dated Jun. 29, 2018.
Office Action pertaining to U.S. Appl. No. 15/190,981 dated Apr. 4, 2017.
Office Action pertaining to U.S. Appl. No. 15/866,772 dated Aug. 28, 2018.
Harmse et al., "On the Product Formation in 1-Butene Methathesis over Supported Tungsten Catalysts", Catal. Lett, vol. 137, pp. 123-131, Apr. 2010.
Shaikh et al., "Self-Methathesis of Butenes to Propylene", Catalysis in Petroleum Refining & Petrochemicals, pp. 1-6, Dec. 7-8, 2015.
Debecker et al., "Preparation of Mo03/si02-Al203 methathesis catalysts via wet impregnation with different Mo precursors". Journal of Molecular Catalysis A: Chemical, 340, pp. 65-76, 2011.
Wu et al., "Investigation on acidity of zeolites bound with silica and alumina", Studies in Surface Science and Catalysis, 143, pp. 217-225, 2002.
Hu et al., "Highly active doped mesoporous KIT-6 catalysts for mathesis of 1-butene and ethene to propene: The influence of

(56) References Cited

OTHER PUBLICATIONS neiboring environment of W. species", Journal of Physical Chemistry, vol. 117, pp. 26385-26395, 2013.
Examination Report pertaining to GCC Application No. 2016/31672 dated Sep. 13, 2018.
Office Action dated Jan. 31, 2019 pertaining to U.S. Appl. No. 15/866,800, filed Jan. 10, 2018 (34 pg).
Notice of Allowance dated Mar. 5, 2019 pertaining to U.S. Appl. No. 15/866,772, filed Jan. 10, 2018.
Office Action dated Apr. 5, 2019 pertaining to U.S. Appl. No. 15/873,421, filed Jan. 17, 2018, 49 pgs.
Office Action dated May 2, 2019 pertaining to U.S. Appl. No. 15/859,794, filed Jan. 2, 2018, 30 pgs.
Office Action dated May 2, 2019 pertaining to U.S. Appl. No. 16/156,634, filed Oct. 10, 2018, 32 pgs.
Office Action dated Apr. 29, 2019 pertaining to U.S. Appl. No. 16/039,983, filed Jul. 19, 2018, 36 pgs.
Notice of Allowance and Fee(s) Due dated Apr. 19, 2021 pertaining to U.S. Appl. No. 16/522,142, filed Jul. 25, 2019, 15 pgs.
Notice of Allowance and Fee(s) Due dated Apr. 21, 2021 pertaining to U.S. Appl. No. 16/156,634, filed Oct. 10, 2018, 17 pgs.
International Search Report and Written Opinion dated Feb. 23, 2021 pertaining to International application No. PCT/US2020/058640 filed Nov. 3, 2020, 14 pgs.
Yuan Guimei et al., Machine translation of CN 104370676, Feb. 2015.
Notice of Allowance and Fee(s) Due dated May 15, 2019 pertaining to U.S. Appl. No. 16/156,616, filed Oct. 10, 2018, 35 pgs.
U.S. Office Action dated Jun. 14, 2019 pertaining to U.S. Appl. No. 15/866,800, filed Jan. 10, 2018, 38 pgs.
Office Action dated Jun. 18, 2019 pertianing to Korean Patent Application No. 10-2018-7003251.
Office Action dated Mar. 30, 2019 pertaining to Japanese Patent Application No. 2017-567370.
European Search Report for Application No. 19163840.2 dated Aug. 2, 2019.
Chinese Office Action for Application No. 201811179717.1 dated Jun. 13, 2019.
European Search Report for Application No. 16738274.6 dated Aug. 1, 2019.
Notice of Allowance and Fee(s) Due dated Aug. 29, 2019 pertaining to U.S. Appl. No. 15/859,794, filed Jan. 2, 2018, 22 pgs.
Notice of Allowance and Fee(s) Due dated Sep. 26, 2019 pertaining to U.S. Appl. No. 15/873,421, filed Jan. 17, 2018, 30 pgs.
Examination Report for Application No. GC 2018/34631 dated Aug. 22, 2019.
Decision of Rejection pertaining to Japanese Application No. 2017-567370 dated Sep. 4, 2019.
Notice of Allowance and Fee(s) due dated Oct. 18, 2019 pertaining to U.S. Appl. No. 16/039,983, filed Jul. 19, 2018, 29 pgs.
Machine translation claims of CN 102177223 A, Sep. 2011.
Machine translation description CN 102177223 A, Sep. 2011.
Office Action dated Nov. 20, 2019 pertaining to U.S. Appl. No. 16/156,634, filed Oct. 10, 2018, 37 pgs.
Office Action pertaining to U.S. Appl. No. 15/866,800 dated Jan. 13, 2020.
Office Action pertaining to U.S. Appl. No. 16/390,523 dated Jan. 17, 2020.
Bortnovsky et al., "Cracking of pentenes to C2-C4 light olefins over zeolites and zeotypes Role of topology and acid site strength and concentration", Applied Catalysis A: General 287, pp. 203-213, 2005.
Debecker et al., "Aerosol route to nanostructured WO3—SiO2—Al2O3 methathesis catalysts: Toward higer propene yield". Applied Catalysis A: General 470, pp. 458-466, 2014.
International Search Report and Written Opinion pertaining to Application No. PCT/US2019/054378 dated Jan. 13, 2020.
International Search Report and Written Opinion pertaining to Application No. PCT/US2019/054377 dated Jan. 13, 2020.
Korean Office Action pertaining to Korea Application No. 10-2019-7005618 dated Feb. 25, 2020 (English Translation).
U.S. Office Action dated Aug. 21, 2020 pertaining to U.S. Appl. No. 16/712,280, filed Dec. 12, 2019, 67 pgs.
U.S. Office Action dated Sep. 15, 2020 pertaining to U.S. Appl. No. 16/156,634, filed Oct. 10, 2018, 38 pgs.
U.S. Office Action dated Sep. 16, 2020 pertaining to U.S. Appl. No. 16/522,142, filed Jul. 25, 2019, 72 pgs.
U.S. Notice of Allowance and Fee(s) Due dated Feb. 25, 2022 pertaining to U.S. Appl. No. 16/775,677 filed Jan. 29, 2020, 14 pages.
U.S. Office Action dated Oct. 20, 2021 pertaining to U.S. Appl. No. 16/775,677, filed Jan. 29, 2020, 29 pages.
Office Action dated Jul. 6, 2021 pertaining to Chinese Patent Application No. 201880006954.X.
Notification of Transmittal of the International Search Report and Written Opinion of the International Searching Authority, or the Declaration dated Nov. 14, 2022 pertaining to International application No. PCT/US2022/037792 filed Jul. 21, 2022, 29 pages.

\* cited by examiner

SYSTEMS AND PROCESSES INTEGRATING STEAM CRACKING WITH DUAL CATALYST METATHESIS FOR PRODUCING OLEFINS

TECHNICAL FIELD

Embodiments of the present disclosure generally relate to systems and processes for producing olefins from hydrocarbon feed compositions, in particular, systems and processes integrating steam cracking systems and dual catalyst metathesis systems for producing olefins.

BACKGROUND

Ethylene, propene, butene, butadiene, and aromatics compounds such as benzene, toluene and xylenes are basic intermediates for the petrochemical industry. These compounds can be produced through steam cracking (thermal cracking or steam pyrolysis) of petroleum gases and distillates such as naphtha, kerosene, or even gas oil. These compounds are also produced through refinery fluidized catalytic cracking (FCC) process where classical heavy feedstocks such as gas oils or residues are converted. Typical steam cracking feedstocks range from hydrocracked bottoms to heavy feed fractions such as vacuum gas oil and atmospheric residue; however, these feedstocks are limited.

The worldwide increasing demand for light olefins remains a major challenge for many integrated refineries. In particular, the production of some valuable light olefins such as ethylene, propene, and butene has attracted increased attention as purified olefin streams are considered the building blocks for polymer synthesis. The production of light olefins depends on several process variables, such as the feed type, operating conditions, and the type of catalyst. Despite the options available for producing a greater yield of propene and light olefins, intense research activity in this field is still being conducted.

SUMMARY

Steam cracking units can be used to convert hydrocarbon feed streams to light olefins, such as ethylene and propene. However, steam cracking systems can produce substantial amounts of C4+ compounds, such as mixed butenes (1-butene, trans-2-butene, cis-2-butene, isobutene) butane, and isobutane, isobutene, and 1,3-butadiene, as well as pentene, aromatic compounds, and other C5+ hydrocarbons. Production of these larger hydrocarbons may reduce the selectivity and yield of propene, ethylene, or both, from the steam cracking system. Accordingly, ongoing needs exist for processes and systems for producing olefins, such as propene and ethylene, from hydrocarbon feedstocks at greater selectivity and yield of propene, ethylene, or both, compared to commercially available steam cracking processes. Additionally, ongoing needs exist for processes and systems for producing olefins, such as propene and ethylene, from a broader spectrum of hydrocarbon feedstocks, such as feedstocks including naphtha streams or gas condensate streams.

The systems and processes of the present disclosure include a steam cracking system integrated with a metathesis system downstream of the steam cracking system. The steam cracking system may be operable to contact the hydrocarbon feed, such as a naphtha or gas condensate feed, with steam at a temperature sufficient to cause the hydrocarbons in the naphtha or gas condensate under steam cracking (steam pyrolysis) to produce olefins, such as ethylene, propene, mixed butenes, and other C4+ compounds. A cracking C4 effluent from the steam cracking system may be selectively hydrogenated to convert 1,3-butadiene to mixed butenes and then subjected to an isobutene removal unit to remove isobutene to produce a metathesis feed comprising normal butenes. The metathesis system is a dual catalyst metathesis system comprising at least a metathesis catalyst and a cracking catalyst. The metathesis feed may be passed to a metathesis system comprising the metathesis catalyst disposed in a metathesis reaction zone and the cracking catalyst disposed in a cracking reaction zone downstream of the metathesis reaction zone. The metathesis system may be operable to convert at least a portion of the normal butenes in the metathesis feed to ethylene, propene, or both. Contact of C5+ olefins produced during metathesis with the cracking catalyst may convert at least a portion of these C5+ olefins to additional ethylene, propene, or both, which may further increase the ethylene and propene yield and selectivity of the systems and processes of the present disclosure.

According to one or more aspects of the present disclosure, a process for producing olefins may include contacting a hydrocarbon feed with at least steam at a temperature of from 700° C. to 900° C. The contacting may cause at least a portion of the hydrocarbon feed to undergo steam cracking to form a cracking reaction effluent comprising at least butenes. The process may further include separating the cracking reaction effluent to produce at least a cracking C4 effluent that includes at least normal butenes, isobutene, and 1,3-butadiene. The process may further include subjecting the cracking C4 effluent to selective hydrogenation to produce a hydrogenation effluent. Selective hydrogenation may cause at least a portion of the 1,3-butadiene in the cracking C4 effluent to react to form normal butenes. The process may further include removing isobutene from the hydrogenation effluent to produce a metathesis feed comprising at least normal butenes and contacting at least a portion of the metathesis feed with a metathesis catalyst and a cracking catalyst directly downstream of the metathesis catalyst to produce a metathesis reaction effluent. Contacting the metathesis feed with the metathesis catalyst may cause metathesis of normal butenes to produce at least ethylene, propene, and C5+ olefins, and contacting with the cracking catalyst may cause at least a portion of the C5+ olefins produced through metathesis to undergo cracking reactions to produce propene, ethylene, or both. The metathesis reaction effluent may include at least ethylene, propene, or both.

According to one or more other aspects of the present disclosure, a process for producing olefins may include contacting a hydrocarbon feed with steam in a steam cracking system at a temperature sufficient to produce a cracking reaction effluent and separating the cracking reaction effluent to produce at least a cracking C4 effluent comprising normal butenes, isobutene, and 1,3-butadiene. The process may further include subjecting the cracking C4 effluent to selective hydrogenation in a selective hydrogenation unit to produce a hydrogenation effluent. Selective hydrogenation may cause at least a portion of the 1,3-butadiene in the cracking C4 effluent to react to form normal butenes. The process may further include passing the hydrogenation effluent to an isobutene removal unit, removing isobutene from the hydrogenation effluent in the isobutene removal unit to produce at least a metathesis feed comprising normal butenes, passing at least a portion of the metathesis feed to a metathesis system comprising a metathesis catalyst and a cracking catalyst directly downstream of the metathesis catalyst, and contacting the portion of the metathesis feed with the metathesis catalyst and the cracking catalyst to produce a metathesis reaction effluent. Contacting with the metathesis catalyst may cause metathesis of normal butenes in the metathesis feed to produce at least ethylene, propene, and C5+ olefins, and contacting with the cracking catalyst may cause at least a portion of the C5+ olefins produced through metathesis to undergo cracking reactions to produce ethylene, propene, or both. The metathesis reaction effluent may comprise at least ethylene, propene, or both.

According to still other aspects of the present disclosure, a system for producing olefins may include a steam cracking system that may be operable to contact a hydrocarbon feed with steam at a temperature of from 700° C. to 900° C. to produce at least a cracking C4 effluent comprising normal butenes, isobutene, and 1,3-butadiene. The system may include a selective hydrogenation unit downstream of the steam cracking system. The selective hydrogenation unit may be operable to convert 1,3-butadiene in the cracking C4 effluent from the steam cracking system to normal butenes. The system may further include an isobutene removal unit downstream of the selective hydrogenation unit and a metathesis system downstream of the isobutene removal unit. The metathesis system may comprise a metathesis reaction zone comprising a metathesis catalyst and a cracking reaction zone comprising a cracking catalyst. The cracking reaction zone may be disposed directly downstream of the metathesis reaction zone.

Additional features and advantages of the present disclosure will be set forth in the detailed description that follows, and in part will be readily apparent to those skilled in the art from that description or recognized by practicing the described subject matter, including the detailed description that follows, the claims, as well as the appended drawings.

BRIEF DESCRIPTION OF THE DRAWINGS

The following detailed description of specific aspects of the present disclosure can be best understood when read in conjunction with the following drawings, in which like structure is indicated with like reference numerals and in which.

Figure 1:
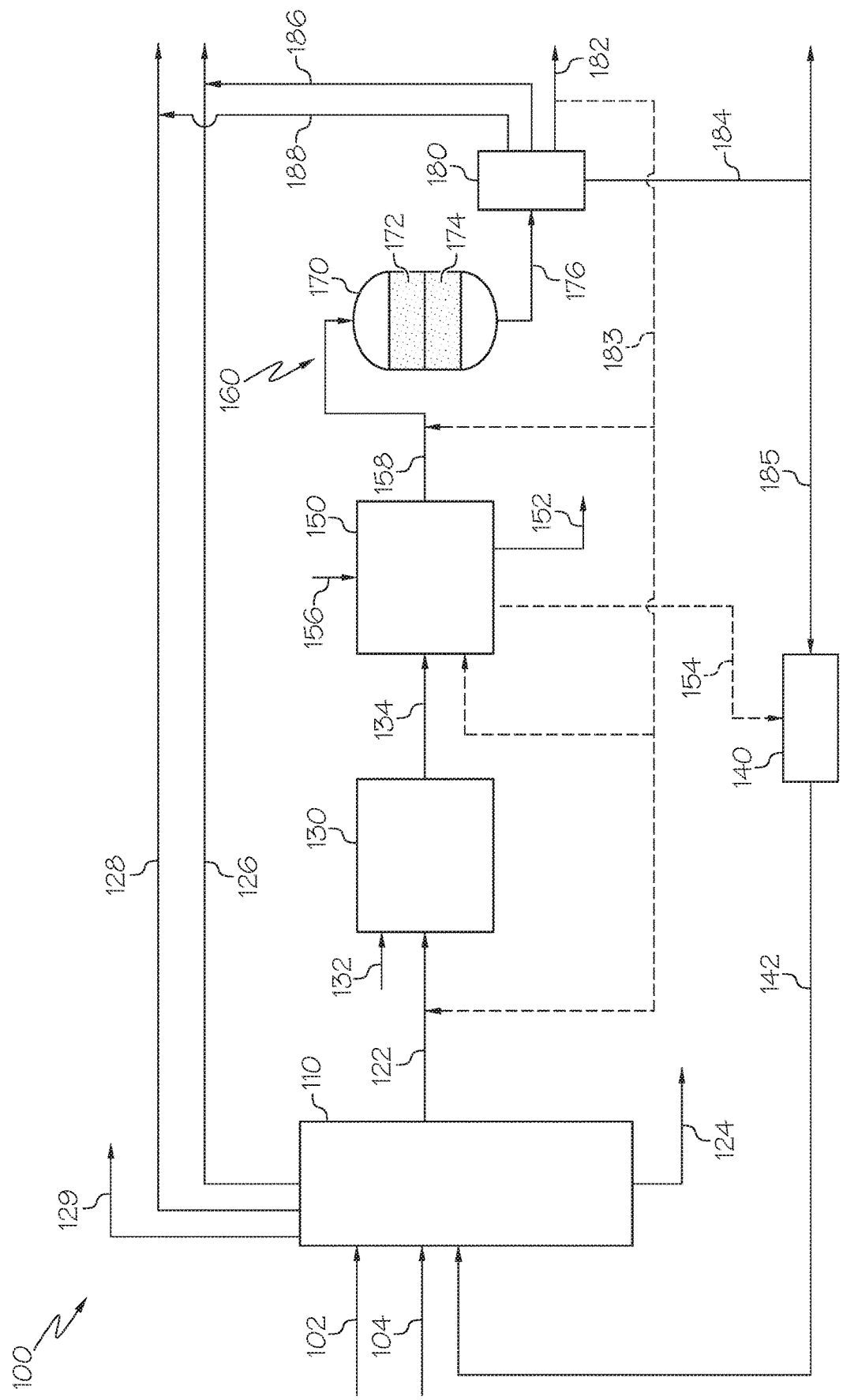
FIG. 1 schematically depicts a process flow diagram for a system for producing olefins, according to one or more embodiments shown and described in the present disclosure.

For purposes of describing the simplified schematic illustrations and descriptions in FIGS. 1-6, the numerous valves, temperature sensors, flow meters, pressure regulators, electronic controllers, pumps, heat exchangers, and the like that may be employed and well known to those of ordinary skill in the art of certain chemical processing operations may not be depicted. Further, accompanying components that are often included in typical chemical processing operations, such as valves, pipes, pumps, agitators, heat exchangers, condensers, boilers, instrumentation, internal vessel structures, or other subsystems may not be depicted. Though not depicted, it should be understood that these components are within the spirit and scope of the present embodiments disclosed. However, operational components, such as those described in the present disclosure, may be added to the embodiments described in this disclosure.

Arrows in the drawings refer to process streams. However, the arrows may equivalently refer to transfer lines, such as pipes or conduits, which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows which do not connect two or more system components may signify a product stream which exits the depicted system component or a system inlet stream which enters the depicted system or system component.

Additionally, arrows in the drawings may schematically depict process steps of transporting a stream or composition from one system component to another system component. For example, an arrow from one system component pointing to another system component may represent "passing" a stream or composition to another system component, which may include the contents of a process stream "exiting" or being "removed" from one system component and "introducing" the contents of that product stream to another system component.

Reference will now be made in greater detail to various aspects of the present disclosure, some aspects of which are illustrated in the accompanying drawings.

DETAILED DESCRIPTION

The present disclosure is directed to systems and processes for producing olefins from a hydrocarbon feed, such as a naphtha feed or a gas condensate feed. Referring to FIG. 1, one embodiment of a system 100 for producing olefins is depicted. Referring to FIG. 1, the system 100 includes a steam cracking system 110, a selective hydrogenation unit 130 disposed downstream of the steam cracking system 110, isobutene removal unit 150 disposed downstream of the selective hydrogenation unit 130, and a metathesis system 160 disposed downstream of the isobutene removal unit 150. The steam cracking system 110 may be operable to contact the hydrocarbon feed 102 with steam at reaction temperatures sufficient to conduct steam cracking of the hydrocarbon feed 102, such as temperatures from 700° C. to 900° C. The selective hydrogenation unit 130 may be operable to convert 1,3-butadiene in a cracking C4 effluent 122 from the steam cracking system 110 to normal butenes to produce a hydrogenation effluent 134. The isobutene removal unit 150 may be operable to remove isobutene from the hydrogenation effluent 134 to produce a metathesis feed 158. The metathesis system 160 may include a metathesis reaction zone 172 comprising a metathesis catalyst and a cracking reaction zone 174 comprising a cracking catalyst, the cracking reaction zone 174 disposed directly downstream of the metathesis reaction zone 172.

Figure 2:
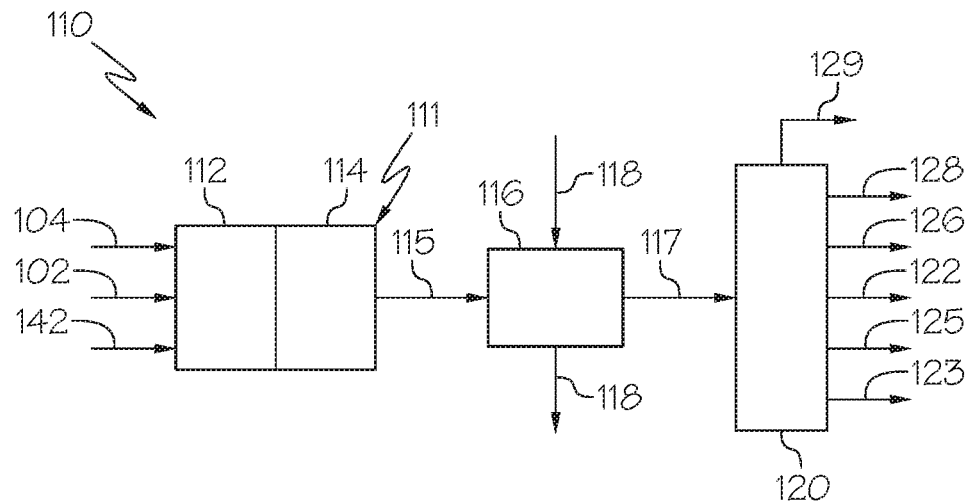
FIG. 2 schematically depicts a process flow diagram for a steam cracking system of the system for producing olefins of FIG. 1, according to one or more embodiments shown and described in the present disclosure.

Referring to FIGS. 1 and 2, processes for producing olefins using the system 100 described in the present disclosure may include contacting the hydrocarbon feed 102 with steam in the steam cracking system 110 at a temperature sufficient to produce the cracking reaction effluent 117 (FIG. 2) and separating the cracking reaction effluent 117 in the cracking effluent separation system 120 (FIG. 2) to produce at least the cracking C4 effluent 122 comprising normal butenes, isobutene, and 1,3-butadiene. The processes may further include subjecting the cracking C4 effluent 122 to selective hydrogenation in the selective hydrogenation unit 130 to produce the hydrogenation effluent 134. Selective hydrogenation may cause at least a portion of the 1,3-butadiene in the cracking C4 effluent 122 to react to form normal butenes. The processes may further include passing the hydrogenation effluent 134 to the isobutene removal unit 150 downstream of the selective hydrogenation unit 130 and removing isobutene from the hydrogenation effluent 134 in the isobutene removal unit 150 to produce a metathesis feed 158 comprising normal butenes. The processes may further include passing at least a portion of the metathesis feed 158 to the metathesis system 160 comprising the metathesis catalyst and the cracking catalyst directly downstream of the metathesis catalyst and contacting the portion of the metathesis feed 158 with the metathesis catalyst and the cracking catalyst to produce a metathesis reaction effluent 176. Contacting with the metathesis catalyst may cause metathesis of normal butenes in the metathesis feed 158 to produce at least ethylene, propene, and C5+ olefins, and contacting with the cracking catalyst may cause at least a portion of the C5+ olefins produced through metathesis to undergo cracking reactions to produce additional ethylene, propene, or both. The metathesis reaction effluent 176 may include at least ethylene, propene, or both. The systems and processes of the present disclosure may increase the yield of propene, ethylene, or both, from steam cracking of hydrocarbon feeds 102 that include naphtha and gas condensates.

The term "or", as used in the present disclosure, is inclusive; more specifically, the phrase "A or B" means "A, B, or both A and B." Exclusive "or" is designated in the present disclosure by terms such as "either A or B" and "one of A or B," for example.

The indefinite articles "a" and "an" are employed to describe elements and components of the present disclosure. The use of these articles means that one or at least one of these elements or components is present. Although these articles are conventionally employed to signify that the modified noun is a singular noun, as used herein the articles "a" and "an" also include the plural, unless otherwise stated in specific instances. Similarly, the definite article "the", as used in the present disclosure, also signifies that the modified noun may be singular or plural, again unless otherwise stated in specific instances.

As used throughout the present disclosure, the terms "upstream" and "downstream" refer to the positioning of components or units of the system 100 relative to a direction of flow of materials through the system 100. For example, a first component may be considered "upstream" of a second component if materials flowing through the system 100 encounter the first component before encountering the second component. Likewise, the second component is considered "downstream" of the first component if the materials flowing through the system 100 encounter the first component before encountering the second component.

As used in the present disclosure, reciting that a stream is passed "directly" from an upstream component to a downstream component may refer to passing the stream from the upstream component to the downstream component without passing the stream through an intervening unit operation operable to change the composition or characteristics of the stream. Intervening unit operations can include reactors and separation units but are not generally intended to include ancillary equipment, such as but not limited to heat exchangers, valves, pumps, sensors, or other process equipment required for operation of a chemical process.

As used in the present disclosure, the term "fluid" may be used to refer to a flowable composition that includes gases, liquids, or a combination of these.

As used throughout the present disclosure, a "reactor" refers to a vessel in which one or more chemical reactions may occur between one or more reactants, optionally, in the presence of one or more catalysts. For example, a reactor may include a tank or tubular reactor configured to operate as a batch reactor, a continuous stirred-tank reactor (CSTR), a plug flow reactor, a packed bed reactor, a fluidized bed reactor, continuous fluidized bed reactor, a riser reactor, downer reactor, or other type of reactor. One or more "reaction zones" may be disposed in a reactor. As used in this disclosure, a "reaction zone" may refer to a region where a particular reaction takes place in a reactor. For example, a packed bed reactor with multiple catalyst beds may have multiple reaction zones, where each reaction zone is defined by the region occupied by one of the catalyst beds. In another non-limiting example, a multi-stage catalyst reaction system may include multiple reactors, and each reactor may define a separate "reaction zone."

As used throughout the present disclosure, the terms "separation unit" and "separator" may be interchangeable and may refer to any separation device that at least partially separates one or more chemicals that are mixed in a process stream from one another. For example, a separation unit may selectively separate differing chemical species from one another, forming one or more chemical fractions. Examples of separation units include, without limitation, distillation columns, flash drums, knock-out drums, knock-out pots, centrifuges, cyclones, filtration devices, traps, scrubbers, expansion devices, adsorption units, membrane separation units, thin film evaporators, solvent extraction devices, and the like. As used throughout the present disclosure, the term "separation system" may refer to a system that includes one or a plurality of separation units, which may be operated in series, parallel, or both.

It should be understood that separation units and separation systems described in this disclosure may not completely separate all of one chemical constituent from all of another chemical constituent. It should be understood that the separation units and separation systems described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided, or separated, into two or more process streams of different compositions. A process stream passed out of a separation unit or separation system may be designated using the name of a certain compound or class of compounds present in the process stream and may be considered to include a greater proportion of that certain compound or class of compounds relative to other streams passed out of the separation unit or separation system. It is understood, however, that the other streams passed out of the separation unit or separation system may also include some amounts of the certain compound or class of compounds.

As used throughout the present disclosure, the term "residence time" may refer to the amount of time that the reactants are maintained in contact with each other or, optionally, with a catalyst at reaction conditions, such as at the reaction temperature, in a reaction system.

As used throughout the present disclosure, the term "effluent" may refer to a stream that exits a system component such as a separation unit, a reactor, or reaction zone, following a particular reaction or separation, and generally has a different composition (at least proportionally) from the stream that entered the separation unit, reactor, or reaction zone.

As used throughout the present disclosure, a "catalyst" may refer to any substance that increases the rate of a specific chemical reaction. Catalysts described in this disclosure may be utilized to promote various reactions, such as, but not limited to, cracking reactions, metathesis reactions, isomerization reactions, hydrogenation reactions, etherification reactions, or other chemical reactions.

As used in this disclosure, "cracking" may generally refer to a chemical reaction where a molecule having carbon to carbon bonds is broken into more than one molecule by the breaking of one or more of the carbon to carbon bonds, or is converted from a compound which includes a cyclic moiety, such as a cycloalkane, cycloalkene, naphthalene, an aromatic or the like, to a compound which does not include a cyclic moiety or contains fewer cyclic moieties than prior to cracking.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "steam cracking C4 effluent" passing from a first system component to a second system component should be understood to equivalently disclose the "steam cracking C4 effluent" passing from a first system component to a second system component.

As used in the present disclosure, the terms "butenes" or "mixed butenes" may be used interchangeably and may refer to combinations of one or a plurality of isobutene, 1-butene, trans-2-butene, or cis-2-butene. As used in the present disclosure, the term "normal butenes" may refer to a combination of one or a plurality of 1-butene, trans-2-butene, or cis-2-butene.

As used in the present disclosure, the term "C4" may be used to refer to compounds having 4 carbon atoms, and the term "C5+" may be used to refer to compounds having 5 or more than 5 carbon atoms.

Referring again to FIG. 1, the system 100 for producing olefins, such as but not limited to propene and ethylene, may include the steam cracking system 110, the selective hydrogenation unit 130 downstream of the steam cracking system 110, the isobutene removal unit 150 downstream of the selective hydrogenation unit 130, and the metathesis system 160 downstream of the isobutene removal unit 150. The steam cracking system 110 may be operable to contact the hydrocarbon feed 102 with steam under reaction conditions sufficient to cause at least a portion of the hydrocarbon feed 102 to undergo thermal cracking reactions to produce olefins, such as but not limited to ethylene, propene, butenes, or combinations of these.

The hydrocarbon feed 102 may include a mixture of hydrocarbon materials. The hydrocarbon materials of the hydrocarbon feed 102 may include hydrocarbons derived from crude oil. As used in this disclosure, the term "crude oil" may be understood to mean a mixture of petroleum liquids and gases, including impurities such as sulfur-containing compounds, nitrogen-containing compounds and metal compounds, as distinguished from fractions of crude oil. The hydrocarbon feed 102 may include, but may not be limited to, crude oil, vacuum residue, tar sands, bitumen, atmospheric residue, vacuum gas oils, demetalized oils, naphtha streams, gas condensate streams, or combinations of these materials. The hydrocarbon feed stream 102 may include one or a plurality of non-hydrocarbon constituents, such as one or more heavy metals, sulphur compounds, nitrogen compounds, inorganic components, or other non-hydrocarbon compounds. In embodiments, the hydrocarbon feed 102 may be pretreated to remove the non-hydrocarbon constituents and other contaminants. The hydrocarbon feed 102 may be a naphtha stream, a gas condensate stream, or a combination of these. As used in the present disclosure, the term "naphtha" may refer to an intermediate hydrocarbon composition derived from crude oil refining and having a boiling point temperature of from 35° C. to 200° C. Naphtha streams may include paraffinic, naphthenic, and aromatic hydrocarbons having from 4 to 11 carbon atoms. In embodiments, the hydrocarbon feed 102 may be a naphtha stream comprising an Arab Extra Light (AXL) feedstock.

As used in the present disclosure, the term "gas condensate" may refer to a mixture of liquid hydrocarbons having a specific gravity of from 0.5 to 0.8 and derived from raw natural gas produced from natural gas fields. Gas condensates may include paraffinic hydrocarbons having from 3 to 12 carbon atoms and lesser amounts of naphthenic and aromatic compounds compared to naphtha streams. Hydrocarbons with greater than 12 carbon atoms may also be present. The gas condensate may include at least 70 wt. %, at least 75 wt. %, or even at least 80 wt. % hydrocarbons having a boiling point temperatures less than 265° C. The gas condensates may include greater boiling hydrocarbons recovered from raw natural gas as a condensate in a natural gas processing plant. In embodiments, the gas condensate may be a Khuff gas condensate (KGC) recovered from natural gas extracted from the Khuff reservoir in Saudi Arabia. Table 1 provides boiling point profile data for Khuff gas condensate.

TABLE 1

Boiling Point Temperature Profile for Khuff Gas Condensate

| Boiling Point (BP) Temperature Range | | Weight Percent | Cummulative Weight Percent | Volume Percent |
| --- | --- | --- | --- | --- |
| Initial BP (° C.) | Final BP (° C.) | wt. % | wt. % | vol. % |
| C5 (35) | 70 | 12.9 | 12.9 | 15.36 |
| 70 | 185 | 47.32 | 60.22 | 48.15 |
| 185 | 265 | 19.9 | 80.12 | 18.79 |
| 265 | 345 | 12.14 | 92.26 | 10.99 |
| 345 | 460 | 6.87 | 99.13 | 6.04 |
| 460 | 565 | 0.29 | 99.42 | 0.25 |
| 565 | 1000 | 0.56 | 99.98 | 0.41 |

In one or more embodiments, one or more supplemental feed streams (not shown) may be added to the hydrocarbon feed 102 prior to introducing the hydrocarbon feed 102 to the steam cracking system 110 or introduced independently to the steam cracking system 110 in addition to the hydrocarbon feed 102. For example, the hydrocarbon feed 102 may include a naphtha stream, a gas condensate, or a combination of these, and a supplemental stream, such as one or a plurality of a vacuum residue, atmospheric residue, vacuum gas oils, demetalized oils, or other hydrocarbon streams, or combinations of these materials, may be combined with the hydrocarbon feed 102 upstream of the steam cracking system 110 or introduced independently to the steam cracking system 110.

Referring now to FIG. 2, the steam cracking system 110 is schematically depicted. The steam cracking system 110 may include a steam cracking reactor 111 and a cracking effluent separation system 120 disposed downstream of the steam cracking reactor 111. The steam cracking system 110 may additionally include a heat exchanger 116 disposed between the steam cracking reactor 111 and the cracking effluent separation system 120. The steam cracking reactor 111 may be operable to heat the hydrocarbon feed 102 and contact the hydrocarbon feed 102 with steam 104 at a reaction temperature sufficient to cause at least a portion of the hydrocarbons in the hydrocarbon feed 102 to undergo thermal cracking to produce a cracking reaction effluent 117 comprising olefins.

The hydrocarbon feed 102 and stream 104 may be passed directly to the steam cracking reactor 111. Other hydrocarbon containing streams, such as hydrotreated effluent 142, may also be passed to the steam cracking reactor 111, as will be described subsequently in this disclosure. The steam cracking reactor 111 may include a convection zone 112 and a pyrolysis zone 114 downstream of the convection zone 112. At least the hydrocarbon feed 102 and the steam 104 may pass into the convection zone 112. The flowrate of stream 104 passed into the convection zone 112 may be sufficient to conduct steam pyrolysis in the pyrolysis zone 114 downstream of the convection zone 112. The flowrate of stream 104 into the convection zone 112 may be sufficient to maintain a mass ratio of steam to hydrocarbons in the steam cracking reactor 111 of from 0.3:1 to 2:1. In the convection zone 112, the hydrocarbon feed 102 (and any other hydrocarbon streams passed to the convection zone 112) may be pre-heated to a pre-heat temperature. The pre-heat temperature of the convection zone 112 may be from 400 degrees Celsius (° C.) to 650° C.

The contents present in the convection zone 112 (at least the hydrocarbon feed 102 and the steam 104) may be passed to the pyrolysis zone 114 downstream of the convection zone 112. In the pyrolysis zone 114, at least the hydrocarbon feed 102 and any other hydrocarbons introduced to the steam cracking reactor 111 may be contacted with the steam 104 at reaction conditions sufficient to cause at least a portion of the hydrocarbons to undergo steam cracking (also known as steam pyrolysis) to produce a pyrolysis zone effluent 115. The pyrolysis zone 114 may operate at a temperature of from 700° C. to 900° C. The pyrolysis zone 114 may operate with a residence time of from 0.05 seconds to 2 seconds, where the residence time is the duration of time that the hydrocarbons are in contact with the steam at the reaction temperature of from 700° C. to 900° C. The mass ratio of steam 104 to hydrocarbons in the pyrolysis zone 114 may be from about 0.3:1 to about 2:1.

The pyrolysis zone effluent 115 may exit the pyrolysis zone 114 of the steam cracking reactor 111 and may be passed through a heat exchanger 116 downstream of the steam cracking reactor 111. In the heat exchanger 116, a process fluid 118, such as water, pyrolysis fuel oil, or other process stream, may cool the pyrolysis zone effluent 115 to form the cracking reaction effluent 117. The cracking reaction effluent 117 may include a mixture of cracked hydrocarbon-based materials which may be separated into one or more petrochemical products included in one or more system product streams. For example, the cracking reaction effluent 117 may include at least mixed butenes (1-butene, trans-2-butene, cis-2-butene, isobutene, or combinations of these). The cracking reaction effluent 117 may also include other olefins, such as but not limited to ethylene, propylene, 1,3-butadiene, C5+ olefins, or combinations of these; light gases, such as but not limited to methane, hydrogen, and steam; saturated hydrocarbons, such as but not limited to ethane, propane, butane, isobutane, C5+ alkanes, or combinations of these; and aromatic compounds, such as but not limited to benzene, toluene, ethylbenzene, xylenes, or other aromatic compounds.

Referring again to FIG. 2, the cracking reaction effluent 117 may be passed to the cracking effluent separation system 120. As previously discussed, the cracking reaction effluent 117 may include a mixture of cracked hydrocarbon materials. In particular, the cracking reaction effluent 117 may include at least ethylene, propene, and one or a plurality of C4 compounds, such as but not limited to mixed butenes (1-butene, trans-2 butene, cis-2-butene, isobutene). The cracking reaction effluent 117 may also include one or a plurality of fuel gas, fuel oil, pyrolysis gas, gasoline, dienes such as 1,3-butadiene or propadiene, methane, ethane, propane, butane, pentane, other C5+ hydrocarbons, light cycle oil (LCO, 216-343° C.), heavy cycle oil (HCO, >343° C.), other compounds, or combinations of these. The cracking reaction effluent 117 may also include other gases from the steam cracking reactor 111, such as steam introduced to the steam cracking reactor 111 or other gases passing through or generated in the steam cracking reactor 111. In embodiments, the cracking reaction effluent 117 may include at least fuel gas, ethylene, propene, normal butenes, isobutene, 1,3-butadiene, n-butane, fuel oil, and pyrolysis gas.

The cracking effluent separation system 120 may be fluidly coupled to the steam cracking reactor 111 such that the cracking reaction effluent 117 may be passed directly from the steam cracking reactor 111 to the cracking effluent separation system 120. The cracking effluent separation system 120 may be operable to separate the cracking reaction effluent 117 into a plurality of cracking effluent streams that include at least a cracking C4 effluent 122. The cracking effluent separation system 120 may include one or a plurality of separation units operable to separate the cracking reaction effluent 117 into a plurality of cracking effluents. Separation units may include, but are not limited to, flash drums, high-pressure separators, distillation units, fractional distillation units, condensing units, strippers, quench units, debutanizers, depropanizers, de-ethanizers, or combinations of these. In one or more embodiments, the cracking effluent separation system 120 may include a fractional distillation unit operable to separate the cracking reaction effluent 117 to produce at least the cracking C4 effluent 122. The cracking C4 effluent 122 may include one or a plurality of n-butane, isobutane, 1,3-butadiene, normal butenes (1-butene, trans-2-butene, cis-2-butene), isobutene, or combinations of these. The cracking C4 effluent 122 may also include small amounts of one or more other compounds present in the cracking reaction effluent 117. The cracking C4 effluent 122 may include at least 90%, at least 95%, at least 98%, or even at least 99% by weight of the C4 compounds from the cracking reaction effluent 117. The cracking C4 effluent 122 may include at least 90%, at least 95%, at least 98%, or even at least 99% by weight of the normal butenes from the cracking reaction effluent 117.

The cracking effluent separation system 120 may also be operable to separate the cracking reaction effluent 117 into a greater boiling temperature effluent 124 (FIG. 1), a cracking propene effluent 126, a cracking ethylene effluent 128, a lesser molecular weight gas effluent 129, or combinations of these. The greater boiling temperature effluent 124 may include constituents of the cracking reaction effluent 117 having a boiling point temperature greater than the boiling point temperatures of the constituents of the cracking C4 effluent 122. The greater boiling temperature effluent 124 may include one or a plurality of fuel oil, pyrolysis gas, gasoline, pentane, other C5+ hydrocarbons, light cycle oil (LCO, having a boiling point temperature of 216° C. to 343° C.), heavy cycle oil (HCO, having a boiling point temperature of greater than 343° C.), other compounds, or combinations of these. The greater boiling temperature effluent 124 may also include small amounts of C4 hydrocarbons not separated into the cracking C4 effluent 122. In embodiments, the greater boiling temperature effluent 124 may include at least fuel oil and pyrolysis gas. The cracking effluent separation system 120 may be further operable to separate the greater boiling temperature effluent 124 into fuel oil 123 and pyrolysis gas 125.

The cracking propene effluent 126 may include propene as a primary component. The cracking propene effluent 126 may include at least 90%, at least 95%, at least 98%, or even at least 99% by weight of the propene from the cracking reaction effluent 117. The cracking ethylene effluent 128 may include ethylene as a primary component. The cracking ethylene effluent 128 may include at least 90%, at least 95%, at least 98%, or even at least 99% by weight of the ethylene from the cracking reaction effluent 117. The lesser molecular weight gas effluent 129 may include other lesser boiling gases from the cracking reaction effluent 117, such as but not limited to fuel gases such as methane and hydrogen; inert gases such as nitrogen; or other gases having a boiling point temperature less than the boiling point temperatures of ethylene and propene. One or a plurality of the greater boiling temperature effluent 124, fuel oil 123, pyrolysis gas 125, cracking propene effluent 126, cracking ethylene effluent 128, lesser molecular weight gas effluent 129, or combinations of these may be passed to one or more additional downstream unit operations for further processing. Steam may also be recovered from the cracking reaction effluent 117.

Referring again to FIG. 1, the cracking C4 effluent 122 may be passed to the selective hydrogenation unit 130 disposed downstream of the steam cracking system 110. The selective hydrogenation unit 130 may be fluidly coupled to an outlet of the cracking effluent separation system 120 so that the cracking C4 effluent 122 can be passed directly from the cracking effluent separation system 120 to the selective hydrogenation unit 130. As previously discussed, the cracking C4 effluent 122 may include 1,3-butadiene, which may produce unwanted metathesis products when contacted with the metathesis catalyst in the metathesis system 160 downstream of the steam cracking system 110. In embodiments, the cracking C4 effluent 122 may include up to 60 wt. % 1,3-butadiene, such as from 1 wt. % to 60 wt. %, or from 10 wt. % to 50 wt. % 1,3-butadiene, based on the total weight of the cracking C4 effluent 122.

The selective hydrogenation unit 130 may be a selective butadiene hydrogenation unit operable to react at least a portion of the 1,3-butadiene in the cracking C4 effluent 122 to form normal butenes, such as 1-butene, trans-2-butene, cis-2-butene, or combinations of these. Converting the 1,3-butadiene to normal butenes may increase the yield of propene and ethylene from the system 100 by providing a greater amount of normal butenes for metathesis to propene and ethylene in the metathesis system 160 downstream of the selective hydrogenation unit 130. The selective hydrogenation unit 130 may be selective for hydrogenating 1,3-butadiene relative to hydrogenation of normal butenes so that the 1,3-butadiene can be hydrogenated to normal butenes without further hydrogenation of the normal butenes produced to n-butane or substantial hydrogenation of the normal butenes from the cracking C4 effluent 122 to n-butane. The selective hydrogenation unit may be operable to convert greater than or equal to 90% by weight, greater than or equal to 93% by weight, or even greater than or equal to 95% by weight of the 1,3-butadiene present in the cracking C4 effluent 122 to 1-butene and 2-butene. The selectivity for 1-butene and 2-butene can be tuned by carbon monoxide injection as further discussed subsequently in the present disclosure.

The selective hydrogenation unit 130 may include one or a plurality of hydrogenation reactors, such as 1, 2, 3, or more than 3 hydrogenation reactors. When the selective hydrogenation unit 130 includes a plurality of hydrogenation reactors, the hydrogenation reactors may be operated in series or in parallel. In embodiments, the selective hydrogenation unit 130 may include two or more hydrogenation reactors to achieve more than 99% conversion of 1,3-butadiene. Each of the hydrogenation reactors of the selective hydrogenation unit 130 may include at least one hydrogenation reaction zone comprising a selective hydrogenation catalyst. Each of the hydrogenation reactors of the selective hydrogenation unit 130 may be a fixed bed reactor comprising the selective hydrogenation catalyst.

The selective hydrogenation catalyst may include a catalytic metal supported on an alumina catalyst support. The catalytic metal may include one or more metals in Groups 8-11 of the International Union of Pure and Applied Chemistry (IUPAC) periodic table of elements (IUPAC periodic table). For example, the catalytic metal of the selective hydrogenation catalyst may include one or more of platinum, rhodium, palladium, ruthenium, cobalt, nickel, copper, or combinations of these metals. The selective hydrogenation catalyst may include from 0.3 wt. % to 0.5 wt. % catalytic metal based on the total weight of the selective hydrogenation catalyst.

Referring again to FIG. 1, in operation, the cracking C4 effluent 122 may be passed to the selective hydrogenation unit 130, in which the cracking C4 effluent 122 may be contacted with hydrogen in the presence of the selective hydrogenation catalyst. The hydrogen may be provided by hydrogen stream 132, which may be introduced to one or more of the hydrogenation reactors of the selective hydrogenation unit 130 or combined with the cracking C4 effluent 122 upstream of the selective hydrogenation unit 130. The cracking C4 effluent 122 may be contacted with hydrogen in the presence of the selective hydrogenation catalyst at a hydrogenation reaction temperature of from 50° C. to 100° C. and a hydrogenation reaction pressure of from 965 kilopascals (kPa) to 2758 kPa, such as from 1500 kPa to 2500 kPa. The hydrogenation reactors of the selective hydrogenation unit 130 may be operated at a weight hourly space velocity (WHSV) of from 2 per hour to 4 per hour.

Contacting the cracking C4 effluent 122 with hydrogen in the presence of the selective hydrogenation catalyst may cause at least a portion of the 1,3-butadiene to undergo selective hydrogenation to produce a hydrogenation effluent 134. The hydrogenation effluent 134 may have a concentration of 1,3-butadiene less than a concentration of 1,3-butadiene in the cracking C4 effluent 122. In embodiments, the hydrogenation effluent 134 may have a greater concentration of one or more of 1-butene, trans-2-butene, or cis-2-butene compared to the concentration of these constituents in the cracking C4 effluent 122. The conversion rate of 1,3-butadiene to normal butenes may be greater than or equal to 90% by weight of the 1,3-butadiene in the cracking C4 effluent 122, such as greater than or equal to 93%, greater than or equal to 94%, or even greater than or equal to 95% by weight of the 1,3-butadiene from the cracking C4 effluent 122.

In embodiments, the selective hydrogenation unit 130 can include three reactor stages, such as three hydrogenation reactors, in series. The first two hydrogenation reactors can convert the 1,3-butadiene present in the cracking C4 effluent 122 to 1-butene, cis-2-butene, trans-2-butene, or combinations of these. The first two hydrogenation reactors can include the selective hydrogenation catalyst, such as palladium supported on alumina. The selective hydrogenation catalyst can be the same for the first two hydrogenation reactors. The hydrogen stream 132 can be combined with the cracking C4 effluent 122 upstream of the first hydrogenation reactor of the selective hydrogenation unit 130. The third hydrogenation reactor may also include a selective hydrogenation catalyst, which may be the same as or different from the selective hydrogenation catalyst in the first two hydrogenation reactors. The hydrogenation effluent 134 may be passed out of the selective hydrogenation unit 130 to downstream operations, such as the isobutene removal unit 150.

As previously discussed, the cracking C4 effluent 112 from the steam cracking system 110 may include isobutene, which may have a negative impact on the propene selectivity and yield of the system 100. Isobutene may undergo cross-metathesis with 1-butene or 2-butene. Cross-metathesis between isobutene and 2-butene produces propene and 2-methyl-2-butene, which is productive for producing propene. However, cross-metathesis between isobutene and 1-butene produces ethylene and 2-methy-2-pentene with no propene produced. Therefore, the presence of isobutene in the metathesis feed 142 may operate to reduce the selectivity and yield of propene from the system 100.

Referring again to FIG. 1, to increase the selectivity and yield of propene, the system 100 may include the isobutene removal unit 150 disposed downstream of the selective hydrogenation unit 130. The isobutene removal unit 150 may be disposed between the selective hydrogenation unit 130 and the metathesis system 160 such that the isobutene removal unit 150 is downstream of the selective hydrogenation unit 130 and the metathesis system 160 is downstream of the isobutene removal unit 150. The hydrogenation effluent 134 may be passed directly from the selective hydrogenation unit 130 to the isobutene removal unit 150. The isobutene removal unit 150 may be operable to receive the hydrogenation effluent 134 from the selective hydrogenation unit 130 and remove isobutene from the hydrogenation effluent 134 to produce the metathesis feed 158, which may have a decreased concentration of isobutene compared to the hydrogenation effluent 134.

Figure 3:
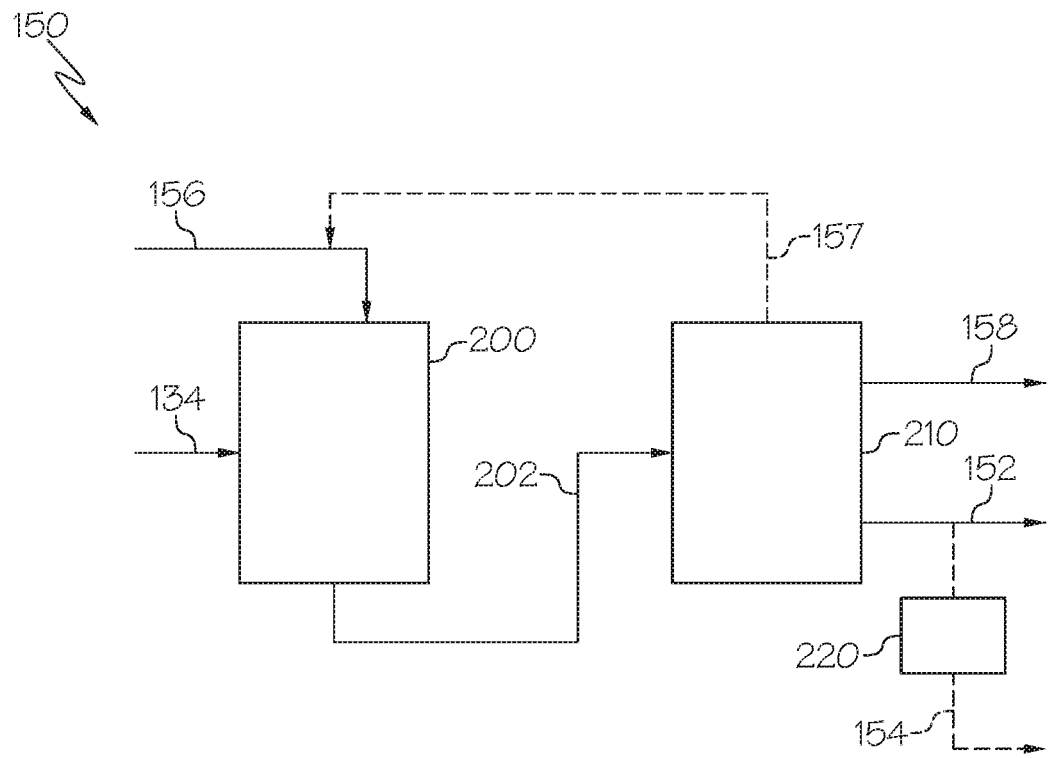
FIG. 3 schematically depicts a process flow diagram of an isobutene removal unit of the system of FIG. 1, according to one or more embodiments shown and described in the present disclosure.

Referring to FIG. 3, the isobutene removal unit 150 may include a methyl-tert-butyl ether reactor 200 (MTBE reactor 200), which may be operable to convert at least a portion of the isobutene to methyl-tert-butyl ether (MTBE). The isobutene removal unit 150 may also include an MTBE separation system 210 disposed downstream of the MTBE reactor 200. MTBE reactor 200 may include a cation exchange resin or an acid catalyst. The MTBE reactor 200 may be operable to contact the hydrogenation effluent 134 and methanol from a methanol feed 156 in the presence of the cation exchange resin or acid catalyst at reaction conditions sufficient to convert at least a portion of the isobutene in the hydrogenation effluent 134 to MTBE. The MTBE reactor 200 may be maintained at a temperature of from 35° C. to 100° C. Contacting the hydrogenation effluent 134 with the methanol in the presence of the cation exchange resin or acid catalyst in the MTBE reactor 200 may cause at least a portion of the isobutene in the hydrogenation effluent 134 to undergo etherification to produce MTBE.

An MTBE reactor effluent 202, which may include at least the MTBE, excess methanol, and the unreacted constituents of the hydrogenation effluent 134, may be passed to the MTBE separation system 210 downstream of the MTBE reactor 200. The MTBE reactor effluent 202 may include a concentration of isobutene less than the concentration of isobutene in the hydrogenation effluent 134. The MTBE separation system 210 may include one or a plurality of separation units operable to separate the MTBE reactor effluent 202 into at least the metathesis feed 158 and an MTBE effluent 152. The metathesis feed 158 and the MTBE effluent 152 may comprise at least 95 percent by weight of the constituents of the MTBE reactor effluent 202. The MTBE effluent 152 may include at least 80%, at least 90%, at least 95%, or even at least 98% of the MTBE produced in the MTBE reactor 200. The metathesis feed 158 may include at least 90%, at least 95%, at least 98%, or even at least 99% of the normal butenes from the hydrogenation effluent 134. In embodiments, the MTBE separation system 210 may be operable to produce a methanol effluent 157 comprising at least a portion of the excess methanol from the MTBE reaction, which may be recycled back to the MTBE reactor 200. Referring again to FIG. 1, the metathesis feed 158 may be passed to the metathesis system 160 disposed downstream of the isobutene removal unit 150. The MTBE effluent 152 may be passed out of the system 100 to one or more downstream unit operations for further processing. The MTBE from the MTBE effluent 152 may be recovered and sold as a product or as an intermediate chemical for use in chemical processing operations.

Referring again to FIG. 3, in embodiments, the isobutene removal unit 150 may include an MTBE catalytic cracking unit 220 disposed downstream of the MTBE separation system 210. The MTBE catalytic cracking unit 220 may be operable to receive at least a portion of the MTBE effluent 152 and contact the portion of the MTBE effluent 152 with a cracking catalyst under conditions sufficient to convert the MTBE back into isobutene. The MTBE catalytic cracking unit 220 may be a fixed bed reactor comprising an MTBE cracking reaction zone that includes the cracking catalyst. The cracking catalyst may be any catalyst capable of catalyzing the cracking of MTBE back to isobutene. The cracking catalyst may be a zeolite. In embodiments, the cracking catalyst may be a structured zeolite, such as MFI or BEA structured zeolite, for example. The cracking catalyst may be an MCM-41 catalyst or an SBA-15 catalyst. In embodiments, the cracking catalyst may be an MFI structured silica-containing catalyst. Contacting the portion of the MTBE effluent 152 with the cracking catalyst in the MTBE catalytic cracking unit 220 may cause the MTBE in the MTBE effluent 152 to undergo catalytic cracking to produce an isobutene effluent 154.

Referring again to FIG. 1, the isobutene effluent 154 may be passed to a hydrotreating unit 140, in which the isobutene in the isobutene effluent 154 may be saturated before being passed back to the steam cracking system 110 as part of the hydrotreated effluent 142. The hydrotreating unit 140 and operation of the hydrotreating unit 140 to saturate isobutene and C5+ olefins from the metathesis system 160 will be discussed in further detail subsequently in this disclosure. Thus, cracking at least a portion of the MTBE effluent 152 back to isobutene, saturating the isobutene effluent 154 in the hydrotreating unit 140, and passing the resulting hydrocarbon compounds back to the steam cracking system 110 may increase the overall conversion and propene selectivity and yield of the system 100 compared to removing all of the MTBE effluent 152 from the system 100.

Referring again to FIG. 1, the system 100 includes the metathesis system 160 disposed downstream of the isobutene removal unit 150. The metathesis system 160 may be operable to contact the metathesis feed 158 with at least a metathesis catalyst in a metathesis reactor 170 to produce a metathesis reaction effluent 176 comprising one or more olefins, such as but not limited to ethylene, propene, pentene, or combinations of these. The metathesis system 160 may be operable to contact the metathesis feed 158 with a multiple catalyst system comprising a metathesis catalyst and a cracking catalyst downstream of the metathesis catalyst to produce the metathesis reaction effluent. The metathesis system 160 may also be operable to separate the metathesis reaction effluent 176 into one or more metathesis effluent streams.

Referring again to FIG. 1, the metathesis system 160 may include at least one metathesis reactor 170 and a metathesis effluent separation system 180 downstream of the metathesis reactor 170. In embodiments, the metathesis system 160 may also include a metathesis feed treatment unit (not shown), which may be operable to remove impurities from the metathesis feed 158. The metathesis feed treatment unit may include one or more catalysts and may remove impurities such as, but not limited to, butadiene and other dienes, oxygenates such as carbonyls and alcohols, sulfur compounds, water, other impurities, or combinations of these.

Figure 5:
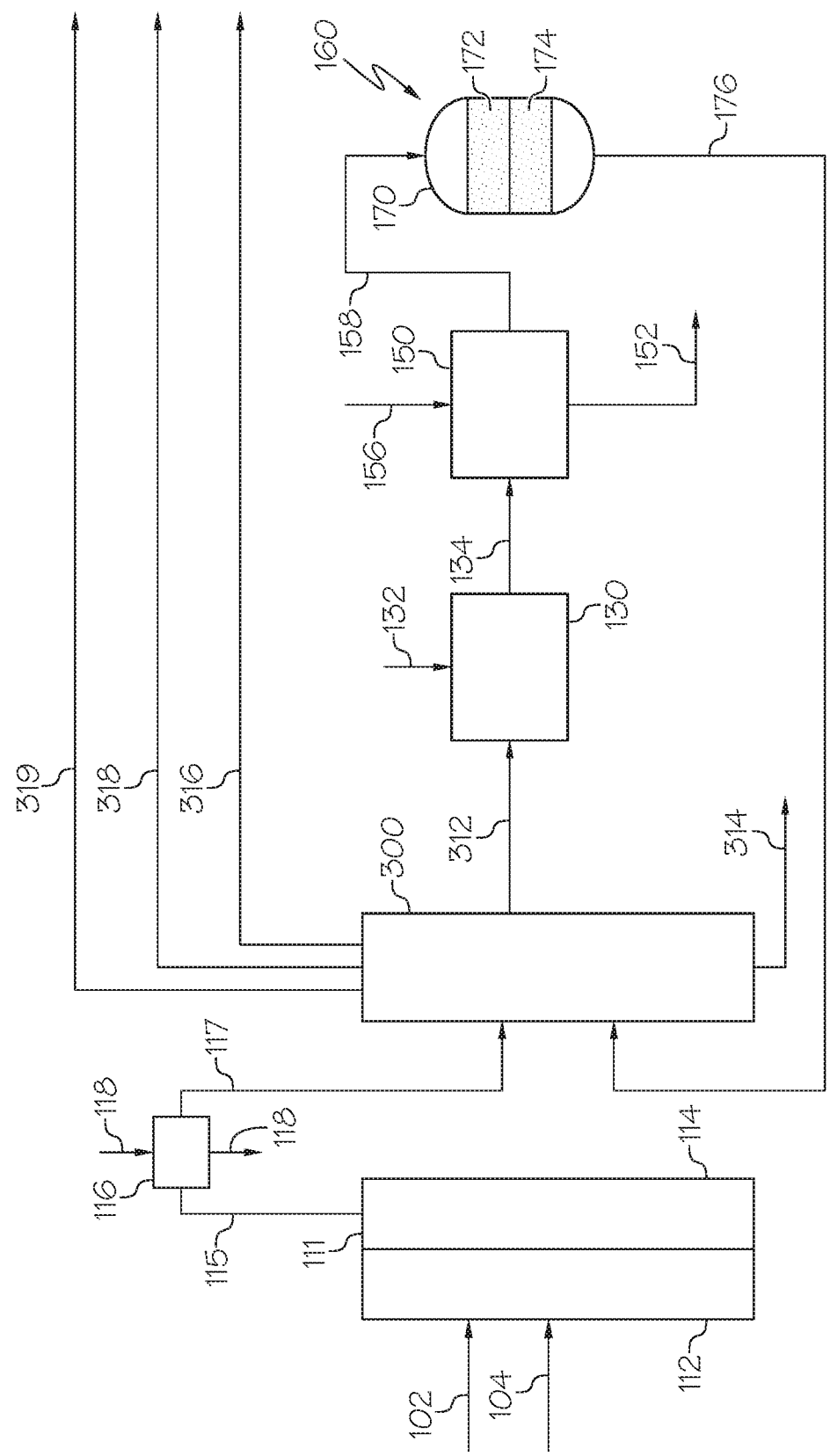
FIG. 5 schematically depicts a process flow diagram of still another system for producing olefins, according to one or more embodiments shown and described in the present disclosure.

The metathesis reactor 170 may be operable to receive the metathesis feed 158 (treated or not treated) and contact the metathesis feed 158 with at least the metathesis catalyst. Contacting the metathesis feed 158 with the metathesis catalyst may cause at least a portion of the mixed butenes from the metathesis feed 158 to undergo at least a metathesis reaction to produce a metathesis reaction effluent 176 that includes one or more metathesis reaction products. The metathesis reactor 170 may also be operable to contact the metathesis feed 158 with the metathesis catalyst and a cracking catalyst downstream of the metathesis catalyst. The metathesis effluent separation system 180 may be operable to receive the metathesis reaction effluent 176 from the metathesis reactor 170 and separate the metathesis reaction effluent 176 into one or a plurality of metathesis effluent streams. Alternatively, the metathesis reaction effluent 176 and the cracking reaction effluent 117 may be passed to a single separation system, such as but not limited to a combined separation system 300 (FIG. 5).

As used throughout the present disclosure, "metathesis" refers to an organic reaction that involves the redistribution of fragments of alkenes by the scission and regeneration of carbon-carbon double bonds. As used throughout the present disclosure, a "metathesis catalyst" may refer to a catalyst that promotes the metathesis reaction of alkenes to form other alkenes. Contact of butenes with a metathesis catalyst may result in conversion of 2-butene to 1-butene or conversion of 1-butene to 2-butene through "self-metathesis," which is shown in Chemical Reaction 1 (RXN 1). Self-metathesis of 2-butene to 1-butene and 1-butene to 2-butene by the metathesis catalyst may be an equilibrium reaction as denoted by the bi-directional arrows with single heads in RXN 1.

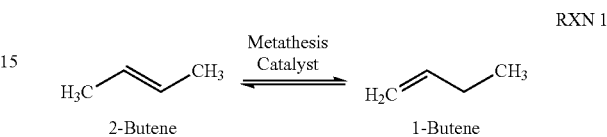

RXN 1

Contact of a mixture of normal butenes (1-butene, trans-2-butene, cis-2-butene, or combinations of these) with the metathesis catalyst may also result in cross-metathesis of 1-butene and 2-butene. As used in the present disclosure, the term "2-butene" may refer to trans-2-butene, cis-2-butene, or a mixture of these. Cross-metathesis between 1-butene and 2-butene may be achieved with the metathesis catalyst as shown in Chemical Reaction 2 (RXN 2). In the case of cross-metathesis of 2-butene and 1-butene, the redistribution of these carbon-carbon double bonds through metathesis may produce propene and $C_5$-$C_6$ olefins.

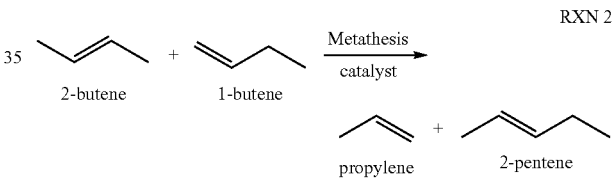

RXN 2

Further, as shown in the following Chemical Reaction 3 (RXN 3), "catalytic cracking" may refer to catalytic conversion of $C_4$-$C_6$ alkenes to propene and other alkanes, alkenes, or alkanes and alkenes, for example, $C_1$-$C_2$ alkenes (propene, ethylene, or both). Catalytic conversion of C4-C6 alkenes to propene and other alkanes, alkenes, or alkanes and alkenes may further increase the yield of propene and ethylene from the metathesis system 160.

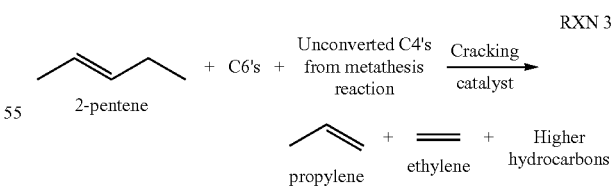

RXN 3

Referring to Chemical Reactions RXN 1-RXN 3, the metathesis and cracking reactions are not limited to these reactants and products; however, Chemical Reactions RXN 1-RXN 3 provide a simplified illustration of the reaction methodology.

The metathesis feed 158 passed to the metathesis system 160 may be any composition or stream comprising butenes, such as 1-butene, cis-2-butene, trans-2-butene, or combinations of these isomers of butene. The metathesis feed 158 may also include other C4 hydrocarbons, such as n-butane, iso-butane, or combinations of these. The metathesis feed 158 may also include any 1,3-butadiene or isobutene not reacted in the selective hydrogenation unit 130 or the isobutene removal unit 150, respectively. The metathesis feed 158 may include at least a portion of the cracking C4 effluent 122 from the steam cracking system 110. In embodiments, the metathesis feed 158 may be passed directly from the isobutene removal unit 150, such as the MTBE separation system 210, to the metathesis system 160.

The metathesis feed 158 may include from 10 weight percent (wt. %) to 70 wt. %, from 10 wt. % to 60 wt. %, from 10 wt. % to 50 wt. %, from 20 wt. % to 70 wt. %, from 20 wt. % to 60 wt. %, or from 20 wt. % to 50 wt. % 2-butene based on the total weight of the metathesis feed 158. The metathesis feed 158 may include from 5 wt. % to 70 wt. %, from 5 wt. % to 60 wt. %, from 10 wt. % to 70 wt. %, from 10 wt. % to 60 w. %, from 10 wt. % to 50 wt. %, from 15 wt. % to 70 wt. %, from 15 wt. % to 60 wt. %, or from 15 wt. % to 50 wt. % 1-butene based on the total weight of the metathesis feed 158. The metathesis feed 158 may include from 5 wt. % to 30 wt. % or 10 wt. % to 25 wt. % n-butane based on the total weight of the metathesis feed 158. The metathesis feed 158 may include at least 90%, at least 95%, at least 98%, or even at least 99% of the normal butenes from the cracking reaction effluent 117.

In embodiments, the metathesis feed 158 may be substantially free of ethylene. As used in the present disclosure, the term "substantially free" of a component means less than 1 weight percent (wt. %) of that component in a particular portion of a catalyst, stream, or reaction zone. As a non-limiting example, a metathesis feed 158 that is substantially free of ethylene, may have less than 1 wt. % of ethylene based on the total weight of the metathesis feed 158. The metathesis feed 158 may be substantially free of propene. In embodiments, the metathesis feed 158 may be substantially free of isobutene. In embodiments, the metathesis feed 158 may have less than 1.0 wt. % isobutene, or even less than 0.1 wt. % of isobutene, based on the total weight of the metathesis feed 158. In embodiments, the metathesis feed 158 may be substantially free of 1,3-butadiene. In embodiments, the metathesis feed 158 may have less than 1 wt. %, or even less than 0.1 wt. % 1,3-butadiene based on the total weight of the metathesis feed 158.

Referring again to FIG. 1, the metathesis reactor 170 may include one or a plurality of reaction zones, such as but not limited to, a metathesis reaction zone 172, a cracking reaction zone 174, or a combination of both. The metathesis reactor 170 may include at least one fixed bed reactor operated in an upflow or a downflow configuration. Although depicted as a fixed bed reactor, the metathesis reactor 170 may be any other type of reactor suitable for conducting a metathesis reaction. In one or more embodiments, the metathesis reactor 170 may include a plurality of metathesis reactors operated in series or in parallel. The metathesis reactor 170 may include a plurality of catalyst beds, where each of the catalyst beds may be a separate reaction zone. Two or more of the plurality of catalyst beds or reaction zones may be disposed in a single reactor. In embodiments, metathesis reactor 170 may include a single reactor having the metathesis reaction zone 172 comprising the metathesis catalyst and the cracking reaction zone 174 comprising the cracking catalyst and disposed downstream of the metathesis reaction zone 172.

In embodiments, the metathesis reactor 170 may include a plurality of catalyst beds or reaction zones where at least one of the catalyst beds or reaction zones is disposed in a separate reactor from the other of the plurality of catalyst beds or reactions zones. For example, the metathesis reactor 170 may include a first reactor (not shown) comprising the metathesis reaction zone 172 having the metathesis catalyst and a second reactor (not shown) disposed downstream of the first reactor and comprising the cracking reaction zone 174 that includes the cracking catalyst. The first reactor and the second reactor may be fluidly coupled by a conduit extending directly from the first reactor to the second reactor. The conduit may fluidly couple the first reactor and the second reactor in series.

The metathesis reactor 170 may be operable to contact the metathesis feed 158 with one or a plurality of catalysts, such as but not limited to the metathesis catalyst, the cracking catalyst, or both. In embodiments, the metathesis reactor 170 may include the metathesis reaction zone 172 and the cracking reaction zone 174 downstream of the metathesis reaction zone 172. The metathesis reaction zone 172 may include the metathesis catalyst, and the cracking reaction zone 174 may include the cracking catalyst. The metathesis feed 158 introduced to the metathesis reactor 170 may encounter the metathesis catalyst in the metathesis reaction zone 172 before encountering the cracking catalyst in the cracking reaction zone 174.

Contacting of the metathesis feed 158 with the metathesis catalyst may cause at least a portion of the butene in the metathesis feed 158 to undergo a metathesis reaction to produce olefins, such as ethylene, propene, or both. The metathesis catalyst may be any catalyst operable to promote cross-metathesis of butenes to produce propene. The metathesis catalyst may be a particulate catalyst that includes a metal oxide disposed on the surfaces of a catalyst support material. The catalyst support material may be mesoporous silica catalyst support or a mesoporous silica-alumina catalyst support, such as but not limited to one or more molecular sieves or zeolites. As used in the present disclosure, "mesoporous" refers to a material having an average pore size of greater than 2 nanometers and less than 50 nanometers. The mesoporous silica catalyst support may include alumina or may be substantially free of alumina. As a non-limiting example, a mesoporous silica catalyst support that is substantially free of alumina may have less than 1 wt. % alumina.

The metathesis catalyst may include one or a plurality of metal oxides incorporated into the catalyst support material or deposited onto the surfaces of the catalyst support material. The metal oxide may include one or more oxides of a metal from Groups 6-10 of the IUPAC periodic table. As non-limiting examples, the metal oxide may include one or more oxides of molybdenum, rhenium, tungsten, or any combination of these. In one or more embodiments, the metal oxide of the metathesis catalyst may be tungsten oxide ($WO_3$). It is contemplated that various amounts of the metal oxide may be impregnated into the mesoporous silica catalyst support. For example and not by way of limitation, the weight percentage (wt. %) of metal oxide, for example $WO_3$, in the metathesis catalyst may be from 1 wt. % to 30 wt. %, such as from 5 wt. % to 25 wt. %, or even from 8 wt. % to 20 wt. % based on the total weight of the metathesis catalyst. The metal oxides may be incorporated into the catalyst support material through co-precipitation, methods, sol-gel methods, or other methods. Alternatively or additionally, the metal oxide may be deposited onto the outer surfaces and pore surfaces of the catalyst support material through any type of impregnation or deposition process, such as but not limited to wet impregnation, vapor deposition, or other suitable method. The amount of metal oxide impregnated onto the catalyst support material of the metathesis catalyst may be verified using inductively coupled plasma (ICP) mass spectrometer or an x-ray fluorescence (XRF) spectrometer to determine the amount of tungsten in a sample of the mesoporous silica catalyst support impregnated with tungsten oxide.

The average pore size of the metathesis catalyst may be obtained from the average surface area and pore size distribution, which are determined using the Brunauer-Emmett-Teller (BET) method according to standard test methods known in the art. Average pore size is generally determined as a pore diameter or pore radius based on the assumption of cylindrical shaped pores. However, it is understood that metathesis catalysts described in this disclosure may have actual shapes that are cylindrical or other shapes, such as, but not limited to, conical, square, slit-shaped, or other irregular shaped pores or combinations of these. The metathesis catalyst may have a relative pore volume per weight of material of at least 0.6 cubic centimeters per gram ($cm^3/g$), such as from 0.6 $cm^3/g$ to 2.5 $cm^3/g$ or even from 0.7 $cm^3/g$ to 1.5 $cm^3/g$. The metathesis catalyst may have a surface area per unit weight of the metathesis catalyst of from 200 meters squared per gram ($m^2/g$) to 600 $m^2/g$, such as from 225 $m^2/g$ to 350 $m^2/g$, or even from from 250 $m^2/g$ to 325 $m^2/g$. The metathesis catalyst may have a mean particle size of from 20 nanometers (nm) to 200 nm, such as from 50 nm to 150 nm. The metathesis catalyst may have a mean particle size distribution of from 100 angstroms (Å) to 300 Å. The mean particle size and mean particle size distribution can be measured using a particle size analyzer, such as a Nanopartica™ series particle size analyzer from Horiba Scientific Company, which measures the size of single particles dispersed in water using ultraviolet (UV) light.

The metathesis catalyst may have a total acidity from 0.001 millimole/gram (mmol/g) to 0.5 mmol/g, from 0.01 mmol/g to 0.5 mmol/g, from 0.1 mmol/g to 0.5 mmol/g, from 0.3 mmol/g to 0.5 mmol/g, from 0.4 mmol/g to 0.5 mmol/g, from 0.001 mmol/g to 4 mmol/g, or from 0.001 mmol/g to 0.3 mmol/g. The acidity of the metathesis catalyst may be generally maintained at or less than 0.5 mmol/g to produce a greater propene selectivity for the multiple-stage catalyst system and to reduce production of byproducts, such as aromatics. Increasing acidity may increase the overall butene conversion; however, this increased conversion may lead to decreased propene selectivity and increased production of aromatic byproducts, which may lead to catalyst coking and deactivation.

Contact of the metathesis feed 158 with the metathesis catalyst in the metathesis reaction zone 172 may produce a metathesis reaction zone product that may include propene and other alkanes and alkenes, such as ethylene and C5+ olefins, for example. The metathesis reaction zone product may also include unreacted butenes, such as cis-2-butene, trans-2-butene, 1-butene, or combinations of two or more of these butenes. The metathesis catalyst may also promote self-metathesis of 2-butene to 1-butene, or 1-butene to 2-butene, in the metathesis reaction zone 172.

Referring again to FIG. 1, the metathesis reaction zone product may pass into contact with the cracking catalyst in the cracking reaction zone 174 downstream of the metathesis reaction zone 172. The cracking reaction zone 174 may include the cracking catalyst capable of converting at least a portion of the unreacted normal butenes and the produced C5+ olefins in the metathesis reaction zone product stream, to lighter olefins, such as ethylene and propene. Contact of the metathesis reaction zone product with the cracking catalyst in the cracking reaction zone 174 may cause at least a portion of the C5+ olefins produced in the metathesis reaction zone 172 to undergo catalytic cracking to produce at least ethylene, propene, or combinations of these.

The cracking catalyst may be any catalyst capable of catalyzing the cracking of C5+ olefins to produce additional propene, ethylene, or both. The cracking catalyst may be a zeolite. In embodiments, the cracking catalyst may be a structured zeolite, such as MFI or BEA structured zeolite, for example. The cracking catalyst may be an MCM-41 catalyst or an SBA-15 catalyst. The cracking catalyst may be an MFI structured silica-containing catalyst. For example, the MFI structured silica-containing catalyst may include MFI structured aluminosilicate zeolite catalysts or MFI structured silica catalysts that do not contain alumina or are substantially free of alumina, such as having less than 0.01 wt. % alumina based on the total weight of the catalyst. The cracking catalyst may be a MFI structured silica-containing catalyst may include other impregnated metal oxides in addition to or as an alternative to alumina. The cracking catalyst may include one or more of metal oxides of metals from Groups 6-10 of the IUPAC Periodic Table, more specifically, metal oxides of molybdenum, rhenium, tungsten, titanium, or combinations of these. It should be understood that the cracking catalyst may include a combination of multiple zeolites, such as zeolite particles which include multiple types of zeolites, or a mixture of zeolite particles where particles include different zeolites. The cracking catalyst may be an MFI structured aluminosilicate zeolite catalyst may have a molar ratio of silica to alumina of from 5 to 5000. Various suitable commercial embodiments of cracking catalyst comprising MFI structured aluminosilicate zeolites are contemplated, for example, ZSM-5 zeolites such as MFI-280 produced by Zeolyst International or MFI-2000 produced by Saudi Aramco. Various suitable commercial embodiments are also contemplated for the alumina free MFI structured silica-containing catalysts. One such example is Silicalite-1 produced by Saudi Aramco.

The cracking catalyst may have an average pore size of from 1.5 nm to 3 nm, or from 1.5 nm to 2.5 nm. The cracking catalyst may have an average relative pore volume per weight of material of from 0.1 $cm^3/g$ to 0.3 $cm^3/g$, or from 0.15 $cm^3/g$ to 0.25 $cm^3/g$. The cracking catalyst may have an average surface area of from 300 $m^2/g$ to 425 $m^2/g$, or from 340 $m^2/g$ to 410 $m^2/g$. The cracking catalyst may have an individual crystal size of from 10 microns to 40 microns, from 15 microns to 40 microns, or from 20 microns to 30 microns. The cracking catalyst may have a total acidity of from 0.001 mmol/g to 0.1 mmol/g, or from 0.01 mmol/g to 0.08 mmol/g. The acidity may be maintained at or less than 0.1 mmol/g to reduce production of byproducts, such as aromatic compounds. Increasing acidity may increase the amount of cracking; however, this increased cracking may also lead to less selectivity and increased production of aromatic hydrocarbon byproducts, which may lead to catalyst coking and deactivation. In some cases, the cracking catalyst may be modified with an acidity modifier to adjust the level of acidity in the cracking catalyst. Examples of acidity modifiers may include, but are not limited to, rare earth modifiers, phosphorus modifiers, potassium modifiers, or combinations of each. Alternatively, the cracking catalysts may be substantially free of acidity modifiers, such as those selected from rare earth modifiers, phosphorus modifiers, potassium modifiers, or combinations of each.

The metathesis reactor 170 may optionally include an isomerization zone (not shown) having an isomerization catalyst. The isomerization zone may be disposed upstream of the metathesis reaction zones 172 and the cracking reaction zone 174. In embodiments, the isomerization zone may be in a separate reactor upstream of the metathesis reactor 170 and fluidly coupled to the metathesis reactor 170 such that the isomerization reaction products pass directly from the isomerization reaction zone to the metathesis reaction zone 172. In some embodiments, the isomerization reaction zone may be disposed within the metathesis reactor 170 and upstream of the metathesis reaction zone 172. The isomerization catalyst may be any catalyst that may promote equilibration of the isomerization reaction of 2-butene in the metathesis feed 158 to 1-butene. In embodiments, the isomerization catalyst may be magnesium oxide (MgO).

Referring again to FIG. 1, the metathesis feed 158 may be contacted with metathesis catalyst or the metathesis catalyst and the cracking catalyst in the metathesis reactor 170 under conditions sufficient to promote the cross-metathesis of at least a portion of the mixed butenes in the metathesis feed 158 to produce at least propene, ethylene, or both. The metathesis feed 158 may be contacted with the metathesis catalyst or the metathesis catalyst and cracking catalyst at a gas hourly space velocity (GHSV) of from 10 per hour ($h^{-1}$) to 10,000 $h^{-1}$, such as from 100 $h^{-1}$ to 5000 $h^{-1}$, or from 300 h-1 to 2500 h-1. The metathesis feed 158 may be contacted with the metathesis catalyst or the metathesis catalyst and cracking catalyst in the metathesis reactor 170 at a temperature of from 200° C. to 600° C., such as from 300° C. to 550° C., or even from 350° C. to 500° C. The metathesis feed 158 may be contacted with the metathesis catalyst or the metathesis catalyst and cracking catalyst in the metathesis reactor 170 at a pressure of from 1 bar to 30 bar or from 2 bar to 20 bar. In embodiments, the metathesis feed 158 may be contacted with the metathesis catalyst or the metathesis catalyst and cracking catalyst in the metathesis reactor 170 at atmospheric pressure.

Contact of the metathesis feed 158 with the metathesis catalyst in the metathesis reaction zone 172 may cause at least a portion of the butenes (1-butene, trans-2-butene, cis-2-butene) to undergo metathesis to produce a metathesis reaction zone product stream that includes at least propene. The metathesis reaction zone product stream may additionally include C5+ olefins, ethylene, butenes, or combinations of these. The metathesis reaction zone product stream may be passed directly into contact with the cracking catalyst in the cracking reaction zone 174. Contact of metathesis reaction zone product stream with the cracking catalyst in the cracking reaction zone 174 may cause at least a portion of the C5+ olefins to undergo catalytic cracking reactions to produce the metathesis reaction effluent 176, which may have a greater concentration of propene compared to the metathesis reaction zone product stream prior to contacting with the cracking catalyst.

The metathesis reaction effluent 176 may be passed out of the metathesis reactor 170. In addition, the metathesis reaction effluent 176 may include one or more of ethylene, unreacted normal butenes, fuel gas, propane, isobutane, n-butane, isobutene, 1,3-butadiene, and C5+ compounds. At least a portion of the propane, n-butane, isobutane, isobutene, and 1,3-butadiene in the metathesis reaction effluent 176 may be constituents from the metathesis feed 158 that pass through the metathesis reactor 170 without undergoing reaction to form olefins. The ethylene and certain C5+ compounds, such as but not limited to pentene or hexene, may be produced in the metathesis reactor 170 through the metathesis reactions. At least a portion of the C5+ olefins may be converted to propene, ethylene, or olefins through contact with the cracking catalyst.

Referring again to FIG. 1, the metathesis reaction effluent 176 may be passed from the metathesis reactor 170 to the metathesis effluent separation system 180. The metathesis effluent separation system 180 may be fluidly coupled to the metathesis reactor 170 so that the metathesis reaction effluent 176 can be passed directly from the metathesis reactor 170 to the metathesis effluent separation system 180 without passing the metathesis reaction effluent 176 through any intervening unit operations, such as a reactor. The metathesis effluent separation system 180 may include one or a plurality of separators operable to separate the metathesis reaction effluent 176 into at least a metathesis C5+ effluent 184 and at least one other olefin-containing effluent, which may include at least one of ethylene, propene, normal butenes, or combinations of these. The metathesis C5+ effluent 184 and the at least one other olefin-containing effluent may comprise at least 95 percent by weight of the constituents of the metathesis reaction effluent 176. The metathesis effluent separation system 180 may be operable to separate the metathesis reaction effluent 176 into a metathesis C4 effluent 182, a metathesis C5+ effluent 184, a metathesis propene effluent 186, and a metathesis ethylene effluent 188. The metathesis C4 effluent 182, metathesis C5+ effluent 184, metathesis propene effluent 186, and metathesis ethylene effluent 188, combined, may include at least 95 percent, at least 98 percent, or even at least 99 percent by weight of the constituents of the metathesis reaction effluent 176. The separation units of the metathesis effluent separation system 180 may include, but are not limited to, flash drums, high-pressure separators, distillation units, fractional distillation units, membrane separation units, or combinations of these. One or more of the metathesis C4 effluent 182, metathesis C5+ effluent 184, the metathesis propene effluent 186, the metathesis ethylene effluent 188 may be passed to one or more downstream unit operations for further processing.

Referring again to FIG. 1, at least a portion of the metathesis C5+ effluent 184 may be passed from the metathesis system 160 back to the steam cracking system 110 for further conversion of C5+ compounds to ethylene, propene, or both. The portion of the metathesis C5+ effluent 184 may be passed through metathesis C5+ recycle 185 to a hydrotreating unit 140 disposed between the metathesis effluent separation system 180 and the steam cracking system 110. The system 100 may include the metathesis C5+ recycle 185 fluidly coupled to the metathesis system 160, such as to the metathesis effluent separation system 180, and to the hydrotreating unit 140. The metathesis C5+ recycle 185 may be operable to pass at least a portion of the metathesis C5+ effluent 184 from the metathesis system 160 to the hydrotreating unit 140 and ultimately back to the steam cracking system 110.

The hydrotreating unit 140 may be operable to receive the metathesis C5+ recycle 185, and optionally the isobutene effluent 154 from the isobutene removal unit 150, and contact the metathesis C5+ recycle 185, the isobutene effluent 154, or both with one or a plurality of hydrotreating catalysts under reaction conditions sufficient to saturate the olefins in the metathesis C5+ recycle 185, the isobutene effluent 154, or both to produce a hydrotreated effluent 142. The hydrotreating unit 140 may include one or a plurality of fixed bed reactors comprising one or more hydrotreating catalysts. The hydrotreating catalyst may be a catalyst capable of saturating isobutene and C5+ olefins to produce saturated hydrocarbons that can be subjected to steam cracking. Hydrotreating catalysts may include, but are not limited to hydrodesulfurization catalysts, hydrodemetalization catalysts, hydrodenitrogenation catalysts, hydrodearomatization catalysts, hydrocracking catalysts, or combinations of these. The hydrotreating catalysts may comprise one or more metal catalysts selected from the metallic elements in Groups 5, 6, 8, 9, or 10 of the IUPAC periodic table, such as, but not limited to, molybdenum, nickel, cobalt, and tungsten. The metals of the catalysts may be supported on a support. Support materials may include alumina or silica-alumina support materials. In embodiments, the support material may be a zeolite, such as a mesoporous zeolite support. The hydrotreating unit 140 may be operated at a temperature of from 300° C. to 450° C. and at a pressure of from 30 bars (3,000 kilopascals (kPa)) to 200 bars (20,000 kPa), such as from 30 bars (3,000 kPa) to 180 bars (18,000 kPa). The hydrotreating unit 140 may operate with a liquid hour space velocity (LHSV) of from 0.1 per hour ($hr^{-1}$) to 10 $hr^{-1}$, such as from 0.2 $hr^{-1}$ to 10 $hr^{-1}$.

The hydrotreated effluent 142 may be passed from the hydrotreating unit 140 to the steam cracking system 110 in which the hydrotreated effluent 142 can be contacted with steam at the temperature sufficient to cause at least a portion of hydrocarbons in the hydrotreated effluent 142 to undergo thermal cracking to produce olefins, such as ethylene, propene, and butene. The hydrotreated effluent 142 may be passed directly from the hydrotreating unit 140 to the steam cracking system 110, or the hydrotreated effluent 142 may be combined with the hydrocarbon feed 102 upstream of the steam cracking system 110 to produce a combined feed to the steam cracking system 110.

Contacting the saturated hydrocarbon compounds of the hydrotreated effluent 142 with steam at the temperatures of 700° C. to 900° C. in the pyrolysis zone 114 of the steam cracking reactor 111 may cause at least a portion of the saturated hydrocarbon compounds from the hydrotreated effluent 142 to undergo thermal cracking to produce olefins, such as ethylene, propene, and butene, and other C4-compounds. The additional conversion of at least a portion of the hydrocarbons from the hydrotreated effluent 142 may increase the overall conversion of the system 100 for producing olefins, such as ethylene and propene. Some portions of the hydrocarbon compounds in the hydrotreated effluent 142 may undergo cracking in the steam cracking system 110 to produce propene or ethylene, which may be passed out of the steam cracking system 110 in the cracking propene effluent 126 and the cracking ethylene effluent 128, respectively. Additionally, other portions of the hydrocarbon compounds from the hydrotreated effluent 142 may be converted to butenes in the steam cracking system 110. The butenes produced from cracking the portion of the hydrotreated effluent 142 may be passed downstream to the selective hydrogenation unit 130, the isobutene removal unit 150, and the metathesis system 160 for further conversion of normal butenes to ethylene and propene through metathesis. Thus, passing the hydrotreated effluent 142, which includes hydrocarbons resulting from hydrotreating C5+ olefins from the metathesis C5+ recycle 185, isobutene from the isobutene effluent 154, or both, back to the steam cracking system 110 may increase the overall conversion of the hydrocarbon feed 102 and the overall yield of propene for the system 100.

Referring again to FIG. 1, the metathesis C4 effluent 182 may include one or more of n-butane, isobutane, unreacted normal butenes, 1,3-butadiene, isobutene, or combinations of these. The metathesis C4 effluent 182 may also include other compounds having boiling point temperatures in the range of the C4 compounds of the metathesis C4 effluent 182, such as boiling point temperatures greater than the boiling point temperature of propene and less than the boiling point temperatures of the metathesis C5+ effluent 184. The metathesis C4 effluent 182 may be passed to one or a plurality of downstream unit operations (not shown) for further processing.

Additionally or alternatively, the metathesis C4 effluent 182 may be recycled back to the metathesis reactor 170 of the metathesis system 160 for further conversion of a portion of the normal butenes in the metathesis C4 effluent 182 to ethylene and propene. The at least a portion of the metathesis C4 effluent 182 may be passed from the metathesis effluent separation system 180 directly back to the metathesis reactor 170 or may be combined with the metathesis feed 158 upstream of the metathesis reactor 170 to produce a combined metathesis feed stream. The system 100 may include a metathesis C4 effluent recycle 183, which may be fluidly coupled to an outlet of the metathesis effluent separation system 180 and an inlet of the metathesis reactor 170. The metathesis C4 effluent recycle 183 may be operable to transfer at least a portion of the metathesis C4 effluent 182 from the metathesis effluent separation system 180 back to the metathesis reactor 170 and into contact with the metathesis catalyst or the metathesis catalyst and cracking catalyst in the metathesis reactor 170.

Passing the metathesis C4 effluent 182 back to the metathesis reactor 170 and contacting the metathesis C4 effluent 182 with the metathesis catalyst or the metathesis catalyst and cracking catalyst in the metathesis reactor 170 may further increase the overall conversion and yield of ethylene and propene of the system 100. Contacting at least a portion of the metathesis C4 effluent 182 with the metathesis catalyst or metathesis catalyst and cracking catalyst in the metathesis reactor 170 may cause at least a portion of the normal butenes in the metathesis C4 effluent 182 to undergo metathesis reactions to produce olefins, such as ethylene, propene, or both. Thus, recycling the metathesis C4 effluent 182 back to the metathesis reactor 170 may increase the overall conversion and yield of propene from the system 100. Recycling the metathesis C4 effluent 182 back to the metathesis reactor 170 may also increase the yield of ethylene from the system 100.

Referring again to FIG. 1, the metathesis C4 effluent 182 passed out of the metathesis system 160 may include isobutene produced in or passed through the metathesis system 160. In embodiments, at least a portion of the metathesis C4 effluent 182 may be passed back to the isobutene removal unit 150 so that at least a portion of the isobutene in the metathesis C4 effluent 182 can be removed through reaction with methanol to produce MTBE. The portion of the metathesis C4 effluent 182 may be passed back to the isobutene removal unit 150 as the metathesis C4 effluent recycle 183. The metathesis C4 effluent recycle 183 may be passed directly to the isobutene removal unit 150, such as directly to the MTBE reactor 200 of the isobutene removal unit 150, or may be combined with the hydrogenation effluent 134 upstream of the isobutene removal unit 150. Recycling at least a portion of the metathesis C4 effluent 182 back to the isobutene removal unit 150 as the metathesis C4 effluent recycle 183 may further increase the selectivity and yield of propene for the system 100 by removing isobutene from the metathesis C4 effluent 182 before passing it back to the metathesis system 160.

Referring again to FIG. 1, in embodiments, the metathesis C4 effluent 182 passed out of the metathesis system 160 may include 1,3-butadiene or other dienes produced in or passed through the metathesis system 160. In embodiments, at least a portion of the metathesis C4 effluent 182 may be passed back to the selective hydrogenation unit 130 so that at least a portion of the 1,3-butadiene in the metathesis C4 effluent 182 can be removed through selective hydrogenation in the selective hydrogenation unit 130. The portion of the metathesis C4 effluent 182 may be passed back to the selective hydrogenation unit 130 as the metathesis C4 effluent recycle 183. The metathesis C4 effluent recycle 183 may be passed directly to the selective hydrogenation unit 130 or may be combined with the cracking C4 effluent 122 upstream of the selective hydrogenation unit 130. Recycling at least a portion of the metathesis C4 effluent 182 back to the selective hydrogenation unit 130 as the metathesis C4 effluent recycle 183 may further increase the selectivity and yield of propene for the system 100 by removing 1,3-butadiene from the metathesis C4 effluent 182 before passing it along to the isobutene removal unit 150 and the metathesis system 160 downstream of the isobutene removal unit 150.

Referring to FIG. 1, the metathesis propene effluent 186 and the metathesis ethylene effluent 188 may be passed to one or more downstream unit operations for further processing, such as but not limited to purification or polymerization processes. The metathesis propene effluent 186 may be combined with the cracking propene effluent 126 from the steam cracking system 110 to form a combined propene effluent passed out of the system 100. Likewise, the metathesis ethylene effluent 188 may be combined with the cracking ethylene effluent 128 to form a combined ethylene effluent passed out of the system 100. The combined propene effluent and the combined ethylene effluent of the system 100 may be passed independently to downstream operations for further processing.

In embodiments, the metathesis ethylene effluent 188 may not be passed back to the metathesis reactor 170 and no supplemental ethylene may be introduced or passed to the metathesis reactor 170. Ethylene itself can be a useful intermediate for producing other chemical products, such as polyethylene and other polymers. Thus, the metathesis reactor 170 may be operated in the absence of any supplemental ethylene introduced to the metathesis reactor 170 and the only ethylene present in the metathesis reactor 170 may be any residual ethylene incidentally remaining in the metathesis feed 158 passed to the metathesis system 160 or ethylene produced in the metathesis reactor 170 through cross-metathesis of 1-butene and 2-butene.

Figure 4:
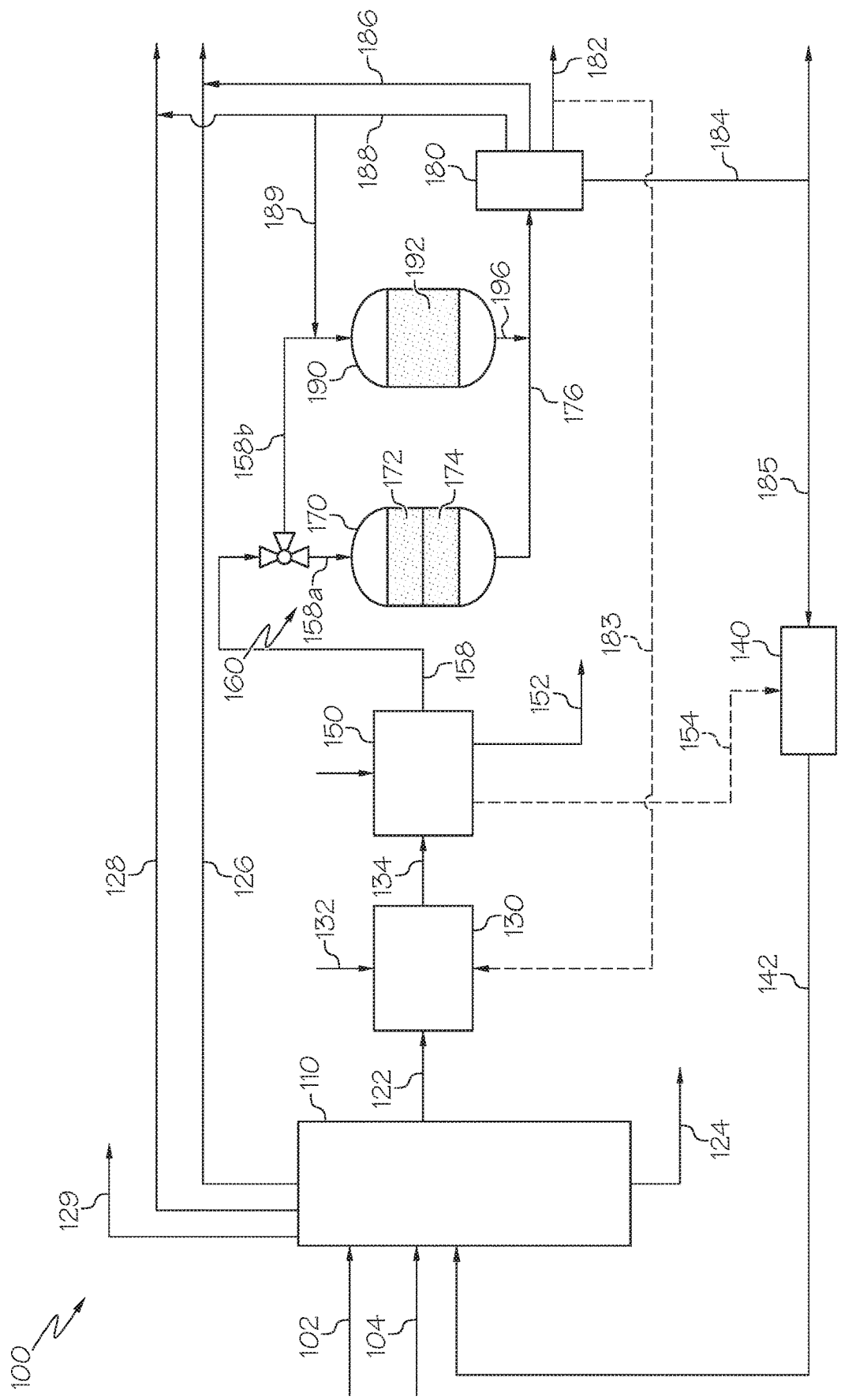
FIG. 4 schematically depicts a process flow diagram of another system for producing olefins, according to one or more embodiments shown and described in the present disclosure.

Referring now to FIG. 4, in embodiments, ethylene produced through metathesis of butene in the metathesis system 160 may be recycled back to the metathesis system 160 as a reactant. In the metathesis system 160, the ethylene may react with 2-butene in the presence of the metathesis catalyst to produce propene. The system 100 depicted in FIG. 4 may include the steam cracking system 110, the selective hydrogenation unit 130, and the isobutene removal unit 150 previously described in the present disclosure. When ethylene is recycled back to the metathesis system 160, the metathesis system 160 may include the metathesis reactor 170 and a supplemental metathesis reactor 190, which may be operated in parallel with the metathesis reactor 170. The metathesis reactor 170 may include the metathesis reaction zone 172 with the metathesis catalyst and the cracking reaction zone 174 with the cracking catalyst downstream of the metathesis reaction zone 172, as previously discussed. The metathesis reactor 170 may have any of the features, catalysts, or operating conditions previously described in the present disclosure for the metathesis reactor 170. The metathesis reactor 170 may include one or a plurality of reaction vessels in series or in parallel.

Referring again to FIG. 4, the supplemental metathesis reactor 190 may include at least one metathesis reaction zone 192 comprising a supplemental metathesis catalyst. The supplemental metathesis catalyst in the supplemental metathesis reactor 190 may be the same as or different from the metathesis catalyst in the metathesis reaction zone 172 of the metathesis reactor 170. The supplemental metathesis catalyst in the supplemental metathesis reactor 190 may have any of features, compositions, or characteristics previously described in the present disclosure for the metathesis catalyst. The supplemental metathesis reactor 190 may include one reactor or a plurality of reactors arranged and operated in series or in parallel. In embodiments, the supplemental metathesis reactor 190 may not include a cracking catalyst. In embodiments, the supplemental metathesis reactor 190 may include an isomerization catalyst operable to isomerize 1-butene to 2-butene or 2-butene to 1-butene.

Referring to FIG. 4, a first portion 158a of the metathesis feed 158 may be directed to the metathesis reactor 170 and a second portion 158b of the metathesis feed 158 may be directed to the supplemental metathesis reactor 190. The first portion 158a of the metathesis feed 158 may be contacted with the metathesis catalyst in the metathesis reaction zone 172 and the cracking catalyst in the cracking reaction zone 174 to produce the metathesis reaction effluent 176. The second portion 158b of the metathesis feed 158 may be passed to the supplemental metathesis reactor 190. At least a portion of the metathesis ethylene effluent 188 may also be passed to the supplemental metathesis reactor 190 through a metathesis ethylene recycle 189. The metathesis ethylene recycle 189 may be operable to pass at least a portion of the metathesis ethylene effluent 188 from the metathesis effluent separation system 180 back to the supplemental metathesis reactor 190. The metathesis ethylene recycle 189 may be combined with the second portion 158b of the metathesis feed 158 upstream of the supplemental metathesis reactor 190 or may be passed to the supplemental metathesis reactor 190 independent of the second portion 158b of the metathesis feed 158. A supplemental ethylene stream, ethylene from the cracking ethylene effluent 128, or both, may also be passed to the supplemental metathesis reactor 190.

Referring again to FIG. 4, the second portion 158b of the metathesis feed 158 and ethylene from the metathesis ethylene recycle 189 may be combined in the supplemental metathesis reactor 190 and contacted with the supplemental metathesis catalyst in the metathesis reaction zone 192. Contact between the ethylene and 2-butene (trans-2-butene, cis-2-butene, or both) in the presence of the supplemental metathesis catalyst in the metathesis reaction zone 192 may cause cross-metathesis between at least a portion of ethylene and at least a portion of the 2-butenes to produce propene. Cross-metathesis between 1-butene and 2-butene to produce propene and pentene and other metathesis reactions may also occur in the supplemental metathesis reactor 190. A supplemental metathesis reaction effluent 196 may be passed out of the supplemental metathesis reactor 190. The supplemental metathesis reaction effluent 196 may include the propene, ethylene, and C5+ olefins produced through the various cross-metathesis reactions occurring in the supplemental metathesis reactor 190, unreacted ethylene, and unreacted C4 constituents from the second portion 158b of the metathesis feed 158.

Recycling at least a portion of the metathesis ethylene effluent 188 back to the metathesis system 160, such as back to the supplemental metathesis reactor 190, through the metathesis ethylene recycle 189 may operate to shift the system 100 towards greater yield of propene relative to ethylene compared to operation of the system 100 without recycling the metathesis ethylene effluent 188 back to the metathesis system 160. Thus, recycling at least a portion of the metathesis ethylene effluent 188 back to the metathesis system 160 may further increase the selectivity and yield of propene from the system 100.

Referring again to FIG. 4, the metathesis reaction effluent 176 and the supplemental metathesis reaction effluent 196 may be passed to the metathesis effluent separation system 180. The metathesis reaction effluent 176 and the supplemental metathesis reaction effluent 196 may be passed individually to the metathesis effluent separation system 180 or may be combined upstream of the metathesis effluent separation system 180. As previously discussed, the metathesis effluent separation system 180 may be operable to separate the metathesis reaction effluents into a plurality of effluent streams, such as but not limited to the metathesis C4 effluent 182, the metathesis C5+ effluent 184, the metathesis propene effluent 186, and the metathesis ethylene effluent 188. As previously discussed, at least a portion of the metathesis C5+ effluent 184 may be passed back to the steam cracking system 110 through the metathesis C5+ recycle 185, and at least a portion of the metathesis C4 effluent 182 may be passed back to the selective hydrogenation unit 130, the isobutene removal unit 150, or the metathesis system 160, as previously discussed.

Referring now to FIG. 5, the system 100 may not include the metathesis effluent separation system 180. Instead, the system 100 may include a combined separation system 300, and the metathesis reaction effluent 176 and the cracking reaction effluent 117 may both be passed to the combined separation system 300. In FIG. 5, the steam cracking reactor 111, the selective hydrogenation unit 130, the isobutene removal unit 150, and the metathesis reactor 170 may have any of the features or characteristics previously described for these unit operations. The metathesis reaction effluent 176 and the cracking reaction effluent 117 may be passed separately and independently to the combined separation system 300 or may be combined upstream of the combined separation system 300. The combined separation system 300 may include one or a plurality of separation units in series or in parallel. The combined separation system 300 may be operable to separate the metathesis reaction effluent 176 and the cracking reaction effluent 117 into at least a C4 stream 312, a greater boiling effluent 314, a system propene effluent 316, a system ethylene effluent 318, and a lesser-molecular weight gas effluent 319. The metathesis reaction effluent 176 may be passed directly from the metathesis reactor 170 to the combined separation system 300.

The metathesis reaction effluent 176 may include isobutene produced in the metathesis reactor 170. This isobutene may pass out of the combined separation system 300 in the C4 stream 312. The C4 stream 312 may be passed from the combined separation system 300 to the selective hydrogenation unit 130 and the isobutene removal unit 150 for removal of 1,3-butadiene and isobutene, respectively. The greater boiling effluent 314, the system propene effluent 316, the system ethylene effluent 318, and the lesser-molecular weight gas effluent 319 may each be passed out of the combined separation system 300 and out of the system 100 to one or more downstream unit operations for further processing. The combined separation system 300 may also be used in the system 100 in which the ethylene is recycled back to the metathesis system 160 as shown in FIG. 4. The system ethylene effluent 318 may then be passed to the supplemental metathesis reactor 190 (FIG. 4), and both the metathesis reaction effluent 176 and the supplemental metathesis reaction effluent 196 (FIG. 4) can be passed to the combined separation system 300.

Referring again to FIG. 1, processes for producing olefins may be conducted using the systems 100 of the present disclosure, which may include at least the steam cracking system 110, the selective hydrogenation unit 130, the isobutene removal unit 150, and the metathesis system 160 as previously described in the present disclosure. Processes for producing olefins may include contacting the hydrocarbon feed 102 with steam in the steam cracking system 110 at a temperature sufficient to produce the cracking reaction effluent 117 (FIG. 2) and separating the cracking reaction effluent 117 in the cracking effluent separation system 120 (FIG. 2) to produce at least the cracking C4 effluent 122 comprising normal butenes, isobutene, and 1,3-butadiene. The steam cracking system 110 may have any of the features, characteristics, or operating conditions previously described in the present disclosure for steam cracking system 110. Referring again to FIG. 1, the processes may further include subjecting the cracking C4 effluent 122 to selective hydrogenation in the selective hydrogenation unit 130 to produce the hydrogenation effluent 134. Selective hydrogenation may cause at least a portion of the 1,3-butadiene in the cracking C4 effluent 122 to react to form normal butenes. The selective hydrogenation unit 130 may have any of the features, characteristics, or operating conditions previously described in the present disclosure for selective hydrogenation unit 130. The processes may further include passing the hydrogenation effluent 134 to the isobutene removal unit 150 downstream of the selective hydrogenation unit 130 and removing isobutene from the hydrogenation effluent 134 in the isobutene removal unit 150 to produce at least a metathesis feed 158 comprising normal butenes. The isobutene removal unit 150 may have any of the features, characteristics, or operating conditions previously described in the present disclosure for isobutene removal unit 150. The processes may further include passing at least a portion of the metathesis feed 158 to the metathesis system 160 comprising a metathesis catalyst and a cracking catalyst directly downstream of the metathesis catalyst and contacting the portion of the metathesis feed 158 with the metathesis catalyst and the cracking catalyst to produce a metathesis reaction effluent 176. The metathesis system 160 may have any of the features, characteristics, or operating conditions previously described in the present disclosure for metathesis system 160. Contacting with the metathesis catalyst may cause metathesis of normal butenes in the metathesis feed 158 to produce at least ethylene, propene, and C5+ olefins, and contacting with the cracking catalyst may cause at least a portion of the C5+ olefins produced through metathesis to undergo cracking reactions to produce ethylene, propene, or both. The metathesis reaction effluent may include at least ethylene, propene, or both. The hydrocarbon feed 102 may include a naphtha stream, a gas condensate stream, or both.

As previously discussed, the metathesis system 160 may include a metathesis reactor 170 having the metathesis reaction zone 172 comprising the metathesis catalyst and the cracking reaction zone 174 comprising the cracking catalyst, where the cracking reaction zone 174 is directly downstream of the metathesis reaction zone 172. The processes may further include passing at least a portion of the metathesis feed 158 through the metathesis reaction zone 172 and the cracking reaction zone 174 downstream of the metathesis reaction zone 172. Contacting the metathesis feed 158 with the metathesis catalyst in the metathesis reaction zone 172 may cause at least a portion of the normal butenes in the metathesis feed 158 to undergo metathesis to produce at least propene and C5+ olefins. Contacting the resulting C5+ olefins with the cracking catalyst in the cracking reaction zone 174 may cause at least a portion of the C5+ olefins to undergo catalytic cracking to produce at least one of ethylene, propene, or both. In embodiments, the cracking catalyst may be in contact with the metathesis catalyst. In other embodiments, the metathesis reaction zone 172 may be disposed in a first reactor, the cracking reaction zone 174 may be disposed in a second reactor directly downstream of the first reactor, and a conduit may fluidly couple the second reactor to the first reactor. The metathesis catalyst may have any of the features or compositions previously described in the present disclosure for the metathesis catalyst. In embodiments, the metathesis catalyst may be at least one metal oxide deposited on the surfaces of a mesoporous silica catalyst support or a mesoporous silica-alumina catalyst support. The cracking catalyst may have any of the features or compositions previously described in the present disclosure for the cracking catalyst. In embodiments, the cracking catalyst may be an MFI structured silica-containing catalyst.

Referring again to FIG. 1, the processes may further include separating the metathesis reaction effluent 176 into the metathesis C4 effluent 182, the metathesis C5+ effluent 184, the metathesis propene effluent 186, and the metathesis ethylene effluent 188. The processes may further include passing at least a portion of the metathesis C5+ effluent 184 back to the steam cracking system 110. Passing the at least a portion of the metathesis C5+ effluent 184 back to the steam cracking system 110 may include hydrotreating the portion of the metathesis C5+ effluent 184 in the hydrotreating unit 140 to produce the hydrotreated effluent 142 and passing the hydrotreated effluent 142 back to the steam cracking system 110. The hydrotreating unit 140 may have any of the features, characteristics, or operating conditions previous described in the present disclosure for the hydrotreating unit 140. The processes may further include contacting the hydrotreated effluent 142 with steam at the temperature of from 700° C. to 900° C. in the steam cracking system 110, where the contacting causes at least a portion of the hydrotreated effluent 142 to undergo steam cracking. The processes may further include passing at least a portion of the metathesis C4 effluent 182 back to the metathesis system 160, the isobutene removal unit 150, or the selective hydrogenation unit 130. The metathesis ethylene effluent 188 may be passed back to the metathesis system 160. In embodiments, the metathesis ethylene effluent 188 may not be passed back to the metathesis system 160 and no supplemental ethylene may be introduced to the metathesis system 160.

Referring to FIG. 4, as previously discussed, the processes may include passing the metathesis ethylene effluent 188 back to the metathesis system 160. The metathesis system 160 may include the metathesis reactor 170 comprising the metathesis reaction zone 172 having the metathesis catalyst and the cracking reaction zone 174 downstream of the metathesis reaction zone 172 and having the cracking catalyst. The metathesis system 160 may further include the supplemental metathesis reactor 190 comprising the supplemental metathesis catalyst. The supplemental metathesis reactor 190 may be operated in parallel with the metathesis reactor 170. The processes may include contacting a first portion 158a of the metathesis feed 158 with the metathesis catalyst and the cracking catalyst in the metathesis reactor 170 to produce the metathesis reaction effluent 176 and contacting a second portion 158b of the metathesis feed 158 and the portion of the metathesis ethylene effluent 188 with the supplemental metathesis catalyst in the supplemental metathesis reactor 190 to produce the supplemental metathesis reaction effluent 196.

Referring again to FIG. 1, subjecting the cracking C4 effluent 122 to selective hydrogenation may include contacting the cracking C4 effluent 122 with hydrogen from hydrogen stream 132 in the presence of a selective hydrogenation catalyst in the selective hydrogenation unit 130 at reaction conditions sufficient to cause at least a portion of the 1,3-butadiene in the steam cracking C4 effluent 122 to undergo a hydrogenation reaction to produce a hydrogenation effluent 134 having a concentration of 1,3-butadiene less than a concentration of 1,3-butadiene in the cracking C4 effluent. The hydrogenation effluent 134 may have a greater concentration of normal butenes compared to the concentration of normal butenes in the cracking C4 effluent 122.

Referring to FIG. 3, removing isobutene from the hydrogenation effluent 134 may include contacting the hydrogenation effluent with methanol 156 in the MTBE reactor 200 of the isobutene removal unit 150 under reaction conditions sufficient to convert at least a portion of isobutene in the hydrogenation effluent 134 to methyl-tert-butyl ether to produce the MTBE reactor effluent 202. The processes may further include separating the MTBE reactor effluent 202 into at least the MTBE effluent 152 and the metathesis feed 158, which may include normal butenes. The processes may further include recovering at least a portion of the methyl-tert-butyl ether from the MTBE effluent 152. Referring to FIGS. 1 and 3, in embodiments, the processes may include passing at least a portion of the MTBE effluent 152 back to the steam cracking system 110. Passing the portion of the MTBE effluent 152 back to the steam cracking system may include contacting the MTBE effluent 152 with a cracking catalyst under conditions sufficient to produce an isobutene effluent 154, where the contacting with the cracking catalyst may cause at least a portion of the methyl-tert-butyl ether in the MTBE effluent 152 to react to form isobutene. The cracking catalyst may have any of the features or compositions previously described in the present disclosure for cracking catalysts. The processes may further include passing the isobutene effluent 154 back to the steam cracking system 110. The processes may further include passing the isobutene effluent 154 to the hydrotreating unit 140 and contacting the isobutene effluent 154 with one or more hydrotreating catalysts at reaction conditions sufficient to saturate the isobutene in the isobutene effluent 154. The isobutene effluent 154 may be passed independently to hydrotreating unit 140 or may be combined with the metathesis C5+ recycle 185 upstream of the hydrotreating unit 140.

Referring now to FIG. 2, the processes further include separating the cracking reaction effluent 117 to produce the cracking C4 effluent 122 comprising butenes, and one or more of the fuel oil 123, the pyrolysis gas 125, the cracking propene effluent 126, the cracking ethylene effluent 128, the lesser molecular weight gas 129, or combinations of these. Separating the cracking reaction effluent 117 may include passing the cracking reaction effluent 117 to the cracking effluent separation system 120 that may include one or a plurality of separators operable to separate the cracking reaction effluent 117 into the cracking C4 effluent 122 and at least one of the fuel oil 123, the pyrolysis gas 125, the cracking propene effluent 126, the cracking ethylene effluent 128, the lesser molecular weight gas 129, or combinations of these. The processes may include contacting the hydrocarbon feed 102 with the stream 104 in the pyrolysis zone 114 of the steam cracking reactor 111 at a temperature of from 700° C. to 900° C., for a residence time of from 0.05 seconds to 2 seconds, and at a mass ratio of steam to hydrocarbon of from 0.3:1 to 2:1. The processes may further include preheating the hydrocarbon feed 102 in the convection zone 112 of the steam cracking reactor 111.

Referring now to FIG. 5, in embodiments, the processes may include passing the cracking reaction effluent 117 and the metathesis reaction effluent 176 to a combined separation system 300. The cracking reaction effluent 117 and the metathesis reaction effluent 176 may be passed independently to the combined separation system 300 or may be combined upstream of the combined separation system 300. The combined separation system 300 may include one or more separation units and may be operable to separate the cracking reaction effluent 117 and the metathesis reaction effluent 176 into a C4 effluent 312 and at least one of the greater boiling effluent 314, the system propene effluent 316, the system ethylene effluent 318, the lesser-molecular weight gas effluent 319, or combinations of these. The greater boiling effluent 314 may be further separated into one or more of a fuel oil stream, a pyrolysis gas stream, or other greater boiling stream.

The systems and processes of the present disclosure may be employed to produce olefins, such as ethylene and propene, from hydrocarbon feeds, such as naphtha and gas condensate streams. The ethylene and propene produced by the systems and processes of the present disclosure may be used as intermediates in various chemical processes to produce further chemical products. As a non-limiting example, the ethylene and propene may be introduced to a polymerization process to make polymer materials, such as but not limited to polyethylene-based polymers, polypropene-based polymers, or combinations of these. Ethylene and propene may also be used as reactants in various other reactions, such as but not limited to, oxidation, alkylation, oligomerization, hydration, to produce chemical products. Other uses of the ethylene and propene produced by the systems and processes of the present disclosure are also contemplated.

EXAMPLES

The following non-limiting examples illustrate one or more features of the present disclosure.

Example 1

Cracking Reaction Products from Steam Cracking of a Naphtha Feed

In Example 1, the composition of the cracking reaction product resulting from steam cracking a naphtha feed in a steam cracking reactor was modeled. The naphtha feed was an Arab Extra Light (AXL) naphtha stream produced by Saudi Arabian Oil Company. Properties and characteristics of the AXL naphtha stream for example 1 are provided in Table 2.

TABLE 2

Properties and Characteristics for AXL Naphtha Feed

| Property | Value | Units | Test Method |
| --- | --- | --- | --- |
| API Specific Gravity (SG) | 0.7089 | None | ASTM D1298 |
| Initial Boiling Point (IBP) | 167.2 | ° C. | ASTM D86 |
| 50% Boiling Point | 212.9 | ° C. | ASTM D86 |
| 95% Boiling Point | 265.5 | ° C. | ASTM D86 |
| Paraffins by Volume | 42.6 | Volume % | ASTM D8017 |

TABLE 2-continued

Properties and Characteristics for AXL Naphtha Feed

| Property | Value | Units | Test Method |
| --- | --- | --- | --- |
| Isoparaffins by Volume | 28.1 | Volume % | ASTM D8017 |
| Naphthenes by Volume | 26.8 | Volume % | ASTM D8017 |
| Aromatics by Volume | 2.5 | Volume % | ASTM D8017 |

The steam cracking reactor was modeled using AspenPlus® 9 chemical process modeling software (AspenTech). Contact of the naphtha feed with steam at the reaction conditions produced a cracking reaction product having the composition in Table 3, which is provided in weight percent (wt. %) and in kilotons per anum (KTA).

TABLE 3

Cracking reaction products from steam cracking of a naphtha feed of Example 1

| | Feed Cracking Reaction Product from Naphtha Feed | |
| --- | --- | --- |
| Product Yields | wt. % | KTA |
| Hydrogen | 0.9 | 9 |
| Methane | 10.9 | 109 |
| Ethylene | 26.9 | 269 |
| Propene | 15.7 | 157 |
| Propane | 0.0 | 0 |
| Mixed C4 Compounds | 12.3 | 123 |
| Pyrolysis Gas | 24.2 | 242 |
| Fuel oil | 9.0 | 90 |
| Total | 100 | 1000 |

Example 2

Cracking Reaction Products from Steam Cracking of a Gas Condensate Feed

In Example 2, the composition of the cracking reaction products resulting from steam cracking a gas condensate feed were modeled. The gas condensate feed was a gas condensate produced from the Khuff reservoirs in Saudi Arabia (Khuff gas condensate or KGC) and having the composition provided in Table 1. The steam cracking reactor was modeled using AspenPlus® 9 chemical process modeling software (AspenTech). Contact of the gas condensate feed with steam at the reaction conditions produced a cracking reaction product having the composition in Table 4, which provided in weight percent (wt. %) and in tons.

TABLE 4

Cracking reaction products from high-severity fluidized catalytic cracking of a Khuff gas condensate feed for Example 2

| | Feed Cracking Reaction Product from Gas Condensate Feed | |
| --- | --- | --- |
| Product Yields | wt. % | KTA |
| Hydrogen | 2.1 | 21 |
| Methane | 10.9 | 109 |
| Ethylene | 27.8 | 278 |
| Propene | 14.5 | 145 |
| Propane | 0.0 | 0 |
| Mixed C4 Compounds | 9.5 | 95 |

TABLE 4-continued

Cracking reaction products from high-severity fluidized catalytic cracking of a Khuff gas condensate feed for Example 2

| Product Yields | Feed wt. % | Cracking Reaction Product from Gas Condensate Feed KTA |
|---|---|---|
| Pyrolysis Gas | 17.3 | 173 |
| Fuel Oil | 17.9 | 179 |
| Total | 100 | 1000 |

Example 3

Integrated Steam Cracking and Metathesis Process For Naphtha Feed

Figure 6:
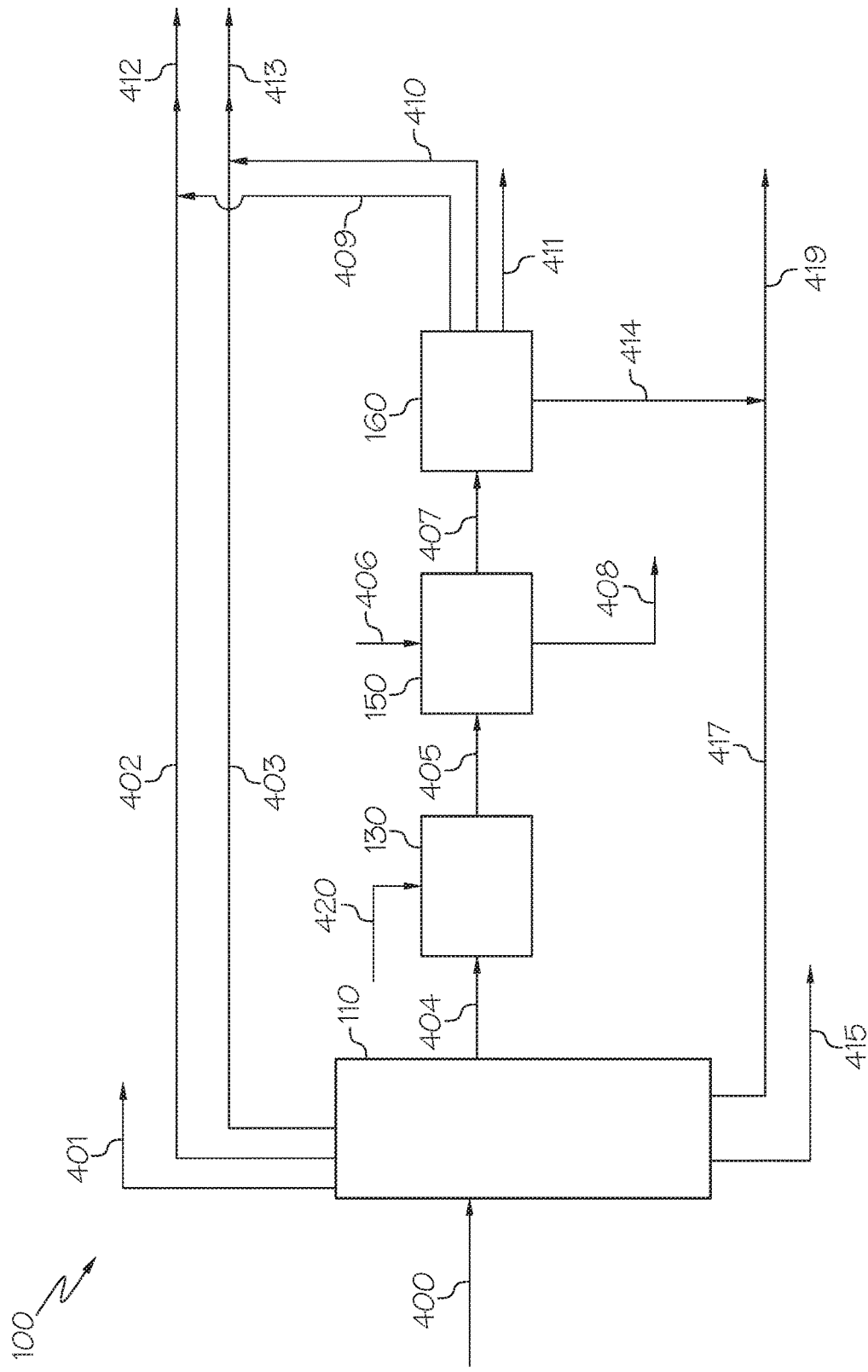
FIG. 6 schematically depicts a process flow diagram of a system for producing olefins modeled in the Examples section, according to one or more embodiments shown and described in the present disclosure.

In Example 3, the system 100 of FIG. 6 integrating a steam cracking system 110 with a metathesis system 160 for upgrading a hydrocarbon feed 400 comprising naphtha to ethylene and propylene is modeled. A combination of AspenPlus® 9 chemical process modeling software (Aspen-Tech) and bench scale reactor testing is used to model the system 100, which includes the steam cracking system 110, the selective hydrogenation unit 130 downstream of the steam cracking system 110, the isobutene removal unit 150 downstream of the selective hydrogenation unit 130, and the metathesis system downstream of the isobutene removal unit 150. The naphtha for the hydrocarbon feed is the AXL naphtha stream from Table 2.

Referring to FIG. 6, the steam cracking system 110 is operated at a temperature of the convection zone of 565° C. The outlet of the furnace of the steam cracking system was set to 825° C. and 25 pounds per square inch absolute (psia) (172 kPa). The mass balance for the steam cracking system 110 is provided in Table 5. The cracking reaction effluent is separated into a lesser molecular weight gas 401, a cracking ethylene effluent 402, a cracking propene effluent 403, a cracking C4 effluent 404, a pyrolysis gas 415, and a fuel oil 416. Separation of the cracking reaction effluent into the various effluent streams is assumed to be 100%. The cracking C4 effluent 404 is passed to the selective hydrogenation unit 130. Hydrogen is also passed to the selective hydrogenation unit 130 by way of hydrogen stream 420, and the weight ratio of hydrogen to 1,3-butadiene in the selective hydrogenation unit 130 is set to 2.2. The conversion of 1,3-butadiene in the selective hydrogenation unit 130 is set to 100% conversion of 1,3-butadiene to normal butenes (1-butene, trans-2-butene, cis-2-butene). The mass balance for the selective hydrogenation unit 130 is provided in Table 5.

A hydrogenation effluent 405 is passed from the selective hydrogenation unit 130 to the isobutene removal unit 150. Methanol 406 is also passed to the isobutene removal unit 150. The amount of methanol 406 is 12 wt. % based on the total mass flow rate of the hydrogenation effluent 405 and the methanol 406. The conversion of isobutene to MTBE in the isobutene removal unit 150 is set to 100% conversion and the separation of MTBE 408 from the metathesis feed 407 is assumed to be 100% efficient. The mass balance for the isobutene removal unit 150 is provided in Table 5.

The metathesis system 160 includes a metathesis reaction zone comprising a metathesis catalyst and a cracking reaction zone downstream of the metathesis reaction zone and comprising a cracking catalyst. The metathesis system 160 was tested using a bench scale reactor having the metathesis catalyst in the metathesis reaction zone and the cracking catalyst in the cracking reaction zone downstream of the metathesis reaction zone. The feed to the bench scale metathesis reactor was synthesize using the composition modeled for the metathesis feed 407 and provided below in Table 6. In particular, the metathesis feed included 55.6 wt. % 1-butene, 32.7 wt. % 2-butene, 5.6 wt. % n-butane, and 3.7 wt. % isobutane based on the total weight of the metathesis feed. The metathesis reaction effluent was analyzed to determine the composition. The metathesis system 160 produced a total conversion of butene of 80% with a propylene selectivity of 46% and an ethylene selectivity of 14.5%. The metathesis reaction effluent is separated into a metathesis ethylene effluent 409, a metathesis propene effluent 410, a metathesis C4 effluent 411, and a metathesis C5+ effluent 414. Separation of the metathesis reaction effluent into the various effluents 409, 410, 411, and 414 is assumed to be 100% efficient. The mass balance for the metathesis system 160 is provided in Table 5.

TABLE 5

Mass Balance Information for Modeling the Unit Operations of FIG. 6 for Example 3.

| | Yields | | | | | | | |
|---|---|---|---|---|---|---|---|---|
| | Steam Cracking System | | Selective Hydrogenation Unit | | Isobutene Removal Unit | | Metathesis System | |
| Feed | wt. % | KTA | wt. % | KTA | wt. % | KTA | wt. % | KTA |
| AXL | 100 | 1000 | — | — | — | — | — | — |
| Hydrogen | — | — | 4 | 5 | | | 2 | 2 |
| Cracking C4 Eff | — | — | 96 | 123 | — | — | — | — |
| Hydrogenation Eff. | — | — | — | — | 88 | 128 | — | — |
| Methanol | — | — | — | — | 12 | 17 | — | — |
| Metathesis Feed | — | — | — | — | — | — | 98 | 95 |
| Total Feed | 100 | 1000 | 100 | 128 | 100 | 140 | 100 | 98 |
| Component Yields in Effluent | | | | | | | | |
| Off-gas | NA | NA | NA | NA | NA | NA | 1 | 1 |
| Hydrogen | 1 | 9 | 2 | 2 | 2 | 2 | 2 | 2 |
| Methane | 11 | 109 | 0 | 0 | 0 | 0 | NA | NA |
| Ethylene | 27 | 269 | 0 | 0 | 0 | 0 | 13 | 13 |
| Propylene | 16 | 157 | 0 | 0 | 0 | 0 | 38 | 37 |

TABLE 5-continued

Mass Balance Information for Modeling the Unit Operations of FIG. 6 for Example 3.

|  | Yields | | | | | | | |
|---|---|---|---|---|---|---|---|---|
|  | Steam Cracking System | | Selective Hydrogenation Unit | | Isobutene Removal Unit | | Metathesis System | |
| Feed | wt. % | KTA | wt. % | KTA | wt. % | KTA | wt. % | KTA |
| 1,3-butadiene | 12 | 123 | 0 | 0 | 0 | 0 | 0 | 0 |
| Isobutene |  |  | 24 | 30 | 0 | 0 | 11 | 11 |
| 1-Butene |  |  | 43 | 54 | 38 | 53 | 6 | 5 |
| 2-Butene |  |  | 25 | 32 | 22 | 31 | 12 | 12 |
| n-Butane |  |  | 4 | 5 | 4 | 5 | 5 | 5 |
| Isobutane |  |  | 3 | 4 | 2 | 4 | 4 | 4 |
| MTBE | NA | N/A | NA | NA | 32 | 46 | NA | 0 |
| C5+ | NA | NA | 0 | 0 | 0 | 0 | 6 | 5 |
| Pyrolysis Gas | 24 | 242 | NA | NA | NA | NA | NA | NA |
| Fuel Oil | 9 | 90 | NA | NA | NA | NA | NA | NA |
| Total Yield | 100 | 1000 | 100 | 128 | 100 | 145 | 100 | 98 |

KTA stands for kilotons per annum.
Weight percent (wt. %) for the feed to each unit operation is based on the total weight of all feed streams introduced to that unit operation.
Weight percent (wt. %) for the Component Yields in Effluent from one of the unit operations are based on the total weight of the effluent passed out of that unit operation.

The metathesis ethylene effluent 409 is combined with the cracking ethylene effluent 402 to produce a system ethylene effluent 412. The metathesis propene effluent 410 is combined with the cracking propene effluent 403 to produce a system propene effluent. The metathesis C5+ effluent 414 is combined with the fuel oil effluent 417 from the steam cracking system 110 to produce a system fuel oil effluent 419. The modeling data for the system 100 of FIG. 6 with the naphtha hydrocarbon feed is provided in Table 6.

TABLE 6

Modeling Data for System of FIG. 6 with the AXL Naphtha Feed According to Example 3.

| | Stream # | | | | | | | | | |
|---|---|---|---|---|---|---|---|---|---|---|
|  | 400 | 401 | 402 | 403 | 404 | 420 | 405 | 406 | 407 | 408 |
|  | Units | | | | | | | | | |
|  | KTA | KTA | KTA | KTA | KTA | KTA | KTA | KTA | KTA | KTA |
| AXL | 1000 | — | — | — | — | — | — | — | — | — |
| Hydrogen | — | — | — | — | — | 4.6 | 2.4 | — | 2 | — |
| Fuel Gas | — | 118.3 | — | — | — | — | — | — | — | — |
| Methanol | — | — | — | — | — | — | — | 17.0 | — | — |
| MTBE | — | — | — | — | — | — | — | — | — | 47.1 |
| Ethylene | — | — | 269 | — | — | — | — | — | — | — |
| Propene | — | — | — | 156.9 | — | — | — | — | — | — |
| Butadiene | — | — | — | — | 57.0 | — | 0.0 | — | — | — |
| Isobutene | — | — | — | — | 29.5 | — | 30.1 | — | — | — |
| 1-Butene | — | — | — | — | 18.2 | — | 54.4 | — | 54.4 | — |
| 2-Butene | — | — | — | — | 9.6 | — | 32.0 | — | 32.0 | — |
| n-Butane | — | — | — | — | 5.4 | — | 5.5 | — | 5.5 | — |
| Isobutane | — | — | — | — | 3.5 | — | 3.6 | — | 3.6 | — |
| Pyrolysis Gas | — | — | — | — | 0.1 | — | — | — | — | — |
| Fuel Oil | — | — | — | — | — | — | — | — | — | — |
| Total | 1000 | 118.3 | 269 | 156.9 | 123.4 | 4.6 | 128.0 | 17.0 | 97.9 | 47.1 |

| | Stream # | | | | | | | |
|---|---|---|---|---|---|---|---|---|
|  | 409 | 410 | 411 | 412 | 413 | 414 | 415 | 417 | 419 |
|  | Units | | | | | | | | |
|  | KTA | KTA | KTA | KTA | KTA | KTA | KTA | KTA | KTA |
| AXL | — | — | — | — | — | — | — | — | — |
| Hydrogen | — | — | — | — | — | — | — | — | — |
| Fuel Gas | — | — | 3.6 | — | — | — | — | — | — |
| Methanol | — | — | — | — | — | — | — | — | — |
| MTBE | — | — | — | — | — | — | — | — | — |
| Ethylene | 13.5 | — | — | 282.5 | — | — | — | — | — |
| Propene | — | 37.9 | — | — | 194.8 | — | — | — | — |
| Butadiene | — | — | — | — | — | — | — | — | — |

TABLE 6-continued

Modeling Data for System of FIG. 6 with the
AXL Naphtha Feed According to Example 3.

| | | | | | | | | | |
|---|---|---|---|---|---|---|---|---|---|
| Isobutene | — | — | 11.0 | — | — | — | — | — | — |
| 1-Butene | — | — | 5.5 | — | — | — | — | — | — |
| 2-Butene | — | — | 11.8 | — | — | — | — | — | — |
| n-Butane | — | — | 5.5 | — | — | — | — | — | — |
| Isobutane | — | — | 3.6 | — | — | — | — | — | — |
| Pyrolysis Gas | — | — | — | — | — | — | 242.4 | — | — |
| Fuel Oil | — | — | — | — | — | 5.5 | — | 90.0 | 95.5 |
| Total | 13.5 | 37.9 | 41.1 | 282.5 | 194.8 | 5.5 | 242.4 | 90.0 | 95.5 |

As shown in Table 6, the system 100 with the dual catalyst metathesis system 160 integrated with the steam cracking system 110 produces a total of 282.5 KTA ethylene and 194.8 KTA propene. The production of 282.5 KTA ethylene from system 100 represents a greater than 5% increase in the production of ethylene compared to steam cracking by itself (Table 3), and the production of 194.8 KTA propene from system 100 represents a 24% increase in the product of propene compared to steam cracking by itself (Table 3).

Example 4

Integrated Steam Cracking and Metathesis Process for Gas Condensate Feed

In Example 4, the system 100 of FIG. 6 integrating a steam cracking system 110 with a metathesis system 160 for upgrading a hydrocarbon feed 400 comprising a gas condensate to ethylene and propylene is modeled. AspenPlus® 9 chemical process modeling software (AspenTech) is used to model the steam cracking system 110, selective hydrogenation unit 130, and isobutene removal unit 150 of system 100 according to the description previously provided in Example 3. The gas condensate for the hydrocarbon feed 400 is Khuff gas condensate recovered from natural gas extracted from the Khuff reservoir in Saudi Arabia. Characteristics for the Khuff gas condensate for Example 4 are provided in Table 1.

The metathesis system 160 was tested using a bench scale reactor having the metathesis catalyst in the metathesis reaction zone and the cracking catalyst in the cracking reaction zone downstream of the metathesis reaction zone. The feed to the bench scale metathesis reactor was synthesized using the composition modeled for the metathesis feed 407 and provided below in Table 8. In particular, the metathesis feed included 55.7 wt. % 1-butene, 32.9 wt. % 2-butene, 5.2 wt. % n-butane, and 3.4 wt. % isobutane based on the total weight of the metathesis feed. The metathesis reaction effluent was analyzed to determine the composition. The mass balance information for the steam cracking system 110, selective hydrogenation unit 130, isobutene removal unit 150, and metathesis system based on using the Khuff gas condensate for the hydrocarbon feed 400 is provided in Table 7.

TABLE 7

Mass Balance Information for Modeling the Unit Operations of FIG. 6 for Example 4

| | Yields | | | | | | | |
|---|---|---|---|---|---|---|---|---|
| | Steam Cracking System | | Selective Hydrogenation Unit | | Isobutene Removal Unit | | Metathesis System | |
| Feed | wt. % | KTA | wt. % | KTA | wt. % | KTA | wt. % | KTA |
| KGC | 100 | 1000 | — | — | — | — | — | — |
| Hydrogen | — | — | 4 | 4 | — | — | 3 | 2 |
| Cracking C4 Eff | — | — | 96 | 95 | — | — | — | — |
| Hydrogenation Eff. | — | — | — | — | 89 | 99 | — | — |
| Methanol | — | — | — | — | 11 | 12 | — | — |
| Metathesis Feed | — | — | — | — | — | — | 97 | 75 |
| Total Feed | 100 | 1000 | 100 | 99 | 100 | 107 | 100 | 77 |
| Component Yields in Effluent | | | | | | | | |
| Off-gas | NA | NA | NA | NA | NA | NA | 1 | 1 |
| Hydrogen | 2.1 | 21 | 2.2 | 2.2 | 1.9 | 2.2 | 3 | 2.2 |
| Methane | 10.9 | 109 | 0 | 0 | 0 | 0 | 0 | 0 |
| Ethylene | 27.8 | 278 | 0 | 0 | 0 | 0 | 14 | 11 |
| Propylene | 14.5 | 145 | 0 | 0 | 0 | 0 | 39 | 30 |
| 1,3-butadiene | 9.5 | 95 | 0 | 0 | 0 | 0 | 0 | 0 |
| Isobutene | | | 22 | 22 | 0 | 0 | 11 | 9 |
| 1-Butene | | | 43 | 43 | 39 | 43 | 6 | 4 |
| 2-Butene | | | 26 | 25 | 23 | 25 | 12 | 9 |
| n-Butane | | | 4 | 4 | 4 | 4 | 5 | 4 |
| Isobutane | | | 3 | 3 | 2 | 3 | 3 | 3 |
| MTBE | NA | NA | NA | NA | 31 | 34 | 0 | 0 |

TABLE 7-continued

Mass Balance Information for Modeling the Unit Operations of FIG. 6 for Example 4

| | Yields | | | | | | | |
|---|---|---|---|---|---|---|---|---|
| | Steam Cracking System | | Selective Hydrogenation Unit | | Isobutene Removal Unit | | Metathesis System | |
| Feed | wt. % | KTA | wt. % | KTA | wt. % | KTA | wt. % | KTA |
| C5+ | NA | NA | 0 | 0 | 0 | 0 | 6 | 4 |
| Pyrolysis Gas | 17.3 | 173 | NA | NA | NA | NA | NA | NA |
| Fuel Oil | 17.9 | 179 | NA | NA | NA | NA | NA | NA |
| Total Yield | 100 | 1000 | 100 | 99 | 100 | 111 | 100 | 77 |

KTA stands for kilotons per annum.
Weight percent (wt. %) for the feed to each unit operation is based on the total weight of all feed streams introduced to that unit operation.
Weight percent (wt. %) for the Component Yields in Effluent from one of the unit operations are based on the total weight of the effluent passed out of that unit operation.

As described previously in Example 3, the metathesis ethylene effluent 409 is combined with the cracking ethylene effluent 402 to produce a system ethylene effluent 412. The metathesis propene effluent 410 is combined with the cracking propene effluent 403 to produce a system propene effluent. The metathesis C5+ effluent 414 is combined with the fuel oil effluent 417 from the steam cracking system 110 to produce a system fuel oil effluent 419. The modeling data for the system 100 of FIG. 6 with the Khuff gas condensate for the hydrocarbon feed is provided in Table 8.

TABLE 8

Modeling Data for System of FIG. 6 with Khuff Gas Condensate (KGC) Feed According to Example 4.

| | Stream # | | | | | | | | | |
|---|---|---|---|---|---|---|---|---|---|---|
| | 400 | 401 | 402 | 403 | 404 | 420 | 405 | 406 | 407 | 408 |
| | | | | | Units | | | | | |
| | KTA | KTA | KTA | KTA | KTA | KTA | KTA | KTA | KTA | KTA |
| KGC | 1000 | — | — | — | — | — | — | — | — | — |
| Hydrogen | — | — | — | — | — | 3.8 | 2.2 | — | 2 | — |
| Fuel Gas | — | 130.2 | — | — | — | — | — | — | — | — |
| Methanol | — | — | — | — | — | — | — | 12.4 | — | — |
| MTBE | — | — | — | — | — | — | — | — | — | 34 |
| Ethylene | — | — | 278.4 | — | — | — | — | — | — | — |
| Propene | — | — | — | 145.2 | — | — | — | — | — | — |
| Butadiene | — | — | — | — | 46.7 | — | 0.0 | — | — | — |
| Isobutene | — | — | — | — | 21.5 | — | 21.9 | — | — | — |
| 1-Butene | — | — | — | — | 13.2 | — | 42.8 | — | 42.8 | — |
| 2-Butene | — | — | — | — | 7.0 | — | 25.3 | — | 25.3 | — |
| n-Butane | — | — | — | — | 3.9 | — | 4.0 | — | 4.0 | — |
| Isobutane | — | — | — | — | 2.6 | — | 2.6 | — | 2.6 | — |
| Pyrolysis Gas | — | — | — | — | 0.1 | — | — | — | — | — |
| Fuel Oil | — | — | — | — | — | — | — | — | — | — |
| Total | 1000 | 130.2 | 278.4 | 145.2 | 95.0 | 3.8 | 98.8 | 12.4 | 76.9 | 34.2 |

| | Stream # | | | | | | | |
|---|---|---|---|---|---|---|---|---|
| | 409 | 410 | 411 | 412 | 413 | 414 | 415 | 417 | 419 |
| | | | | | Units | | | | |
| | KTA | KTA | KTA | KTA | KTA | KTA | KTA | KTA | KTA |
| KGC | — | — | — | — | — | — | — | — | — |
| Hydrogen | — | — | — | — | — | — | — | — | — |
| Fuel Gas | — | — | 3.1 | — | — | — | — | — | — |
| Methanol | — | — | — | — | — | — | — | — | — |
| MTBE | — | — | — | — | — | — | — | — | — |
| Ethylene | 10.6 | — | — | 289.0 | — | — | — | — | — |
| Propene | — | 29.9 | — | — | 175.1 | — | — | — | — |
| Butadiene | — | — | — | — | — | — | — | — | — |
| Isobutene | — | — | 8.7 | — | — | — | — | — | — |
| 1-Butene | — | — | 4.4 | — | — | — | — | — | — |
| 2-Butene | — | — | 9.3 | — | — | — | — | — | — |
| n-Butane | — | — | 4.0 | — | — | — | — | — | — |

TABLE 8-continued

Modeling Data for System of FIG. 6 with Khuff Gas
Condensate (KGC) Feed According to Example 4.

| | | | | | | | | | |
|---|---|---|---|---|---|---|---|---|---|
| Isobutane | — | — | 2.6 | — | — | — | — | — | — |
| Pyrolysis Gas | — | — | — | — | — | — | 172.7 | — | — |
| Fuel Oil | — | — | — | — | — | 4.3 | — | 178.6 | 182.9 |
| Total | 10.6 | 29.9 | 32.0 | 289.0 | 175.1 | 4.3 | 172.7 | 178.6 | 182.9 |

As shown in Table 8, for processing the Khuff gas condensate, the system 100 with the dual catalyst metathesis system 160 integrated with the steam cracking system 110 produces a total of 289.0 KTA ethylene and 175.1 KTA propene. The production of 289.0 KTA ethylene from system 100 represents a 4% increase in the production of ethylene compared to steam cracking by itself (Table 4), and the production of 175.1 KTA propene from system 100 represents a 20% increase in the product of propene compared to steam cracking by itself.

Example 5

Integrated Steam Cracking and Metathesis Process For Naphtha Feed: Single Catalyst Metathesis System In Example 5, the system 100 of FIG. 6 integrating a steam cracking system 110 with a metathesis system 160 for upgrading a hydrocarbon feed 400 comprising naphtha to ethylene and propylene is modeled with a metathesis system that include the metathesis catalyst only and does not include the cracking catalyst. The naphtha for the hydrocarbon feed for Example 5 is the AXL naphtha stream from Table 2. In Example 5, the steam cracking system 110, selective hydrogenation unit 130, and isobutene removal unit 150 are modeled using the same conditions and assumptions described in relation to Example 3.

The metathesis system 160 for Example 5 includes only the metathesis reaction zone comprising the metathesis catalyst and does not include the cracking catalyst. The metathesis system was tested using a bench scale reactor having the metathesis catalyst only. The feed to the bench scale metathesis reactor was synthesized using the composition modeled for the metathesis feed 407 and provided below in Table 10. In particular, the metathesis feed included 55.6 wt. % 1-butene, 32.7 wt. % 2-butene, 5.6 wt. % n-butane, and 3.7 wt. % isobutane based on the total weight of the metathesis feed. The metathesis reaction effluent was analyzed to determine the composition. The metathesis system 160 produced a total conversion of butene of 80% with a propylene selectivity of 46% and an ethylene selectivity of 14.5%. The metathesis reaction effluent is separated into a metathesis ethylene effluent 409, a metathesis propene effluent 410, a metathesis C4 effluent 411, and a metathesis C5+ effluent 414. Separation of the metathesis reaction effluent into the various effluents 409, 410, 411, and 414 is assumed to be 100% efficient. The mass balances for each of the steam cracking system 110, the selective hydrogenation unit 130, the isobutene removal unit 150, and the metathesis system 160 for Example 5 are provided in Table 9.

TABLE 9

Mass Balance Information for Modeling the Unit Operations of FIG. 6 for Example 5

| | Yields | | | | | | | |
|---|---|---|---|---|---|---|---|---|
| | Steam Cracking System | | Selective Hydrogenation Unit | | Isobutene Removal Unit | | Metathesis System | |
| Feed | wt. % | KTA | wt. % | KTA | wt. % | KTA | wt. % | KTA |
| AXL | 100 | 1000 | — | — | — | — | — | — |
| Hydrogen | — | — | 4 | 5 | | | 2 | 2 |
| Cracking C4 Eff | — | — | 96 | 123 | — | — | — | — |
| Hydrogenation Eff. | — | — | — | — | 88 | 128 | — | — |
| Methanol | — | — | — | — | 12 | 17 | — | — |
| Metathesis Feed | — | — | — | — | — | — | 98 | 95 |
| Total Feed | 100 | 1000 | 100 | 128 | 100 | 140 | 100 | 98 |
| | | | Component Yields in Effluent | | | | | |
| Off-gas | NA | NA | NA | NA | NA | NA | 1 | 1 |
| Hydrogen | 0.9 | 9 | 2.0 | 2.5 | 1.7 | 2.4 | 2 | 2.4 |
| Methane | 10.9 | 109 | 0 | 0 | 0 | 0 | NA | NA |
| Ethylene | 26.9 | 269 | 0 | 0 | 0 | 0 | 4 | 4 |
| Propylene | 15.7 | 157 | 0 | 0 | 0 | 0 | 24 | 23 |
| 1,3-butadiene | 12.3 | 123 | 0 | 0 | 0 | 0 | 0 | 0 |
| Isobutene | | | 23 | 30 | 0 | 0 | 2 | 2 |
| 1-Butene | | | 42 | 54 | 38 | 54 | 11 | 10 |
| 2-Butene | | | 25 | 32 | 22 | 32 | 26 | 25 |
| n-Butane | | | 4 | 5 | 4 | 5 | 6 | 5 |
| Isobutane | | | 3 | 4 | 2 | 4 | 4 | 4 |
| MTBE | NA | N/A | NA | NA | 32 | 47 | 0 | 0 |

TABLE 9-continued

Mass Balance Information for Modeling the Unit Operations of FIG. 6 for Example 5

| Feed | Yields | | | | | | | |
|---|---|---|---|---|---|---|---|---|
| | Steam Cracking System | | Selective Hydrogenation Unit | | Isobutene Removal Unit | | Metathesis System | |
| | wt. % | KTA | wt. % | KTA | wt. % | KTA | wt. % | KTA |
| C5+ | NA | NA | 0 | 0 | 0 | 0 | 21 | 20 |
| Pyrolysis Gas | 24.2 | 242 | NA | NA | NA | NA | NA | NA |
| Fuel Oil | 9 | 90 | NA | NA | NA | NA | NA | NA |
| Total Yield | 100 | 1000 | 100 | 128 | 1 | 145 | 100 | 98 |

KTA stands for kilotons per annum.
Weight percent (wt. %) for the feed to each unit operation is based on the total weight of all feed streams introduced to that unit operation.
Weight percent (wt. %) for the Component Yields in Effluent from one of the unit operations are based on the total weight of the effluent passed out of that unit operation.

The metathesis ethylene effluent 409 is combined with the cracking ethylene effluent 402 to produce a system ethylene effluent 412. The metathesis propene effluent 410 is combined with the cracking propene effluent 403 to produce a system propene effluent. The metathesis C5+ effluent 414 is combined with the fuel oil effluent 417 from the steam cracking system 110 to produce a system fuel oil effluent 419. The modeling data for the system 100 of FIG. 6 with the naphtha hydrocarbon feed according to Example 5 is provided in Table 10.

TABLE 10

Modeling Data for System of FIG. 6 with the AXL Naphtha Feed According to Example 5.

| | Stream # | | | | | | | | | |
|---|---|---|---|---|---|---|---|---|---|---|
| | 400 | 401 | 402 | 403 | 404 | 420 | 405 | 406 | 407 | 408 |
| | | | | | Units | | | | | |
| | KTA | KTA | KTA | KTA | KTA | KTA | KTA | KTA | KTA | KTA |
| AXL | 1000 | — | — | — | — | — | — | — | — | — |
| Hydrogen | — | — | — | — | — | 4.6 | 2.5 | — | 2 | — |
| Fuel Gas | — | 118.3 | — | — | — | — | — | — | — | — |
| Methanol | — | — | — | — | — | — | — | 17.0 | — | — |
| MTBE | — | — | — | — | — | — | — | — | — | 47.1 |
| Ethylene | — | — | 269 | — | — | — | — | — | — | — |
| Propene | — | — | — | 156.9 | — | — | — | — | — | — |
| Butadiene | — | — | — | — | 57.0 | — | — | — | — | — |
| Isobutene | — | — | — | — | 29.5 | — | 30.1 | — | — | — |
| 1-Butene | — | — | — | — | 18.2 | — | 54.3 | — | 54.4 | — |
| 2-Butene | — | — | — | — | 9.6 | — | 31.9 | — | 32.0 | — |
| n-Butane | — | — | — | — | 5.4 | — | 5.5 | — | 5.5 | — |
| Isobutane | — | — | — | — | 3.5 | — | 3.6 | — | 3.6 | — |
| Pyrolysis Gas | — | — | — | — | 0.1 | — | — | — | — | — |
| Fuel Oil | — | — | — | — | — | — | — | — | — | — |
| Total | 1000 | 118.3 | 269 | 156.9 | 123.4 | 4.6 | 127.9 | 17.0 | 97.9 | 47.1 |

| | Stream # | | | | | | | |
|---|---|---|---|---|---|---|---|---|
| | 409 | 410 | 411 | 412 | 413 | 414 | 415 | 417 | 419 |
| | | | | | Units | | | | |
| | KTA | KTA | KTA | KTA | KTA | KTA | KTA | KTA | KTA |
| AXL | — | — | — | — | — | — | — | — | — |
| Fuel Gas | — | — | 3.8 | — | — | — | — | — | — |
| Methanol | — | — | — | — | — | — | — | — | — |
| MTBE | — | — | — | — | — | — | — | — | — |
| Ethylene | 3.8 | — | — | 272.8 | — | — | — | — | — |
| Propene | — | 23.2 | — | — | 180.1 | — | — | — | — |
| Butadiene | — | — | — | — | — | — | — | — | — |
| Isobutene | — | — | 2.1 | — | — | — | — | — | — |
| 1-Butene | — | — | 10.5 | — | — | — | — | — | — |
| 2-Butene | — | — | 25.1 | — | — | — | — | — | — |

TABLE 10-continued

| Modeling Data for System of FIG. 6 with the AXL Naphtha Feed According to Example 5. | | | | | | | | | |
|---|---|---|---|---|---|---|---|---|---|
| n-Butane | — | — | 5.5 | — | — | — | — | — | — |
| Isobutane | — | — | 3.6 | — | — | — | — | — | — |
| Pyrolysis Gas | — | — | — | — | — | — | 242.4 | — | — |
| Fuel Oil | — | — | — | — | — | 20.4 | — | 90.0 | 110.5 |
| Total | 3.8 | 23.2 | 50.5 | 272.8 | 180.1 | 20.4 | 242.4 | 90.0 | 110.5 |

As shown in Table 10, the system 100 with the single catalyst metathesis system integrated with the steam cracking system 110 according to Example 5 produces a total of 272.8 KTA ethylene and 180.1 KTA propene. The production ethylene in Example 5 was 3% less compared to the ethylene produced in Example 3 with the two-catalyst metathesis system integrated with the steam cracking system 110. The production of propene in Example 5 was 7.4% less compared to the propene produced in Example 3. Thus, comparison of Example 3 and Example 5 demonstrates that integrating the steam cracking system 110 with the dual catalyst metathesis system with the metathesis catalyst and cracking catalyst, as in Example 3, can increase the selectivity and yield of propene and ethylene from the process.

Example 6

Integrated Steam Cracking and Metathesis Process for Gas Condensate Feed: Single Catalyst Metathesis System In Example 6, the system 100 of FIG. 6 integrating a steam cracking system 110 with a metathesis system 160 for upgrading a hydrocarbon feed 400 comprising gas condensate feed to ethylene and propylene is modeled with a metathesis system that includes the metathesis catalyst only and does not include the cracking catalyst. The gas condensate feed for the hydrocarbon feed 400 is the Khuff gas condensate provided in Table 1. In Example 6, the steam cracking system 110, selective hydrogenation unit 130, and isobutene removal unit 150 are modeled using the same conditions and assumptions described in relation to Example 4.

The metathesis system 160 was tested using a bench scale reactor having the metathesis catalyst in the metathesis reaction zone and the cracking catalyst in the cracking reaction zone downstream of the metathesis reaction zone. The feed to the bench scale metathesis reactor was synthesized using the composition modeled for the metathesis feed 407 and provided below in Table 8. In particular, the metathesis feed included 55.7 wt. % 1-butene, 32.9 wt. % 2-butene, 5.2 wt. % n-butane, and 3.4 wt. % isobutane based on the total weight of the metathesis feed. The metathesis reaction effluent was analyzed to determine the composition. The metathesis reaction effluent is separated into a metathesis ethylene effluent 409, a metathesis propene effluent 410, a metathesis C4 effluent 411, and a metathesis C5+ effluent 414. Separation of the metathesis reaction effluent into the various effluents 409, 410, 411, and 414 is assumed to be 100% efficient. The mass balances for each of the steam cracking system 110, the selective hydrogenation unit 130, the isobutene removal unit 150, and the metathesis system 160 for Example 6 are provided in Table 11.

TABLE 11

| Mass Balance Information for Modeling the Unit Operations of FIG. 6 for Example 6 | | | | | | | | |
|---|---|---|---|---|---|---|---|---|
| | Yields | | | | | | | |
| | Steam Cracking System | | Selective Hydrogenation Unit | | Isobutene Removal Unit | | Metathesis System | |
| Feed | wt. % | KTA | wt. % | KTA | wt. % | KTA | wt. % | KTA |
| KGC | 100 | 1000 | — | — | — | — | — | — |
| Hydrogen | — | — | 4 | 4 | — | — | 3 | 2 |
| Cracking C4 Eff | — | — | 96 | 95 | — | — | — | — |
| Hydrogenation Eff. | — | — | — | — | 89 | 99 | — | — |
| Methanol | — | — | — | — | 11 | 12 | — | — |
| Metathesis Feed | — | — | — | — | — | — | 97 | 75 |
| Total Feed | 100 | 1000 | 100 | 99 | 100 | 107 | 100 | 77 |
| Component Yields in Effluent | | | | | | | | |
| Off-gas | NA | NA | NA | NA | NA | NA | 1 | 1 |
| Hydrogen | 2.1 | 21 | 2.2 | 2.2 | 1.9 | 2.2 | 3 | 2.2 |
| Methane | 10.9 | 109 | 0 | 0 | 0 | 0 | 0 | 0 |
| Ethylene | 27.8 | 278 | 0 | 0 | 0 | 0 | 4 | 3 |
| Propylene | 14.5 | 145 | 0 | 0 | 0 | 0 | 24 | 18 |
| 1,3-butadiene | 9.5 | 95 | 0 | 0 | 0 | 0 | 0 | 0 |
| Isobutene | | | 22 | 22 | 0 | 0 | 2 | 2 |
| 1-Butene | | | 43 | 43 | 39 | 43 | 11 | 8 |
| 2-Butene | | | 26 | 25 | 23 | 25 | 26 | 20 |
| n-Butane | | | 4 | 4 | 4 | 4 | 5 | 4 |
| Isobutane | | | 3 | 3 | 2 | 3 | 3 | 3 |
| MTBE | NA | NA | NA | NA | 31 | 34 | 0 | 0 |

TABLE 11-continued

Mass Balance Information for Modeling the Unit Operations of FIG. 6 for Example 6

| Feed | Yields | | | | | | | |
|---|---|---|---|---|---|---|---|---|
| | Steam Cracking System | | Selective Hydrogenation Unit | | Isobutene Removal Unit | | Metathesis System | |
| | wt. % | KTA | wt. % | KTA | wt. % | KTA | wt. % | KTA |
| C5+ | NA | NA | 0 | 0 | 0 | 0 | 21 | 16 |
| Pyrolysis Gas | 17.3 | 173 | NA | NA | NA | NA | NA | NA |
| Fuel Oil | 17.9 | 179 | NA | NA | NA | NA | NA | NA |
| Total Yield | 100 | 1000 | 100 | 99 | 100 | 111 | 100 | 77 |

KTA stands for kilotons per annum.
Weight percent (wt. %) for the feed to each unit operation is based on the total weight of all feed streams introduced to that unit operation.
Weight percent (wt. %) for the Component Yields in Effluent from one of the unit operations are based on the total weight of the effluent passed out of that unit operation.

As described previously in Examples 2-5, the metathesis ethylene effluent 409 is combined with the cracking ethylene effluent 402 to produce a system ethylene effluent 412. The metathesis propene effluent 410 is combined with the cracking propene effluent 403 to produce a system propene effluent. The metathesis C5+ effluent 414 is combined with the fuel oil effluent 417 from the steam cracking system 110 to produce a system fuel oil effluent 419. The modeling data for the system 100 of FIG. 6 with the Khuff gas condensate for the hydrocarbon feed according to Example 6 is provided in Table 12.

TABLE 12

Modeling Data for the System of FIG. 6 with Khuff Gas Condensate (KGC) Feed.

| | Stream # | | | | | | | | | |
|---|---|---|---|---|---|---|---|---|---|---|
| | 400 | 401 | 402 | 403 | 404 | 420 | 405 | 406 | 407 | 408 |
| | KTA | KTA | KTA | KTA | KTA | KTA | KTA | KTA | KTA | KTA |
| KGC | 1000 | — | — | — | — | — | — | — | — | — |
| Hydrogen | — | — | — | — | — | 3.8 | 2.2 | — | 2.2 | — |
| Fuel Gas | — | 130.2 | — | — | — | — | — | — | — | — |
| Methanol | — | — | — | — | — | — | — | 12.4 | — | — |
| MTBE | — | — | — | — | — | — | — | — | — | 34.2 |
| Ethylene | — | — | 278.4 | — | — | — | — | — | — | — |
| Propene | — | — | — | 145.2 | — | — | — | — | — | — |
| Butadiene | — | — | — | — | 46.7 | — | 0.0 | — | — | — |
| Isobutene | — | — | — | — | 21.5 | — | 21.9 | — | — | — |
| 1-Butene | — | — | — | — | 13.2 | — | 42.8 | — | 42.8 | — |
| 2-Butene | — | — | — | — | 7.0 | — | 25.3 | — | 25.3 | — |
| n-Butane | — | — | — | — | 3.9 | — | 4.0 | — | 4.0 | — |
| Isobutane | — | — | — | — | 2.6 | — | 2.6 | — | 2.6 | — |
| Pyrolysis Gas | — | — | — | — | 0.1 | — | — | — | — | — |
| Fuel Oil | — | — | — | — | — | — | — | — | — | — |
| Total | 1000 | 130.2 | 278.4 | 145.2 | 95.0 | 3.8 | 98.8 | 12.4 | 76.9 | 34.2 |

| | Stream # | | | | | | | |
|---|---|---|---|---|---|---|---|---|
| | 409 | 410 | 411 | 412 | 413 | 414 | 415 | 417 | 419 |
| | KTA | KTA | KTA | KTA | KTA | KTA | KTA | KTA | KTA |
| KGC | — | — | — | — | — | — | — | — | — |
| Hydrogen | — | — | — | — | — | — | — | — | — |
| Fuel Gas | — | — | 3.2 | — | — | — | — | — | — |
| Methanol | — | — | — | — | — | — | — | — | — |
| MTBE | — | — | — | — | — | — | — | — | — |
| Ethylene | 3.0 | — | — | 281.4 | — | — | — | — | — |
| Propene | — | 18.2 | — | — | 163.4 | — | — | — | — |
| Butadiene | — | — | — | — | — | — | — | — | — |
| Isobutene | — | — | 1.7 | — | — | — | — | — | — |
| 1-Butene | — | — | 8.2 | — | — | — | — | — | — |
| 2-Butene | — | — | 19.8 | — | — | — | — | — | — |
| n-Butane | — | — | 4.0 | — | — | — | — | — | — |

TABLE 12-continued

Modeling Data for the System of FIG. 6 with Khuff Gas Condensate (KGC) Feed.

| | | | | | | | | | |
|---|---|---|---|---|---|---|---|---|---|
| Isobutane | — | — | 2.6 | — | — | — | — | — | — |
| Pyrolysis Gas | — | — | — | — | — | — | 172.7 | — | — |
| Fuel Oil | — | — | — | — | — | 16.1 | — | 178.6 | 194.7 |
| Total | 3.0 | 18.2 | 39.5 | 281.4 | 163.4 | 16.1 | 172.7 | 178.6 | 194.7 |

As shown in Table 12, the system 100 with the single catalyst metathesis system integrated with the steam cracking system 110 for processing Khuff gas condensate according to Example 6 produces a total of 281.4 KTA ethylene and 163.4 KTA propene. The production of ethylene in Example 6 was 2.6% less compared to the ethylene produced in Example 4 with the two-catalyst metathesis system integrated with the steam cracking system 110. The production of propene in Example 6 was 6.5% less compared to the propene produced in Example 4. Thus, comparison of Example 4 and Example 6 demonstrates that, for gas condensate feeds, integrating the steam cracking system 110 with the dual catalyst metathesis system with the metathesis catalyst and cracking catalyst, as in Example 4, can increase the selectivity and yield of propene and ethylene from the process.

A first aspect of the present disclosure may include a process for producing olefins. The process may include contacting a hydrocarbon feed with at least steam at a temperature of from 700° C. to 900° C. The contacting may cause at least a portion of the hydrocarbon feed to undergo steam cracking to form a cracking reaction effluent comprising at least butenes. The process may further include separating the cracking reaction effluent to produce at least a cracking C4 effluent that includes at least normal butenes, isobutene, and 1,3-butadiene. The process may further include subjecting the cracking C4 effluent to selective hydrogenation to produce a hydrogenation effluent. Selective hydrogenation may cause at least a portion of the 1,3-butadiene in the cracking C4 effluent to react to form normal butenes. The process may further include removing isobutene from the hydrogenation effluent to produce a metathesis feed comprising at least normal butenes and contacting at least a portion of the metathesis feed with a metathesis catalyst and a cracking catalyst directly downstream of the metathesis catalyst to produce a metathesis reaction effluent. Contacting the metathesis feed with the metathesis catalyst may cause metathesis of normal butenes to produce at least ethylene, propene, and C5+ olefins, and contacting with the cracking catalyst may cause at least a portion of the C5+ olefins produced through metathesis to undergo cracking reactions to produce propene, ethylene, or both. The metathesis reaction effluent may include at least ethylene, propene, or both.

A second aspect of the present disclosure may include the first aspect, in which the hydrocarbon feed may comprise naphtha, a gas condensate, or both.

A third aspect of the present disclosure may include any one of the first or second aspects, further comprising separating the metathesis reaction effluent into a metathesis C5+ effluent and at least one olefin-containing effluent. The olefin-containing effluent may comprise at least one of ethylene, propylene, or normal butenes. The process may further include passing the metathesis C5+ effluent back into contact with the hydrocarbon feed and steam at the temperature of from 700° C. to 900° C., where contacting may cause at least a portion of the metathesis C5+ effluent to undergo steam cracking.

A fourth aspect of the present disclosure may include the third aspect, in which passing the metathesis C5+ effluent back into contact with the hydrocarbon feed and steam may comprise hydrotreating the metathesis C5+ effluent to produce a hydrotreated effluent and passing the hydrotreated effluent into contact with the hydrocarbon feed and steam at the temperature of from 700° C. to 900° C. The contacting of the hydrotreated effluent with the hydrocarbon feed and steam may cause at least a portion of the hydrotreated effluent to undergo steam cracking.

A fifth aspect of the present disclosure may include any one of the first through fourth aspects, comprising separating the metathesis reaction effluent into a metathesis C5+ effluent, a metathesis C4 effluent, a metathesis propene effluent, and a metathesis ethylene effluent.

A sixth aspect of the present disclosure may include the fifth aspect, further comprising, after separating, passing at least a portion of the metathesis C4 effluent back into contact with the metathesis catalyst, where contact may cause further metathesis of normal butenes in the metathesis C4 effluent to produce the metathesis reaction effluent.

A seventh aspect of the present disclosure may include the fifth aspect, further comprising passing at least a portion of the metathesis C4 effluent into contact with the cracking C4 effluent, hydrogen, and a selective hydrogenation catalyst and contacting the portion of the metathesis C4 effluent with the hydrogen in the presence of the selective hydrogenation catalyst, where contacting may cause at least a portion of 1,3-butadiene in the portion of the metathesis C4 effluent to undergo a selective hydrogenation reaction.

An eighth aspect of the present disclosure may include any one of the fifth through seventh aspects, further comprising passing at least a portion of the metathesis ethylene effluent back into contact with the metathesis catalyst.

A ninth aspect of the present disclosure may include any one of the fifth through seventh aspects, in which the metathesis ethylene effluent may not be passed back into contact with the metathesis catalyst and no supplemental ethylene is introduced into contact with the metathesis catalyst.

A tenth aspect of the present disclosure may include any one of the first through ninth aspects, in which subjecting the cracking C4 effluent to selective hydrogenation may comprise contacting the cracking C4 effluent with hydrogen in the presence of a selective hydrogenation catalyst under conditions sufficient to cause at least a portion of the 1,3-butadiene in the cracking C4 effluent to undergo hydrogenation to produce a hydrogenation effluent comprising a greater concentration of normal butenes compared to the concentration of normal butenes in the cracking C4 effluent.

An eleventh aspect of the present disclosure may include the tenth aspect, in which the hydrogenation effluent may have a concentration of 1,3-butadiene less than a concentration of 1,3-butadiene in the cracking C4 effluent.

A twelfth aspect of the present disclosure may include any one of the first through eleventh aspects, in which removing isobutene may comprise contacting the hydrogenation effluent with methanol under reaction conditions sufficient to convert at least a portion of the isobutene in the hydrogenated C4 effluent to methyl tert-butyl ether to produce an MTBE reaction product and separating at least a portion of the methyl tert-butyl ether from the MTBE reaction product to produce an MTBE effluent comprising the methyl tert-butyl ether and the metathesis feed comprising butene.

A thirteenth aspect of the present disclosure may include the twelfth aspect, further comprising recovering at least a portion of the methyl-tert-butyl ether from the MTBE effluent.

A fourteenth aspect of the present disclosure may include the twelfth or thirteenth aspects, further comprising passing at least a portion of the MTBE effluent back into the hydrocarbon feed and subjecting the portion of the MTBE effluent to steam cracking.

A fifteenth aspect of the present disclosure may include the fourteenth aspect, further comprising contacting the MTBE effluent with a cracking catalyst under conditions sufficient to produce an isobutene effluent, where the contacting may cause at least a portion of the methyl tert-butyl ether in the MTBE effluent to react to form isobutene. The process may further include passing the isobutene effluent back into the hydrocarbon feed and subjecting the isobutene effluent to steam cracking.

A sixteenth aspect of the present disclosure may include any one of the first through fifteenth aspects, comprising separating the cracking reaction effluent into at least the cracking C4 effluent, a cracking ethylene effluent, a cracking propylene effluent, a pyrolysis gas effluent, a fuel gas effluent, and a lesser molecular weight gas effluent.

A seventeenth aspect of the present disclosure may include any one of the first through sixteenth aspects, comprising contacting the hydrocarbon feed with the steam at the temperature of from 700° C. to 900° C. for a residence time of from 0.05 seconds to 2 seconds and at a mass ratio of steam to hydrocarbon of from 0.3:1 to 2:1.

An eighteenth aspect of the present disclosure may include a process for producing olefins, the process including contacting a hydrocarbon feed with steam in a steam cracking system at a temperature sufficient to produce a cracking reaction effluent and separating the cracking reaction effluent to produce at least a cracking C4 effluent comprising normal butenes, isobutene, and 1,3-butadiene. The process may further include subjecting the cracking C4 effluent to selective hydrogenation in a selective hydrogenation unit to produce a hydrogenation effluent. Selective hydrogenation may cause at least a portion of the 1,3-butadiene in the cracking C4 effluent to react to form normal butenes. The process may further include passing the hydrogenation effluent to an isobutene removal unit, removing isobutene from the hydrogenation effluent in the isobutene removal unit to produce at least a metathesis feed comprising normal butenes, passing at least a portion of the metathesis feed to a metathesis system comprising a metathesis catalyst and a cracking catalyst directly downstream of the metathesis catalyst, and contacting the portion of the metathesis feed with the metathesis catalyst and the cracking catalyst to produce a metathesis reaction effluent. Contacting with the metathesis catalyst may cause metathesis of normal butenes in the metathesis feed to produce at least ethylene, propene, and C5+ olefins, and contacting with the cracking catalyst may cause at least a portion of the C5+ olefins produced through metathesis to undergo cracking reactions to produce ethylene, propene, or both. The metathesis reaction effluent may comprise at least ethylene, propene, or both.

A nineteenth aspect of the present disclosure may include the eighteenth aspect, in which the hydrocarbon feed may comprise a naphtha stream, a gas condensate stream, or both.

A twentieth aspect of the present disclosure may include either one of the eighteenth or nineteenth aspects, in which the metathesis system may comprise a metathesis reaction zone comprising the metathesis catalyst and a cracking reaction zone comprising the cracking catalyst and the cracking reaction zone which may be directly downstream of the metathesis reaction zone.

A twenty-first aspect of the present disclosure may include the twentieth aspect, comprising passing at least a portion of the metathesis feed through the metathesis reaction zone and the cracking reaction zone downstream of the metathesis reaction zone. Contacting the metathesis feed with the metathesis catalyst in the metathesis reaction zone may cause at least a portion of the normal butenes in the metathesis feed to undergo metathesis to produce at least propene and C5+ olefins, and contacting the C5+ olefins with the cracking catalyst in the cracking reaction zone may cause at least a portion of the C5+ olefins to undergo catalytic cracking to produce at least one of ethylene, propene, or both.

A twenty-second aspect of the present disclosure may include either one of the twentieth or twenty-first aspects, where the cracking catalyst may be in contact with the metathesis catalyst.

A twenty-third aspect of the present disclosure may include either one of the twentieth or twenty-first aspects, where the metathesis reaction zone may be in a first reactor, the cracking reaction zone may be in a second reactor directly downstream of the first reactor, and a conduit may fluidly couple the second reactor to the first reactor.

A twenty-fourth aspect of the present disclosure may include any one of the eighteenth through twenty-third aspects, in which the metathesis catalyst may comprise a least one metal oxide deposited on surfaces of a mesoporous silica catalyst support or a mesoporous silica-alumina catalyst support.

A twenty-fifth aspect of the present disclosure may include any one of the eighteenth through twenty-fourth aspects, in which the cracking catalyst may comprise an MFI structured silica-containing catalyst.

A twenty-sixth aspect of the present disclosure may include any one of the eighteenth through twenty-fifth aspects, comprising separating the metathesis reaction effluent into a metathesis ethylene effluent, a metathesis propene effluent, a metathesis C4 effluent, and a metathesis C5+ effluent.

A twenty-seventh aspect of the present disclosure may include the twenty-sixth aspect, further comprising passing at least a portion of the metathesis C5+ effluent back to the steam cracking system.

A twenty-eighth aspect of the present disclosure may include the twenty-seventh aspect, where passing the at least a portion of the metathesis C5+ effluent back to the steam cracking system may comprise hydrotreating the portion of the metathesis C5+ effluent to produce a hydrotreated effluent, passing the hydrotreated effluent back to the steam cracking system, and contacting the hydrotreated effluent with steam at the temperature of from 700° C. to 900° C. in the steam cracking system, where contacting causes at least a portion of the hydrotreated effluent to undergo steam cracking.

A twenty-ninth aspect of the present disclosure may include any one of the twenty-sixth through twenty-eighth aspects, further comprising passing at least a portion of the metathesis C4 effluent back to the metathesis system, the isobutene removal unit, or the selective hydrogenation unit.

A thirtieth aspect of the present disclosure may include any one of the eighteenth through twenty-ninth aspects, further comprising passing at least a portion of the metathesis ethylene effluent back to the metathesis system.

A thirty-first aspect of the present disclosure may include any one of the eighteenth through thirtieth aspects, in which the metathesis system may comprise a metathesis reactor comprising a metathesis reaction zone having the metathesis catalyst and a cracking reaction zone downstream of the metathesis reaction zone and having a cracking catalyst and a supplemental metathesis reactor comprising a supplemental metathesis catalyst. The supplemental metathesis reactor may be operated in parallel with the metathesis reactor. The process may further comprise contacting a first portion of the metathesis feed with the metathesis catalyst and the cracking catalyst in the metathesis reactor to produce the metathesis reaction effluent and contacting a second portion of the metathesis feed and a portion of the metathesis ethylene effluent with the supplemental metathesis catalyst in the supplemental metathesis reactor to produce a supplemental metathesis reaction effluent.

A thirty-second aspect of the present disclosure may include any one of the eighteenth through twenty-ninth aspects, where the metathesis ethylene effluent may not be passed to the metathesis system and no supplemental ethylene may be introduced to the metathesis system.

A thirty-third aspect of the present disclosure may include any one of the eighteenth through thirty-second aspects, in which the selective hydrogenation unit may be downstream of the steam cracking system, the isobutene removal unit may be downstream of the selective hydrogenation unit, and the metathesis system may be downstream of the isobutene removal unit.

A thirty-fourth aspect of the present disclosure may include any one of the eighteenth through thirty-third aspects, where subjecting the cracking C4 effluent to selective hydrogenation may comprise contacting the cracking C4 effluent with hydrogen in the presence of a selective hydrogenation catalyst in the selective hydrogenation unit at reaction conditions sufficient to cause at least a portion of the 1,3-butadiene in the steam cracking C4 effluent to undergo a hydrogenation reaction to produce a hydrogenation effluent having a concentration of 1,3-butadiene less than a concentration of 1,3-butadiene in the cracking C4 effluent.

A thirty-fifth aspect of the present disclosure may include any one of the eighteenth through thirty-fourth aspects, where removing isobutene from the hydrogenation effluent may comprise contacting the hydrogenation effluent with methanol in an MTBE reactor of the isobutene removal unit under reaction conditions sufficient to convert at least a portion of isobutene in the hydrogenation effluent to methyl tert-butyl ether to produce an MTBE reaction product and separating the MTBE reaction product into at least an MTBE effluent and the metathesis feed, the metathesis feed comprising normal butenes.

A thirty-sixth aspect of the present disclosure may include the thirty-fifth aspect, further comprising recovering at least a portion of the methyl-tent-butyl ether from the MTBE effluent.

A thirty-seventh aspect of the present disclosure may include any one of the thirty-fifth or thirty-sixth aspects, further comprising passing at least a portion of the MTBE effluent back to the steam cracking system.

A thirty-eighth aspect of the present disclosure may include the thirty-seventh aspect, further comprising contacting the MTBE effluent with a cracking catalyst under conditions sufficient to produce an isobutene effluent, where the contacting may cause at least a portion of the methyl-tert-butyl ether in the MTBE effluent to react to form isobutene. The process may further include passing the isobutene effluent back to the steam cracking system and contacting the isobutene effluent with steam at the temperature of from 700° C. to 900° C. in the steam cracking system, where contacting may cause at least a portion of the isobutene effluent to undergo steam cracking.

A thirty-ninth aspect of the present disclosure may include any one of the eighteenth through thirty-eighth aspects, comprising separating the cracking reaction effluent to produce the cracking C4 effluent comprising butenes, and one or more of a cracking ethylene effluent, a cracking propene effluent, a fuel oil, a pyrolysis gas, a lesser-molecular weight gas, or combinations of these.

A fortieth aspect of the present disclosure may include the thirty-ninth aspect, in which separating the cracking reaction effluent may comprise passing the cracking reaction effluent to a cracking effluent separation system comprising one or a plurality of separators operable to separate the cracking reaction effluent into the cracking C4 effluent and at least one of the cracking propene effluent, the cracking ethylene effluent, the lesser-molecular weight gas effluent, the fuel oil, the pyrolysis gas, or combinations of these.

A forty-first aspect of the present disclosure may include any one of the eighteenth through fortieth aspects, comprising contacting the hydrocarbon feed with the steam in a pyrolysis zone of the steam cracking system at a temperature of from 700° C. to 900° C., for a residence time of from 0.05 seconds to 2 seconds, and at a mass ratio of steam to hydrocarbon of from 0.3:1 to 2:1.

A forty-second aspect of the present disclosure may include a system for producing olefins. The system may include a steam cracking system that may be operable to contact a hydrocarbon feed with steam at a temperature of from 700° C. to 900° C. to produce at least a cracking C4 effluent comprising normal butenes, isobutene, and 1,3-butadiene. The system may include a selective hydrogenation unit downstream of the steam cracking system. The selective hydrogenation unit may be operable to convert 1,3-butadiene in the cracking C4 effluent from the steam cracking system to normal butenes. The system may further include an isobutene removal unit downstream of the selective hydrogenation unit and a metathesis system downstream of the isobutene removal unit. The metathesis system may comprise a metathesis reaction zone comprising a metathesis catalyst and a cracking reaction zone comprising a cracking catalyst. The cracking reaction zone may be disposed directly downstream of the metathesis reaction zone.

A forty-third aspect of the present disclosure may include the forty-second aspect, where the metathesis system may comprise at least one metathesis reactor operable to contact a metathesis feed from the isobutene removal unit with the metathesis catalyst in the metathesis reaction zone and then the cracking catalyst in the cracking reaction zone.

A forty-fourth aspect of the present disclosure may include either one of the forty-second or forty-third aspects, where the cracking catalyst may be in contact with the metathesis catalyst.

A forty-fifth aspect of the present disclosure may include either one of the forty-second or forty-third aspects, where the metathesis reaction zone may be in a first reactor, the cracking reaction zone may be in a second reactor directly downstream of the first reactor, and a conduit may fluidly couple the second reactor to the first reactor.

A forty-sixth aspect of the present disclosure may include any one of the forty-second through forty-fifth aspects, in which the metathesis catalyst may comprise a least one metal oxide supported on a mesoporous silica catalyst support or a mesoporous silica-alumina catalyst support.

A forty-seventh aspect of the present disclosure may include any one of the forty-second through forty-sixth aspects, in which the cracking catalyst may comprise an MFI structured silica-containing catalyst.

A forty-eighth aspect of the present disclosure may include any one of the forty-second through forty-seventh aspects, in which the metathesis system further comprises a metathesis effluent separation system that may be operable to separate a metathesis reaction effluent into at least a metathesis ethylene effluent, a metathesis propene effluent, a metathesis C4 effluent, and a metathesis C5+ effluent.

A forty-ninth aspect of the present disclosure may include the forty-eighth aspect, further comprising a metathesis C5+ recycle operable to pass at least a portion of the metathesis C5+ effluent back to the steam cracking system.

A fiftieth aspect of the present disclosure may include the forty-ninth aspect, further comprising a hydrotreating unit downstream of the metathesis effluent separation system and upstream of the steam cracking system, the hydrotreating unit operable to hydrotreat the portion of the metathesis C5+ effluent in the metathesis C5+ recycle to produce a hydrotreated effluent.

A fifty-first aspect of the present disclosure may include any one of the forty-eighth through fiftieth aspects, further comprising a metathesis C4 effluent recycle operable to pass at least a portion of the metathesis C4 effluent from the metathesis effluent separation system back to the metathesis system, the isobutene removal unit, or the selective hydrogenation unit.

A fifty-second aspect of the present disclosure may include any one of the forty-eighth through fifty-first aspects, in which the metathesis system may further comprise a supplemental metathesis reactor comprising a supplemental metathesis catalyst and a metathesis ethylene recycle operable to pass at least a portion of the metathesis ethylene effluent to the supplemental metathesis reactor.

A fifty-third aspect of the present disclosure may include any one of the forty-second through fifty-second aspects, in which the selective hydrogenation unit may comprise one or a plurality of selective hydrogenation reactors, each of which comprises a selective hydrogenation catalyst. The selective hydrogenation unit may be operable to contact the cracking C4 effluent with hydrogen in the presence of the selective hydrogenation catalyst at reaction conditions sufficient to convert at least a portion of the 1,3-butadiene in the cracking C4 effluent to normal butenes.

A fifty-fourth aspect of the present disclosure may include any one of the forty-second through fifty-third aspects, in which the isobutene removal unit may comprise an MTBE reactor operable to contact a hydrogenation effluent from the selective hydrogenation unit with methanol at reaction conditions sufficient to convert at least a portion of the isobutene to methyl tert-butyl ether and an MTBE effluent separation system operable to separate an MTBE reactor effluent from the MTBE reactor into at least a metathesis feed and an MTBE effluent.

A fifty-fifth aspect of the present disclosure may include the fifty-fourth aspect, in which the isobutene removal unit may further comprise an MTBE cracking unit downstream of the MTBE effluent separation system, the MTBE cracking unit operable to contact at least a portion of the MTBE effluent with a cracking catalyst to convert at least a portion of the methyl tert-butyl ether in the MTBE effluent back to isobutene.

A fifty-sixth aspect of the present disclosure may include any one of the forty-second through fifty-fifth aspects, in which the steam cracking system comprises a cracking effluent separation unit comprising one or a plurality of separators operable to separate a cracking reaction effluent into a cracking C4 effluent and at least one other cracking effluent.

A fifty-seventh aspect of the present disclosure may include any one of the forty-second through fifty-sixth aspects, further comprising a combined separation system operable to separate a cracking reaction effluent from a steam cracking reactor of the steam cracking system and a metathesis reaction effluent from the metathesis system into at least a C4 stream, a system propene effluent, and a system ethylene effluent.

It should now be understood that various aspects of the systems and processes for producing olefins that include high-severity fluidized catalytic cracking integrated with metathesis are described and such aspects may be utilized in conjunction with various other aspects.

Throughout this disclosure ranges are provided for various processing parameters and operating conditions for the systems and processes for producing olefins and the compositions of various streams and mixtures. It will be appreciated that when one or more explicit ranges are provided the individual values and the sub-ranges formed within the range are also intended to be provided as providing an explicit listing of all possible combinations is prohibitive. For example, a provided range of 1-10 also includes the individual values, such as 1, 2, 3, 4.2, and 6.8, as well as all the ranges that may be formed within the provided bounds, such as 1-8, 2-4, 6-9, and 1.3-5.6.

It is noted that recitations herein of "at least one" component, element, etc., should not be used to create an inference that the alternative use of the articles "a" or "an" should be limited to a single component, element, etc.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

What is claimed is:

1. A process for producing olefins, the process comprising:
   contacting a hydrocarbon feed with at least steam at a temperature of from 700° C. to 900° C., where contacting the hydrocarbon feed with the at least steam causes at least a portion of the hydrocarbon feed to undergo steam cracking to form a cracking reaction effluent comprising at least butenes;
   separating the cracking reaction effluent to produce at least a C4 effluent comprising at least normal butenes, isobutene, and 1,3-butadiene;
   subjecting the C4 effluent to selective hydrogenation to produce a hydrogenation effluent, where the selective hydrogenation causes at least a portion of the 1,3-butadiene in the C4 effluent to react to form normal butenes;

removing isobutene from the hydrogenation effluent to produce a metathesis feed comprising at least normal butenes;

dividing the metathesis feed into a first portion and a second portion;

contacting the first portion of the metathesis feed with an isomerization catalyst comprising magnesium oxide, a metathesis catalyst directly downstream of the isomerization catalyst, and a cracking catalyst directly downstream of the metathesis catalyst to produce a metathesis reaction effluent, where:

contacting with the isomerization catalyst promotes equilibration of the isomerization reaction of 2-butene in the first portion of the metathesis feed to 1-butene;

contacting with the metathesis catalyst causes metathesis of normal butenes to produce at least ethylene, propene, and C5+ olefins; and contacting with the cracking catalyst causes at least a portion of the C5+ olefins produced through metathesis to undergo cracking reactions to produce a metathesis reaction effluent comprising propene and ethylene; and contacting the second portion of the metathesis feed with at least a portion of a system ethylene effluent in the presence of a supplemental metathesis catalyst to produce a supplemental metathesis reaction effluent, where:

contacting the second portion of the metathesis feed with the system ethylene effluent in the presence of the supplemental metathesis catalyst causes cross metathesis between at least a portion of ethylene in the system ethylene effluent and at least a portion of 2-butenes in the second portion of the metathesis feed to produce at least propene; and the supplemental metathesis reaction effluent comprises at least propene; and passing the cracking reaction effluent, the metathesis reaction effluent, and the supplemental metathesis reaction effluent to a combined separation system, and separating the cracking reaction effluent, the metathesis reaction effluent, and the supplemental metathesis reaction effluent in the combined separation system to produce at least the C4 effluent, a system propene effluent, and the system ethylene effluent.

2. The process of claim 1, in which the hydrocarbon feed comprises naphtha, a gas condensate, or both.

3. The process of claim 1, further comprising:

separating the cracking reaction effluent, the metathesis reaction effluent, and the supplemental metathesis reaction effluent in the combined separation system to produce at least a C5+ effluent, the C4 effluent, the system propene effluent, and the system ethylene effluent; and passing the C5+ effluent back into contact with the hydrocarbon feed and steam at the temperature of from 700° C. to 900° C., where contacting the C5+ effluent with the hydrocarbon feed and steam causes at least a portion of the C5+ effluent to undergo steam cracking.

4. The process of claim 3, in which the passing the C5+ effluent back into contact with the hydrocarbon feed and steam comprises:

hydrotreating the C5+ effluent to produce a hydrotreated effluent; and passing the hydrotreated effluent into contact with the hydrocarbon feed and steam at the temperature of from 700° C. to 900° C., where contacting causes at least a portion of the hydrotreated effluent to undergo steam cracking.

5. The process of claim 1, wherein separating the cracking reaction effluent, the metathesis reaction effluent, and the supplemental metathesis reaction effluent in the combined separation system further produces a C5+ effluent.

6. The process of claim 1, in which subjecting the C4 effluent to selective hydrogenation comprises contacting the C4 effluent with hydrogen in the presence of a selective hydrogenation catalyst under conditions sufficient to cause at least a portion of the 1,3-butadiene in the C4 effluent to undergo hydrogenation to produce a hydrogenation effluent comprising a greater concentration of normal butenes compared to the concentration of normal butenes in the C4 effluent.

7. The process of claim 1, in which removing isobutene comprises:

contacting the hydrogenation effluent with methanol under reaction conditions sufficient to convert at least a portion of the isobutene in the hydrogenation effluent to methyl tert-butyl ether to produce an MTBE reaction product; and separating at least a portion of the methyl tert-butyl ether from the MTBE reaction product to produce an MTBE effluent comprising the methyl tert-butyl ether and the metathesis feed comprising butene.

8. The process of claim 7, further comprising recovering at least a portion of the methyl-tert-butyl ether from the MTBE effluent.

9. The process of claim 8, further comprising:

contacting the MTBE effluent with a cracking catalyst under conditions sufficient to produce an isobutene effluent, where the contacting causes at least a portion of the methyl tert-butyl ether in the MTBE effluent to react to form isobutene; and passing the isobutene effluent back into the hydrocarbon feed and subjecting the isobutene effluent to steam cracking.

10. The process of claim 1, comprising providing the hydrocarbon feed comprising a gas condensate recovered from natural gas.

11. The process of claim 10, wherein the hydrocarbon feed has a specific gravity of from 0.5 to 0.8.

12. The process of claim 10, wherein the hydrocarbon feed comprises at least 70 wt. % hydrocarbons having boiling point temperatures less than or equal to 265° C.

\* \* \* \* \*